US011918580B2

(12) United States Patent
Minucci et al.

(10) Patent No.: US 11,918,580 B2
(45) Date of Patent: Mar. 5, 2024

(54) USE OF A COMBINATIONAL THERAPY OF LSD1 INHIBITORS WITH P21 ACTIVATORS IN THE TREATMENT OF CANCER

(71) Applicants: Istituto Europeo di Oncologia S.r.l., Milan (IT); Università degli Studi Di Milano, Milan (IT)

(72) Inventors: Saverio Minucci, Milan (IT); Pier Giuseppe Pelicci, Milan (IT); Seyed Amir Hosseini, Milan (IT)

(73) Assignees: Istituto Europeo di Oncologia S.r.l., Milan (IT); Università degli Studi Di Milano, Milan (IT)

( * ) Notice: Subject to any disclaimer, the term of this patent is extended or adjusted under 35 U.S.C. 154(b) by 702 days.

(21) Appl. No.: 16/608,003

(22) PCT Filed: Apr. 25, 2018

(86) PCT No.: PCT/EP2018/060637
§ 371 (c)(1),
(2) Date: Oct. 24, 2019

(87) PCT Pub. No.: WO2018/197583
PCT Pub. Date: Nov. 1, 2018

(65) Prior Publication Data

US 2021/0100800 A1 Apr. 8, 2021

Related U.S. Application Data

(60) Provisional application No. 62/490,547, filed on Apr. 26, 2017.

(51) Int. Cl.
| | |
|---|---|
| *A61P 35/00* | (2006.01) |
| *A61K 31/135* | (2006.01) |
| *A61K 31/165* | (2006.01) |
| *A61K 31/167* | (2006.01) |
| *A61K 31/18* | (2006.01) |
| *A61K 31/325* | (2006.01) |
| *A61K 31/343* | (2006.01) |
| *A61K 31/366* | (2006.01) |
| *A61K 31/4025* | (2006.01) |
| *A61K 31/4045* | (2006.01) |
| *A61K 31/407* | (2006.01) |
| *A61K 31/4155* | (2006.01) |
| *A61K 31/4184* | (2006.01) |
| *A61K 31/437* | (2006.01) |
| *A61K 31/44* | (2006.01) |
| *A61K 31/4406* | (2006.01) |
| *A61K 31/4439* | (2006.01) |
| *A61K 31/445* | (2006.01) |
| *A61K 31/47* | (2006.01) |
| *A61K 31/473* | (2006.01) |
| *A61K 31/495* | (2006.01) |
| *A61K 31/496* | (2006.01) |
| *A61K 31/506* | (2006.01) |
| *A61K 31/519* | (2006.01) |
| *A61K 31/5375* | (2006.01) |
| *A61K 31/549* | (2006.01) |

(Continued)

(52) U.S. Cl.
CPC .......... *A61K 31/519* (2013.01); *A61K 31/135* (2013.01); *A61K 31/165* (2013.01); *A61K 31/167* (2013.01); *A61K 31/18* (2013.01); *A61K 31/325* (2013.01); *A61K 31/343* (2013.01); *A61K 31/366* (2013.01); *A61K 31/4025* (2013.01); *A61K 31/4045* (2013.01); *A61K 31/407* (2013.01); *A61K 31/4155* (2013.01); *A61K 31/4184* (2013.01); *A61K 31/437* (2013.01); *A61K 31/44* (2013.01); *A61K 31/4406* (2013.01); *A61K 31/4439* (2013.01); *A61K 31/445* (2013.01); *A61K 31/47* (2013.01); *A61K 31/473* (2013.01); *A61K 31/495* (2013.01); *A61K 31/496* (2013.01); *A61K 31/506* (2013.01); *A61K 31/5375* (2013.01); *A61K 38/15* (2013.01); *A61P 35/00* (2018.01); *A61P 35/02* (2018.01)

(58) Field of Classification Search
CPC .. A61K 31/135; A61K 31/165; A61K 31/167; A61K 31/18; A61K 31/325; A61K 31/343; A61K 31/366; A61K 31/4025; A61K 31/4045; A61K 31/407; A61K 31/4155; A61K 31/4184; A61K 31/437; A61K 31/44; A61K 31/4406
See application file for complete search history.

(56) References Cited

U.S. PATENT DOCUMENTS

2018/0311245 A1 11/2018 Shailubhai

FOREIGN PATENT DOCUMENTS

| WO | WO 2011/131576 A1 | 10/2011 |
|---|---|---|
| WO | WO 2012/135113 A2 | 10/2012 |

(Continued)

OTHER PUBLICATIONS

National Institute of Cancer—understanding and related topics, accessed Aug. 21, 2014 at URL: cancer.gov/cancertopics/understandingcancer, 63 pages (Year: 2014).*

(Continued)

*Primary Examiner* — Julie Ha
*Assistant Examiner* — Kristina M Hellman
(74) *Attorney, Agent, or Firm* — COOLEY LLP; Heidi A. Erlacher; Thomas J. Paxton

(57) ABSTRACT

The present disclosure relates to methods of treating cancer and pharmaceutical compositions for use in the treatment of cancer, including LSD1-inhibitor-resistant cancers, comprising administering to a subject an effective amount of a cell cycle inhibitor, such as a CDK4/6 inhibitor or a p21 enhancer, and an effective amount of a LSD1 inhibitor.

10 Claims, 59 Drawing Sheets

(51) Int. Cl.
*A61K 38/15* (2006.01)
*A61P 35/02* (2006.01)

(56) References Cited

FOREIGN PATENT DOCUMENTS

| WO | WO 2013/057322 A1 | 4/2013 |
| WO | WO 2014/086790 A1 | 6/2014 |
| WO | WO 2015/181380 A1 | 12/2015 |
| WO | WO 2016/034946 A2 | 3/2016 |

OTHER PUBLICATIONS

Merck Manuals Lung Carcinoma accessed Mar. 12, 2017 at URL merckmanuals.com/professional/pulmonary-disorders/tumors-of-the-lungs/lung-carcinoma, 18 pages (Year: 2017).*
Merck Manual Colorectal Cancer accessed Aug. 21, 2014 at URL merckmanuals.com/home/digestive_disorders/tumors_of_the_digestive_system/colorectal_cancer.htm, 5 pages (Year: 2014).*
Merck Manuals Neuroblastoma accessed Mar. 12, 2017 at URL merckmanuals.com/professional/ pediatrics/pediatric-cancers/neuroblastoma, 4 pages (Year: 2017).*
Merck Manual Prostate Cancer accessed Aug. 21, 2014 at URL: merckmanuals.com/home/kidney_and_urinary_tract_disorders/cancers_of_the_kidney_and_genitourinary_tract/prostate_cancer.html?qt=prostate cancer&alt=sh, 8 pages (Year: 2014).*
Cholangiocarcinoma accessed Mar. 12, 2017 at URL surgery.usc.edu/divisions/tumor/pancreasdiseases/web%20pages/BILIARY%20SYSTEM/cholangiocarcinoma, 2 pages (Year: 2017).*
Thyroid cancer accessed Mar. 12, 2017 at URL www.merckmanuals.com/professional/endocrine-and-metabolic-disorders/thyroid-disorders/thyroid-cancers, 4 pages (Year: 2017).*
Renal cell carcinoma, accessed Mar. 12, 2017 at URL merckmanuals.com/professional/genitourinary-disorders/genitourinary-cancer/renal-cell-carcinoma, 6 pages (Year: 2017).*
Merck Manual Bladder Cancer accessed Aug. 21, 2014 at URL: merckmanuals.com/home/kidney_and_urinary_tract_disorders/cancers_of_the_kidney_and_genitourinary_tract/bladder_cancer.html, 2 pages (Year: 2014).*
Merck Manual overview of Leukemia accessed Aug. 21, 2014 at URL: merckmanuals.com/home/blood_disorders/leukemias/overview_of_leukemia.html , 2 pages (Year: 2014).*
Yang et al., "CDK4/6 Inhibitor PD 0332991 Sensitizes Acute Myeloid Leukemia to Cytarabine-Mediated Cytotoxicity," Cancer Res. 75(9) 1838-1845 (2015) (Year: 2015).*
Lynch et al., "LSD1 inhibition: a therapeutic strategy in cancer?," Expert Opin. Ther. Targets 16(12):1239-1249 (2012) (Year: 2012).*
CAS No. 1831167-97-5, entered STN: 2015, 1 page.
CAS No. 265312-55-8, entered STN: 2000, 1 page.
CAS No. 359886-84-3, entered STN: 2001, 1 page.
CAS No. 546102-60-7, entered STN: 2003, 1 page.
Binda, C. et al. "Biochemical, Structural, and Biological Evaluation of Tranylcypromine Derivatives as Inhibitors of Histone Demethylases LSDI and LSD2", Journal of the American Chemical Society, 2010, vol. 132, No. 19, p. 6827-6833.
Fiskus, W. et al. "Highly effective combination of LSD1 (KDMIA) antagonist and pan-histone deacetylase inhibitor against human AML cells", Leukemia, 2014, vol. 28, No. 11, p. 2155-2164.
Kim et al. "The Stress-activated Protein Kinases p38α and JNKI Stabilize p21$^{Cip1}$ by Phosphorylation," The Journal of Biological Chemistry, 2002, vol. 277, No. 33, p. 29792-29802.
Maes, T. et al. "Advances in the development of histone lysine demethylase inhibitors", Current Opinion in Phamacology, 2015, vol. 23, p. 52-60.
Ramirez, L. et al. "Abstract 1427: HDAC and LSD1 Inhibitors Synergize to Induce Cell Death in Acute Leukemia Cells", Blood, 2011, vol. 118, No. 21, p. 1427-1428.
Singh, M et al. "Preclinical activity of combined HDAC and KDMIA inhibition in glioblastoma", Neuro-Oncology: Official Journal of the World Federation of Neuro-Oncology, 2015, vol. 17, No. 11, p. 1463-1473.

* cited by examiner

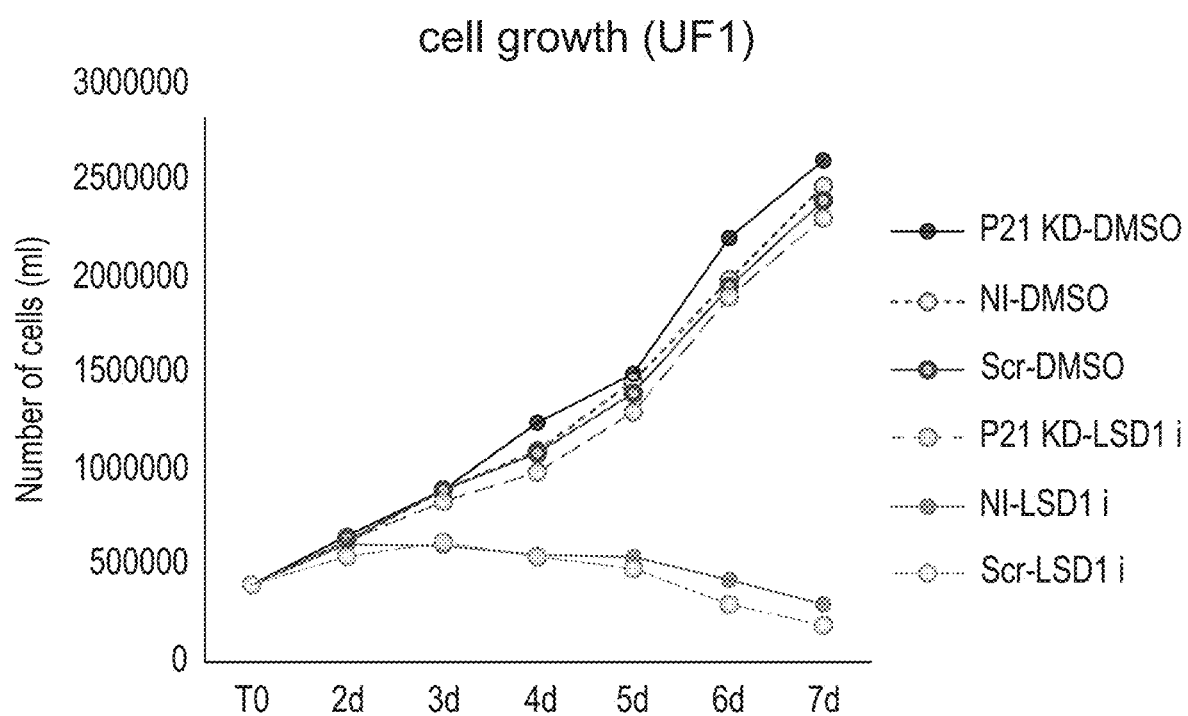

Cell cycle

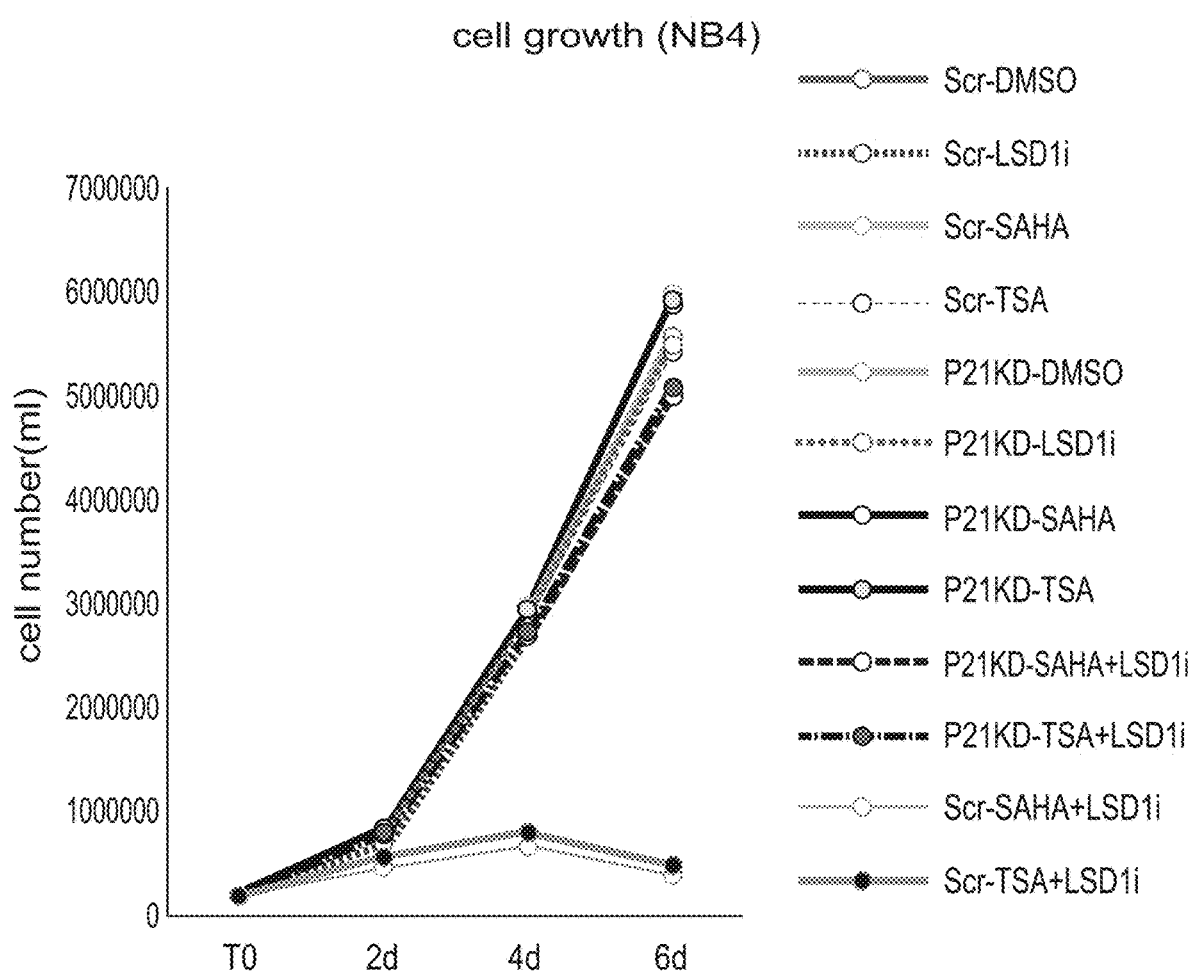

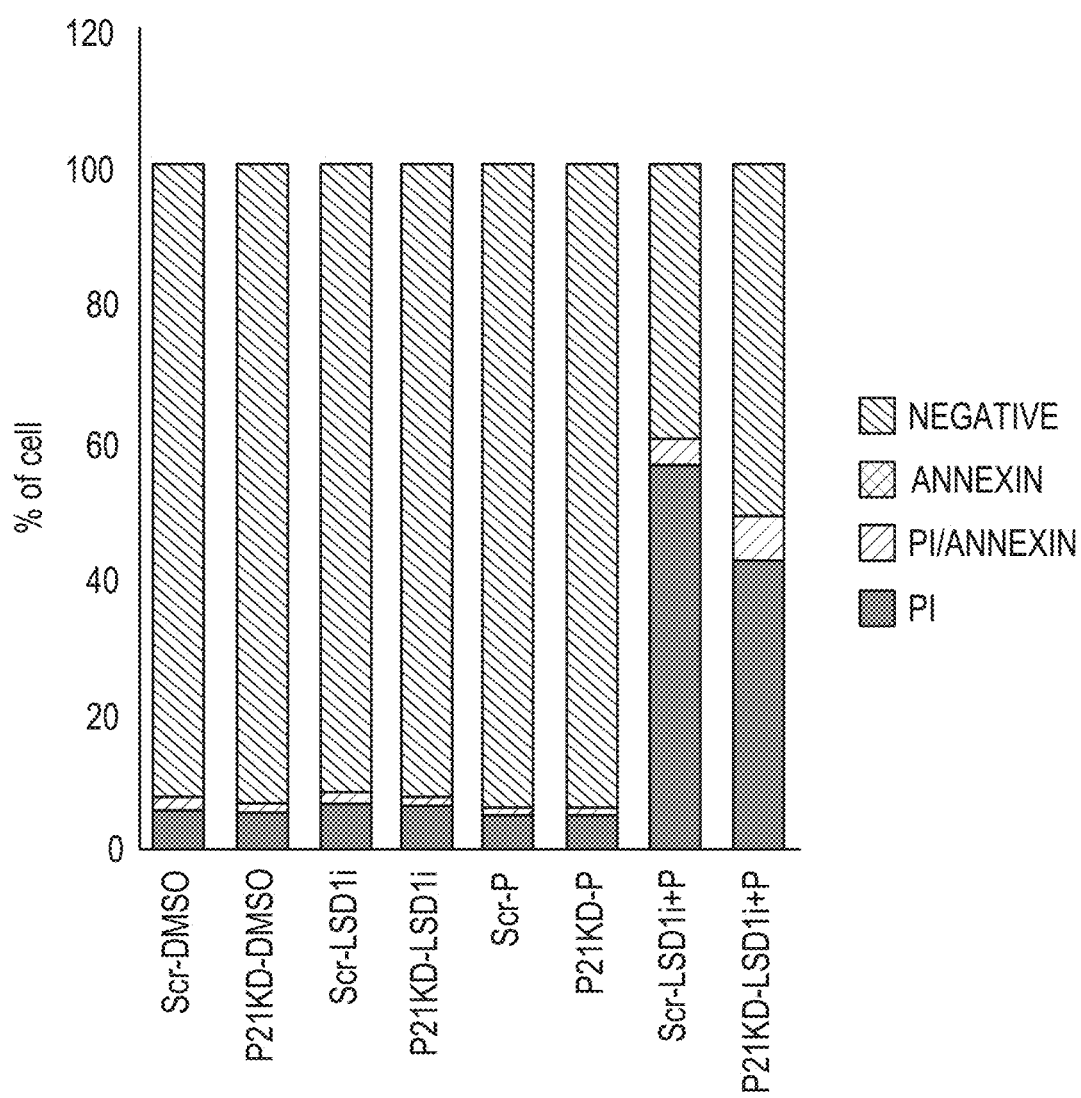

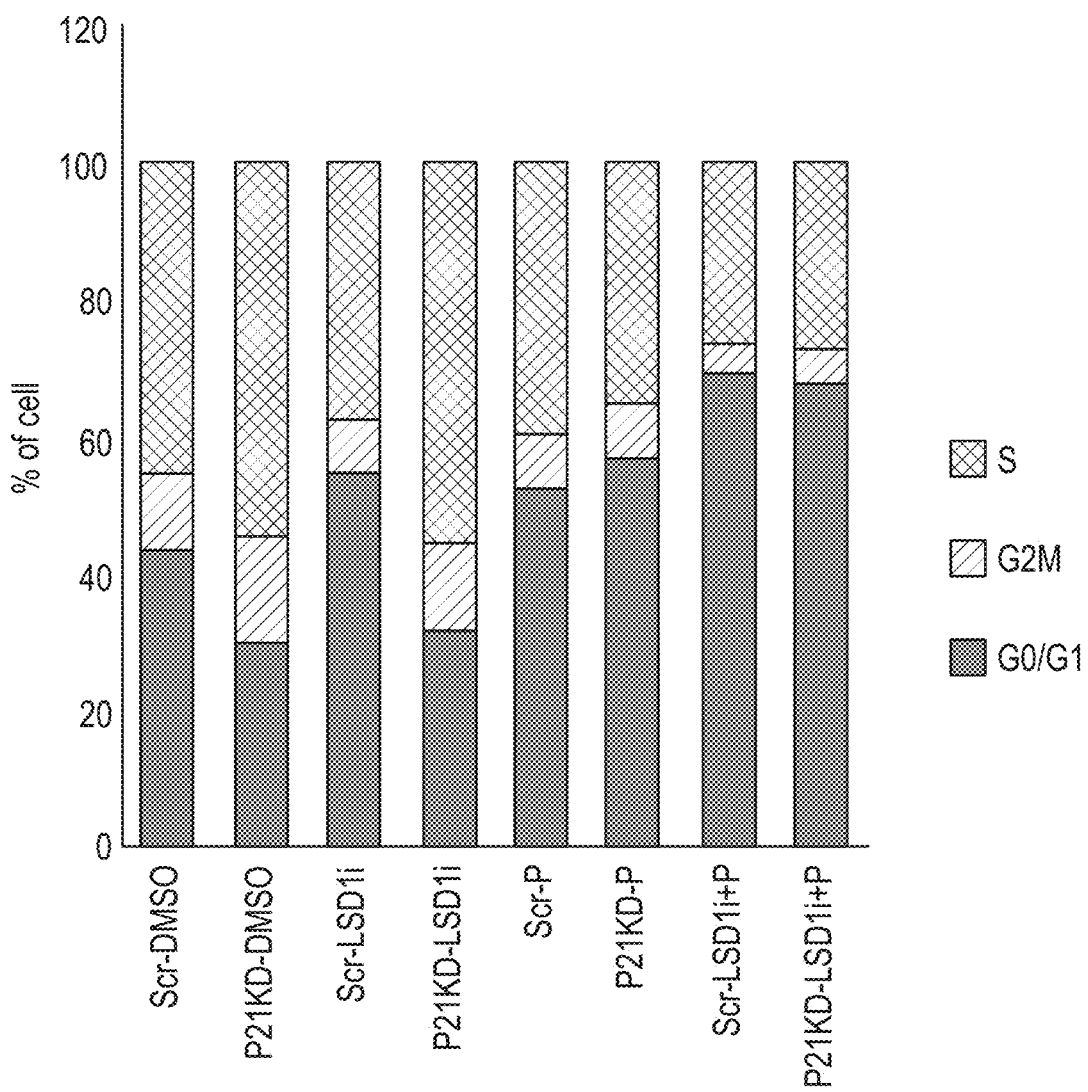

Fig. 15A
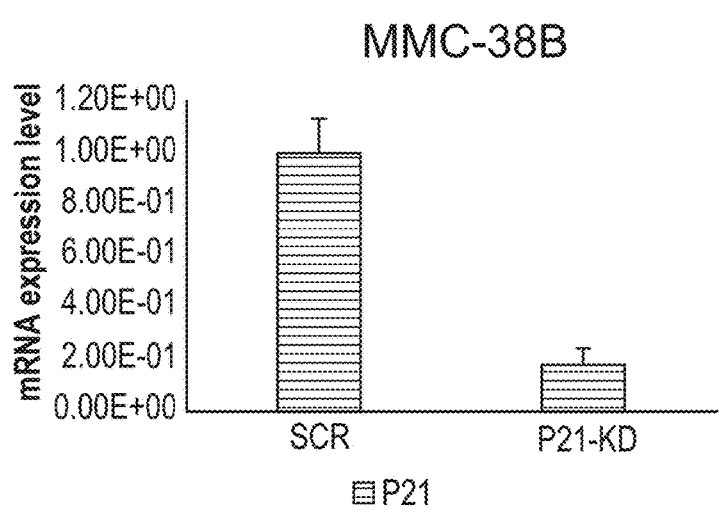
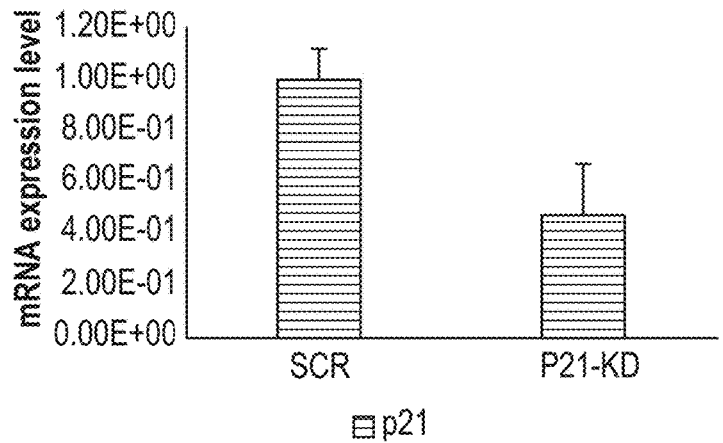
Fig. 15B
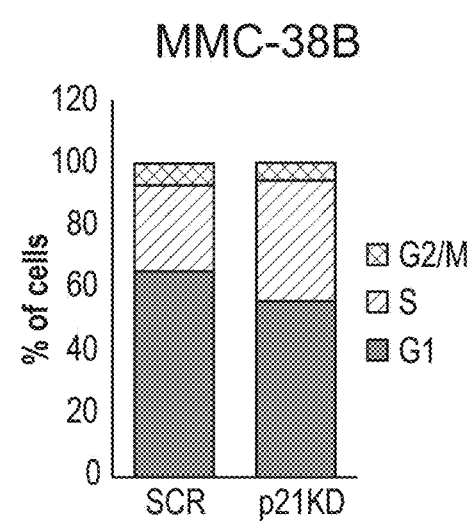
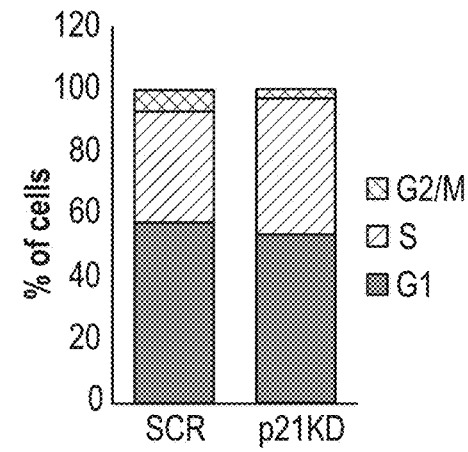

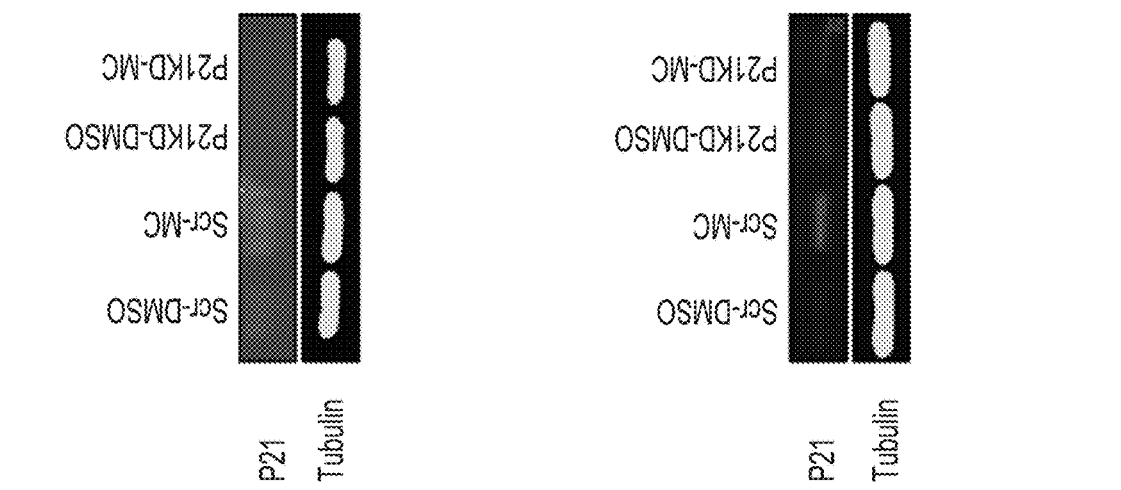
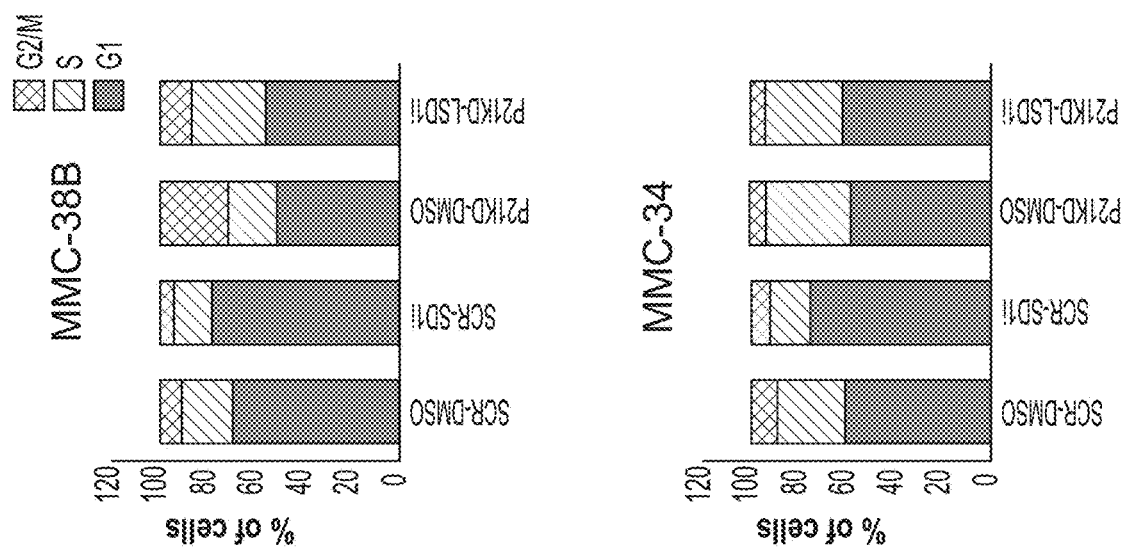
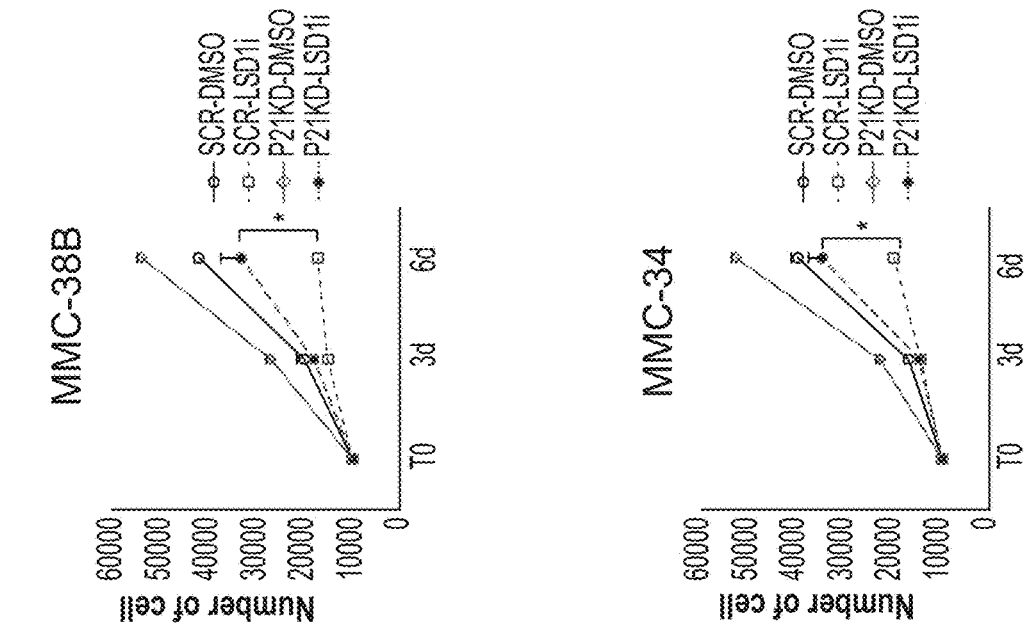

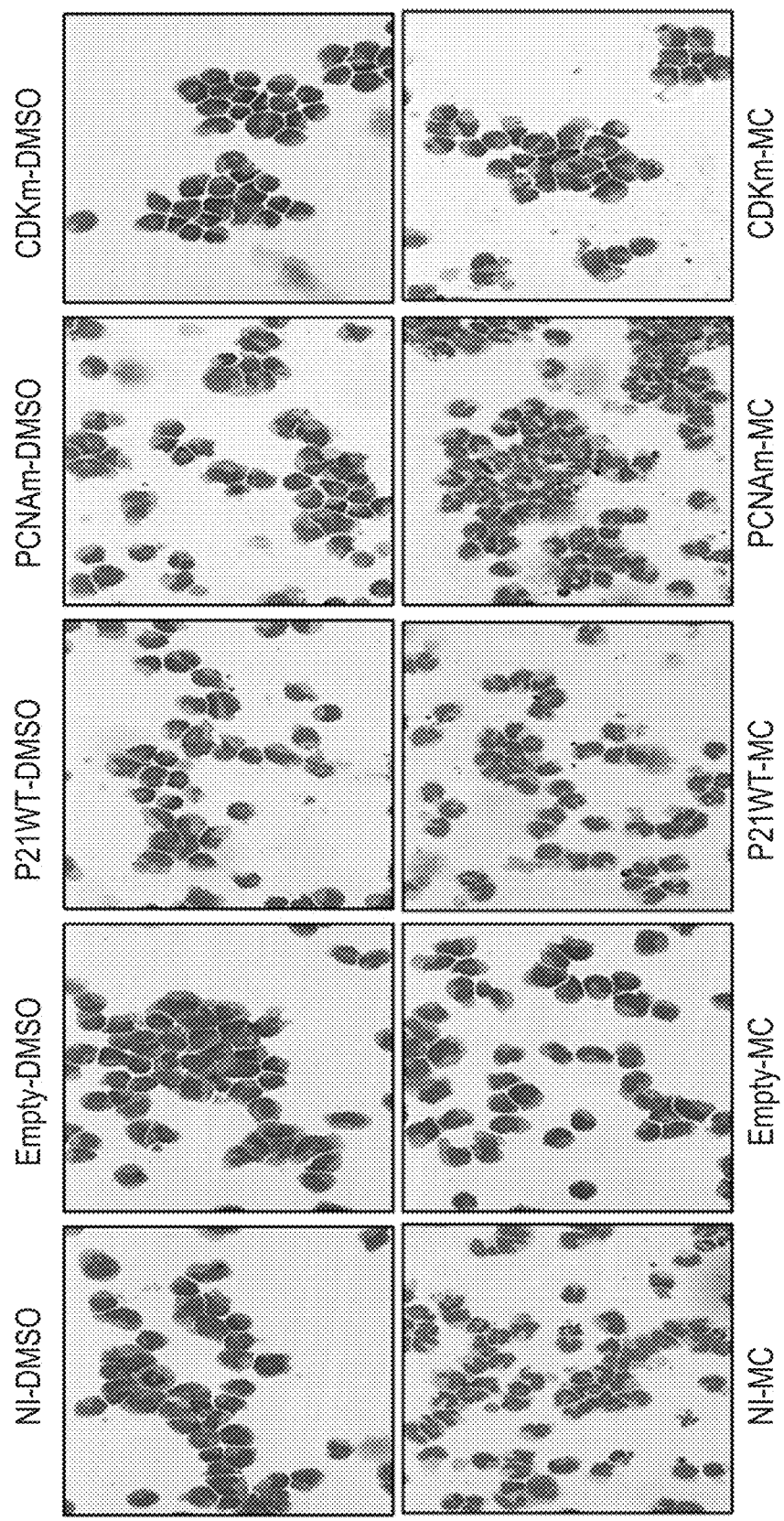

USE OF A COMBINATIONAL THERAPY OF LSD1 INHIBITORS WITH P21 ACTIVATORS IN THE TREATMENT OF CANCER

RELATED APPLICATIONS

This application is a U.S. National Phase application, filed under 35 U.S.C. § 371(c), of International Application No. PCT/EP2018/060637, filed on Apr. 25, 2018, which claims priority to, and the benefit of, U.S. Application No. 62/490,547, filed Apr. 26, 2017, the contents of each of which are incorporated by reference herein in their entireties.

TECHNICAL FIELD

The present disclosure relates to methods of treating cancer comprising administering to a subject an effective amount of a cell cycle inhibitor and an effective amount of a LSD1 inhibitor.

BACKGROUND

It is estimated that 8.8 million people worldwide died from cancer in 2015, which accounts for nearly one out of every six deaths globally. The World Health Organization estimated that the total economic costs of cancer in 2010 were about $1.16 trillion. As such, there is a need for the development of novel therapies for the treatment of cancers, and in particular, cancers that are resistant to currently available therapies.

SUMMARY

In one aspect, this application pertains to a method for treating a subject having cancer, which comprises
  i. administering to the subject an effective amount of a cell cycle inhibitor, and
  ii. administering to the subject an effective amount of a LSD1 inhibitor,
  wherein the cell cycle inhibitor is a CDK4/6 inhibitor or a p21 enhancer.

In one aspect, this application pertains to a method for treating a subject having cancer, which comprises
  i. administering to the subject an effective amount of a CDK4/6 inhibitor; and
  ii. administering to the subject an effective amount of a LSD1 inhibitor.

In one aspect, this application pertains to a method for treating a subject having cancer, which comprises
  i. administering to the subject an effective amount of a p21 enhancer; and
  ii. administering to the subject an effective amount of a LSD1 inhibitor.

In one embodiment, the cell cycle inhibitor is administered before, concurrently, or after the LSD1 inhibitor.

In one embodiment, the cell cycle inhibitor is administered before the LSD1 inhibitor.

In one embodiment, the cell cycle inhibitor is administered about 24 hours, about 48 hours, about 72 hours, or about 1 week before the LSD1 inhibitor.

In one embodiment, the cell cycle inhibitor is administered concurrently with the LSD1 inhibitor.

In one embodiment, the cell cycle inhibitor is administered after the LSD1 inhibitor.

In one embodiment, the CDK4/6 inhibitor is selected from the group consisting of: palbociclib, ribociclib (LEE011), hygrolidin, P276-00, fascaplysin, abemaciclib, arcyriaflavin A, CINK4, AM-5992, CDK4 Inhibitor (CAS #546102-60-7), CDK4 Inhibitor III (CAS #265312-55-8), Cdk4/6 Inhibitor IV (CAS #359886-84-3), MM-D37K, NSC 625987, ON-123300, or any pharmaceutically acceptable salt thereof, and any combination thereof.

In one embodiment, the CDK4/6 inhibitor is palbociclib or a pharmaceutically acceptable salt thereof.

In one embodiment, the p21 enhancer is a HDAC inhibitor.

In one embodiment, the HDAC inhibitor is selected from the group consisting of: trichostatin A (TSA), vorinostat (suberoylanilide hydroxamic acid, SAHA), entinostat, panobinostat, romidepsin, belinostat, mocetinostat, givinostat, pracinostat, chidamide, quisinostat, abexinostat, or a pharmaceutically acceptable salt thereof, and any combination thereof.

In one embodiment, the LSD1 inhibitor is selected from the group consisting of a compound of Formula (I), Formula (Ia), Formula (II), Formula (III), any other compound indicated as an LSD1 inhibitor, or a stereoisomer or a pharmaceutically acceptable salt thereof. In one embodiment, the LSD1 inhibitor is selected from the group consisting of a compound of Formula (I), Formula (Ia), Formula (II), Formula (III), or a stereoisomer or a pharmaceutically acceptable salt thereof.

In one embodiment, the LSD1 inhibitor is selected from the group consisting of: MC2580, DDP38003, tranylcypromine, (R)-4-[5-(Pyrrolidin-3-ylmethoxy)-2-p-tolyl-pyridin-3-yl]-benzonitrile, 1-(4-methyl-1-piperazinyl)-2-[[(1R*,2S*)-2-[4-phenylmethoxy)phenyl]cyclopropyl]amino]ethanone, N-[4-[trans-2-aminocyclopropyl]phenyl]-4-(4-methylpiperazin-1-yl)benzamide,

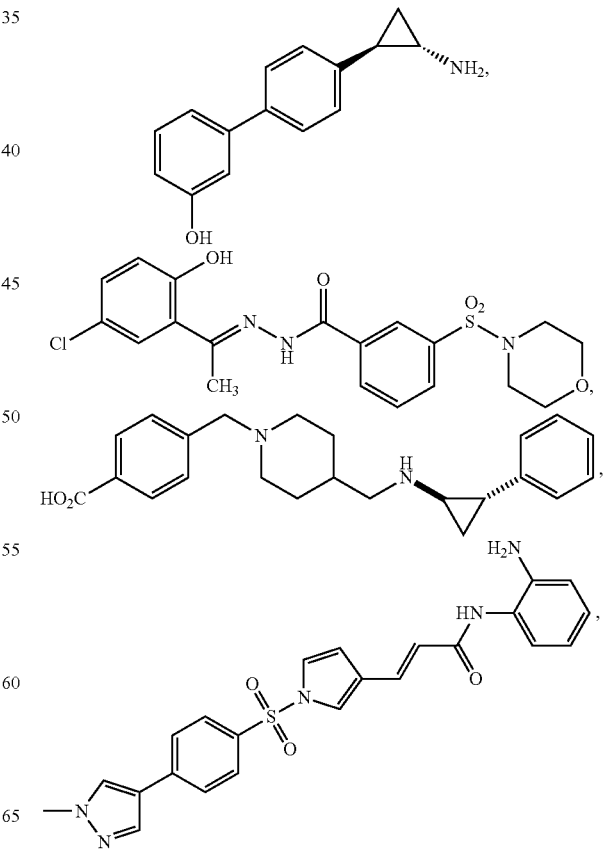

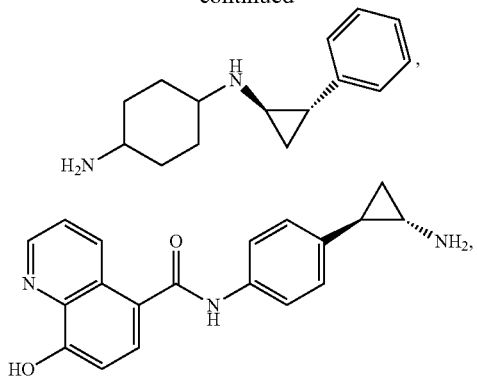

or a stereoisomer or a pharmaceutically acceptable salt thereof.

In one embodiment, the LSD1 inhibitor is MC2580 or a stereoisomer or a pharmaceutically acceptable salt thereof.

In one embodiment, the LSD1 inhibitor is DDP38003 or a stereoisomer or a pharmaceutically acceptable salt thereof.

In one embodiment, the cancer is selected from the group consisting of leukemia (including acute promyelocytic leukemia and acute myeloid leukemia), prostate cancer, breast cancer, lung cancer (including small cell lung cancer), colorectal cancer, melanomas, bladder cancer, brain/CNS cancer, cervical cancer, esophageal cancer, gastric cancer, head/neck cancer, kidney cancer, liver cancer, lymphomas, ovarian cancer, pancreatic cancer, and sarcomas.

In one embodiment, the cancer is selected from the group consisting of acute promyelocytic leukemia, acute myeloid leukemia, small cell lung carcinoma, and melanoma.

In one embodiment, the cancer is acute promyelocytic leukemia.

In one embodiment, the cancer is acute myeloid leukemia.

In one embodiment, the cancer is small cell lung carcinoma.

In one embodiment, the cancer is melanoma.

In one embodiment, the cancer is a solid tumor or blood tumor.

In one embodiment, the cancer is a solid tumor.

In one embodiment, the cancer is a blood tumor.

In one embodiment, the cancer is a.LSD1-inhibitor-resistant cancer.

In one embodiment, the LSD1-inhibitor-resistant cancer comprises cancerous cells having a reduced level of p21 expression or a loss of p21 function as compared to cancerous cells that are sensitive to LSD1 inhibitors.

In one aspect, this application pertains to a method for treating a subject having LSD1-inhibitor-resistant cancer by sensitizing cells of the cancer to LSD1 inhibitors, which comprises
  i. administering to the subject an effective amount of a cell cycle inhibitor, and
  ii. administering to the subject an effective amount of a LSD1 inhibitor,
  wherein the cell cycle inhibitor is a CDK4/6 inhibitor or a p21 enhancer.

In one aspect, this application pertains to a method for treating a subject having LSD1-inhibitor-resistant cancer by sensitizing cells of the cancer to LSD1 inhibitors, which comprises
  i. administering to the subject an effective amount of a CDK4/6 inhibitor, and
  ii. administering to the subject an effective amount of a LSD1 inhibitor.

In one aspect, this application pertains to a method for treating a subject having LSD1-inhibitor-resistant cancer by sensitizing cells of the cancer to LSD1 inhibitors, which comprises
  i. administering to the subject an effective amount of a p21 enhancer; and
  ii. administering to the subject an effective amount of a LSD1 inhibitor.

In one embodiment, the method for treating a subject having LSD1-inhibitor-resistant cancer by sensitizing cells of the cancer to LSD1 inhibitors additionally comprises a step of evaluating the cancer to predict resistance to LSD1 inhibitors prior to administration of the cell cycle inhibitor.

In one embodiment, for the method for treating a subject having LSD1-inhibitor-resistant cancer by sensitizing cells of the cancer to LSD1 inhibitors, the cell cycle inhibitor is administered before, concurrently, or after the LSD1 inhibitor.

In one embodiment, for the method for treating a subject having LSD1-inhibitor-resistant cancer by sensitizing cells of the cancer to LSD1 inhibitors, the cell cycle inhibitor is administered before the LSD1 inhibitor.

In one embodiment, for the method for treating a subject having LSD1-inhibitor-resistant cancer by sensitizing cells of the cancer to LSD1 inhibitors, the cell cycle inhibitor is administered about 24 hours, about 48 hours, about 72 hours, or about 1 week before the LSD1 inhibitor.

In one embodiment, for the method for treating a subject having LSD1-inhibitor-resistant cancer by sensitizing cells of the cancer to LSD1 inhibitors, the cell cycle inhibitor is administered concurrently with the LSD1 inhibitor.

In one embodiment, for the method for treating a subject having LSD1-inhibitor-resistant cancer by sensitizing cells of the cancer to LSD1 inhibitors, the cell cycle inhibitor is administered after the LSD1 inhibitor.

In one embodiment, the CDK4/6 inhibitor is selected from the group consisting of: palbociclib, ribociclib (LEE011), hygrolidin, P276-00, fascaplysin, abemaciclib, arcyriaflavin A, CINK4, AM-5992, CDK4 Inhibitor (CAS #546102-60-7), CDK4 Inhibitor III (CAS #265312-55-8), Cdk4/6 Inhibitor IV (CAS #359886-84-3), MM-D37K, NSC 625987, ON-123300, or any pharmaceutically acceptable salt thereof, and any combination thereof.

In one embodiment, the CDK4/6 inhibitor is palbociclib or a pharmaceutically acceptable salt thereof.

In one embodiment, the p21 enhancer is a HDAC inhibitor.

In one embodiment, the HDAC inhibitor is selected from the group consisting of: trichostatin A (TSA), vorinostat (suberoylanilide hydroxamic acid, SAHA), entinostat, panobinostat, romidepsin, belinostat, mocetinostat, givinostat, pracinostat, chidamide, quisinostat, abexinostat, or a pharmaceutically acceptable salt thereof, and any combination thereof.

In one embodiment, the LSD1 inhibitor is selected from the group consisting of a compound of Formula (I), Formula (Ia), Formula (II), Formula (III), any other compound indicated as an LSD1 inhibitor, or a stereoisomer or a pharmaceutically acceptable salt thereof. In one embodiment, the LSD1 inhibitor is selected from the group consisting of a compound of Formula (I), Formula (Ia), Formula (II), Formula (III), or a stereoisomer or a pharmaceutically acceptable salt thereof.

In one embodiment, the LSD1 inhibitor is selected from the group consisting of: MC2580, DDP38003, tranylcypromine, (R)-4-[5-(Pyrrolidin-3-ylmethoxy)-2-p-tolyl-pyridin-3-yl]-benzonitrile, 1-(4-methyl-1-piperazinyl)-2-[[(1R*,2S*)-2-[4-phenylmethoxy)phenyl]cyclopropyl]amino] ethanone, N-[4-[trans-2-aminocyclopropyl]phenyl]-4-(4-methylpiperazin-1-yl)benzamide,

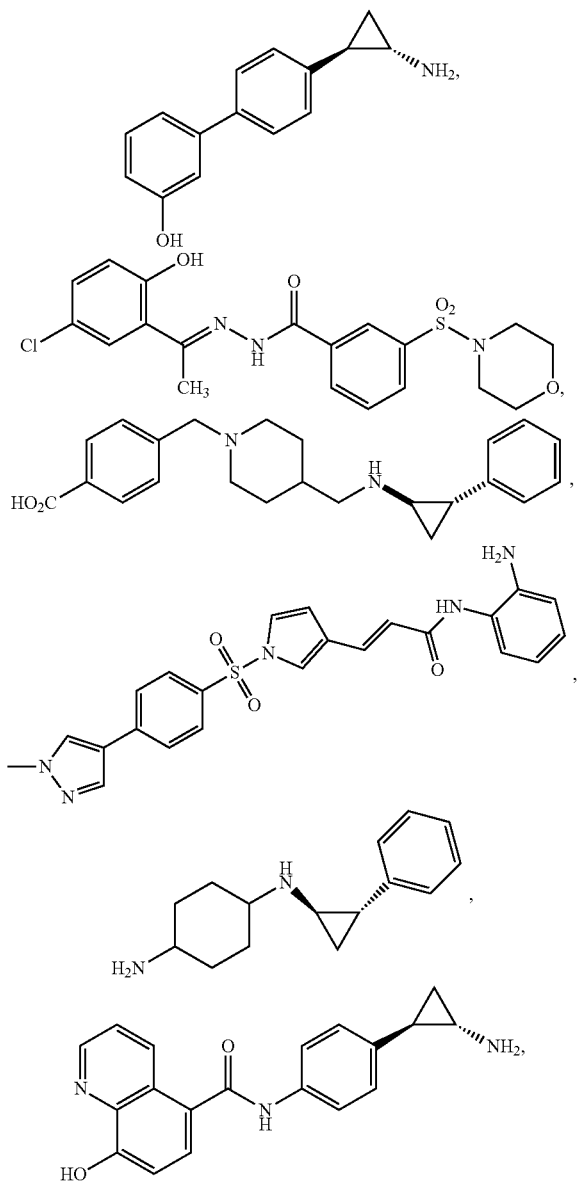

or a stereoisomer or a pharmaceutically acceptable salt thereof.

In one embodiment, the LSD1 inhibitor is MC2580 or a stereoisomer or a pharmaceutically acceptable salt thereof.

In one embodiment, the LSD1 inhibitor is DDP38003 or a stereoisomer or a pharmaceutically acceptable salt thereof.

In one embodiment, for the method for treating a subject having LSD1-inhibitor-resistant cancer by sensitizing cells of the cancer to LSD1 inhibitors, the LSD1-inhibitor-resistant cancer comprises cancerous cells having a reduced level of p21 expression or a loss of p21 function as compared to cancerous cells that are sensitive to LSD1 inhibitors.

In one embodiment, for the method for treating a subject having LSD1-inhibitor-resistant cancer by sensitizing cells of the cancer to LSD1 inhibitors, the LSD1-inhibitor-resistant cancer comprises cancerous cells having a reduced level of p21 expression as compared to cancerous cells that are sensitive to LSD1 inhibitors.

In one embodiment, for the method for treating a subject having LSD1-inhibitor-resistant cancer by sensitizing cells of the cancer to LSD1 inhibitors, the LSD1-inhibitor-resistant cancer comprises cancerous cells having a loss of p21 function as compared to cancerous cells that are sensitive to LSD1 inhibitors.

In one embodiment, the cancer is selected from the group consisting of leukemia (including acute promyelocytic leukemia and acute myeloid leukemia), prostate cancer, breast cancer, lung cancer (including small cell lung cancer), colorectal cancer, melanomas, bladder cancer, brain/CNS cancer, cervical cancer, esophageal cancer, gastric cancer, head/neck cancer, kidney cancer, liver cancer, lymphomas, ovarian cancer, pancreatic cancer, and sarcomas.

In one embodiment, the cancer is selected from the group consisting of acute promyelocytic leukemia, acute myeloid leukemia, small cell lung carcinoma, and melanoma.

In one embodiment, the cancer is acute promyelocytic leukemia.

In one embodiment, the cancer is acute myeloid leukemia.

In one embodiment, the cancer is small cell lung carcinoma.

In one embodiment, the cancer is melanoma.

In one embodiment, the cancer is a solid tumor or blood tumor.

In one embodiment, the cancer is a solid tumor.

In one embodiment, the cancer is a blood tumor.

In one aspect, this application pertains to a pharmaceutical composition for treating or ameliorating the effects of a cancer in a subject in need thereof, comprising
  i. a therapeutically-effective amount of an LSD1 inhibitor,
  ii. a therapeutically-effective amount of a cell cycle inhibitor, and
  iii. a pharmaceutically-acceptable excipient.
  wherein the cell cycle inhibitor is a CDK4/6 inhibitor or a p21 enhancer.

In one aspect, this application pertains to a pharmaceutical composition for treating or ameliorating the effects of a cancer in a subject in need thereof comprising
  i. a therapeutically-effective amount of an LSD1 inhibitor,
  ii. a therapeutically-effective amount of a CDK4/6 inhibitor, and
  iii. a pharmaceutically-acceptable excipient.

In one aspect, this application pertains to a pharmaceutical composition for treating or ameliorating the effects of a cancer in a subject in need thereof, comprising
  iv. a therapeutically-effective amount of an LSD1 inhibitor;
  v. a therapeutically-effective amount of a p21 enhancer; and
  vi. a pharmaceutically-acceptable excipient.

In one embodiment, in the pharmaceutical composition for treating or ameliorating the effects of a cancer in a subject in need thereof, the LSD1 inhibitor and the cell cycle inhibitor are in a unified dosage form or in separate dosage forms.

In one embodiment, in the pharmaceutical composition for treating or ameliorating the effects of a cancer in a subject in need thereof, the LSD1 inhibitor and the cell cycle inhibitor are in a unified dosage form.

In one embodiment, in the pharmaceutical composition for treating or ameliorating the effects of a cancer in a subject in need thereof, the LSD1 inhibitor and the cell cycle inhibitor are in a separate dosage form.

In one embodiment, for the pharmaceutical composition for treating or ameliorating the effects of a cancer in a subject in need thereof, the LSD1 inhibitor and the cell cycle inhibitor are co-administered to the subject.

In one embodiment, for the pharmaceutical composition for treating or ameliorating the effects of a cancer in a subject in need thereof, the LSD1 inhibitor and the cell cycle inhibitor are administered to the subject serially.

In one embodiment, for the pharmaceutical composition for treating or ameliorating the effects of a cancer in a subject in need thereof, the cell cycle inhibitor is administered about 24 hours, about 48 hours, about 72 hours, or about 1 week before the LSD1 inhibitor.

In one embodiment, for the pharmaceutical composition for treating or ameliorating the effects of a cancer in a subject in need thereof, the LSD1 inhibitor is administered about 24 hours, about 48 hours, about 72 hours, or about 1 week before the cell cycle inhibitor.

In one embodiment, in the pharmaceutical composition for treating or ameliorating the effects of a cancer in a subject in need thereof, the CDK4/6 inhibitor is selected from the group consisting of: palbociclib, ribociclib (LEE011), hygrolidin, P276-00, fascaplysin, abemaciclib, arcyriaflavin A, CINK4, AM-5992, CDK4 Inhibitor (CAS #546102-60-7), CDK4 Inhibitor III (CAS #265312-55-8), Cdk4/6 Inhibitor IV (CAS #359886-84-3), MM-D37K, NSC 625987, ON-123300, or any pharmaceutically acceptable salt thereof, and any combination thereof.

In one embodiment, in the pharmaceutical composition for treating or ameliorating the effects of a cancer in a subject in need thereof, the CDK4/6 inhibitor is palbociclib or a pharmaceutically acceptable salt thereof.

In one embodiment, in the pharmaceutical composition for treating or ameliorating the effects of a cancer in a subject in need thereof, the p21 enhancer is a HDAC inhibitor.

In one embodiment, in the pharmaceutical composition for treating or ameliorating the effects of a cancer in a subject in need thereof, the HDAC inhibitor is selected from the group consisting of: trichostatin A (TSA), vorinostat (suberoylanilide hydroxamic acid, SAHA), entinostat, panobinostat, romidepsin, belinostat, mocetinostat, givinostat, pracinostat, chidamide, quisinostat, abexinostat, or a pharmaceutically acceptable salt thereof, and any combination thereof.

In one embodiment, in the pharmaceutical composition for treating or ameliorating the effects of a cancer in a subject in need thereof, the LSD1 inhibitor is selected from the group consisting of a compound of Formula (I), Formula (Ia), Formula (II), Formula (III), any other compound indicated as an LSD1 inhibitor, or a stereoisomer or a pharmaceutically acceptable salt thereof. In one embodiment, the LSD1 inhibitor is selected from the group consisting of a compound of Formula (I), Formula (Ia), Formula (II), Formula (III), or a stereoisomer or a pharmaceutically acceptable salt thereof.

In one embodiment, in the pharmaceutical composition for treating or ameliorating the effects of a cancer in a subject in need thereof, the LSD1 inhibitor is selected from the group consisting of: MC2580, DDP38003, tranylcypromine, (R)-4-[5-(Pyrrolidin-3-ylmethoxy)-2-p-tolyl-pyridin-3-yl]-benzonitrile, 1-(4-methyl-1-piperazinyl)-2-[[(1R*,2S*)-2-[4-phenylmethoxy)phenyl]cyclopropyl]amino] ethanone, N-[4-[trans-2-aminocyclopropyl]phenyl]-4-(4-methylpiperazin-1-yl)benzamide,

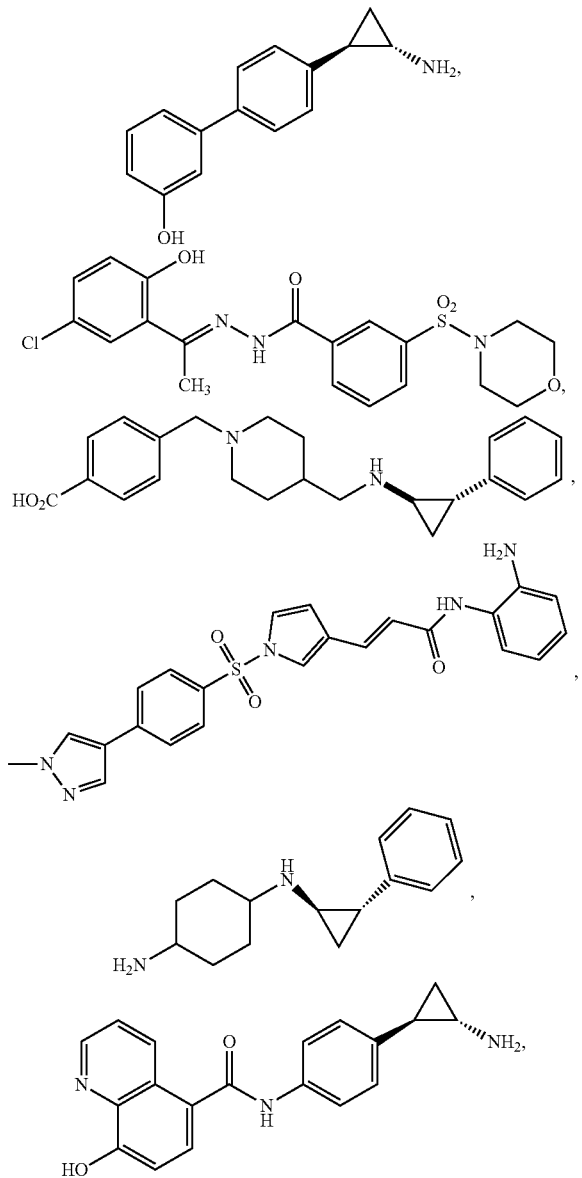

or a stereoisomer or a pharmaceutically acceptable salt thereof.

In one embodiment, in the pharmaceutical composition for treating or ameliorating the effects of a cancer in a subject in need thereof, the LSD1 inhibitor is MC2580 or a stereoisomer or a pharmaceutically acceptable salt thereof.

In one embodiment, in the pharmaceutical composition for treating or ameliorating the effects of a cancer in a subject in need thereof, the LSD1 inhibitor is DDP38003 or a stereoisomer or a pharmaceutically acceptable salt thereof.

In one embodiment, in the pharmaceutical composition for treating or ameliorating the effects of a cancer in a subject in need thereof, the cancer is selected from the group consisting of leukemia (including acute promyelocytic leukemia and acute myeloid leukemia), prostate cancer, breast cancer, lung cancer (including small cell lung cancer), colorectal cancer, melanomas, bladder cancer, brain/CNS cancer, cervical cancer, esophageal cancer, gastric cancer, head/neck cancer, kidney cancer, liver cancer, lymphomas, ovarian cancer, pancreatic cancer, and sarcomas.

In one embodiment, the cancer is selected from the group consisting of acute promyelocytic leukemia, acute myeloid leukemia, small cell lung carcinoma, and melanoma.

In one embodiment, the cancer is acute promyelocytic leukemia.

In one embodiment, the cancer is acute myeloid leukemia.

In one embodiment, the cancer is small cell lung carcinoma.

In one embodiment, the cancer is melanoma.

In one embodiment, the cancer is a solid tumor or blood tumor.

In one embodiment, the cancer is a solid tumor.

In one embodiment, the cancer is a blood tumor.

In one embodiment, the cancer is a.LSD1-inhibitor-resistant cancer.

In one embodiment, for the pharmaceutical composition for treating or ameliorating the effects of a cancer in a subject in need thereof, the LSD1-inhibitor-resistant cancer comprises cancerous cells having a reduced level of p21 expression or a loss of p21 function as compared to cancerous cells that are sensitive to LSD1 inhibitors.

In one embodiment, for the pharmaceutical composition for treating or ameliorating the effects of a cancer in a subject in need thereof, the LSD1-inhibitor-resistant cancer comprises cancerous cells having a reduced level of p21 expression as compared to cancerous cells that are sensitive to LSD1 inhibitors.

In one embodiment, for the pharmaceutical composition for treating or ameliorating the effects of a cancer in a subject in need thereof, the LSD1-inhibitor-resistant cancer comprises cancerous cells having a loss of p21 function as compared to cancerous cells that are sensitive to LSD1 inhibitors.

In one aspect, this application pertains to a pharmaceutical composition as defined in any of the above aspects or embodiments, for use in treating or ameliorating the effects of a cancer in a subject in need thereof.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Other methods and features will become apparent to those skilled in the art upon examination of the following drawings and detailed description. It is intended that all such methods and features be included within this description, be within the scope of the present invention, and be protected by the accompanying claims.

BRIEF DESCRIPTION OF THE FIGURES

FIG. 1. NB4 APL cells (and most AML cells) are resistant to LSD1 inhibition.

FIG. 2. LSD1 inhibition in UF1 cells, inhibits their growth, promotes differentiation and induces cell cycle arrest.

FIG. 6. LSD1 inhibition leads to further upregulation of P21 RNA and protein level but not in P21KD cells.

FIG. 10. P21 induction by HDAC sensitizes NB4 cells to LSD1 inhibitors. (FIG. 10A) Relative proliferation of NB4 cells infected with SCR (control) or p21 shRNA and treated with HDAC inhibitor and/or MC2580.

FIG. 11. Palbociclib (CDK4/6 inhibitor) sensitizes NB4 cells to LSD1 inhibitor. (FIG. 11D) percentage of live and apoptotic NB4 cells after 6 days treatment with indicated inhibitors. (FIG. 11E) summary of cell-cycle status of NB4 cells following 6 days treatment with indicated inhibitors. (SCR=Scramble shRNA, NI=Not Infected, LSD1i=LSD1 inhibitor=MC2580, P=palbociclib).

FIG. 15A depicts analysis of p21 mRNA relative levels in melanoma cells (MMC-38B, MMC-34), transduced with either control shRNA (SCR) or shRNA targeting p21. Values are normalized against GAPDH and referred to SCR.

FIG. 15B depicts cell-cycle status of melanoma cells infected with either control shRNA (SCR) or shRNA targeting p21.

FIG. 16A depicts relative proliferation of melanoma cells (MMC-38B and MMC-34) that were treated with p21-shRNA ("P21KD-DMSO"), scramble shRNA ("SCR-DMSO"), scramble shRNA plus LSD1 inhibitor MC2580 ("SCR-LSD1i"), or p21-shRNA plus MC2580 ("P21KD-LSD1i"). Data are presented as mean of triplicates SD.

FIG. 16B depicts cell-cycle status of melanoma cells analyzed in FIG. 16A.

FIG. 16C depicts the p21 expression level in melanoma cells analyzed in FIG. 16A.

FIG. 20C depicts representative light micrograph show Wright-Giemsa staining of UF1 cell stably transduced with shRNA targeting p21 following transfection with empty or p21-WT, p21-PCNAm, p21-CDKm expression vector following treatment with MC2580 or DMSO. P value<0.05 (*), P<0.01 () and P<0.001 (*). (NI: Not Infected).

DETAILED DESCRIPTION

Figure 1A:
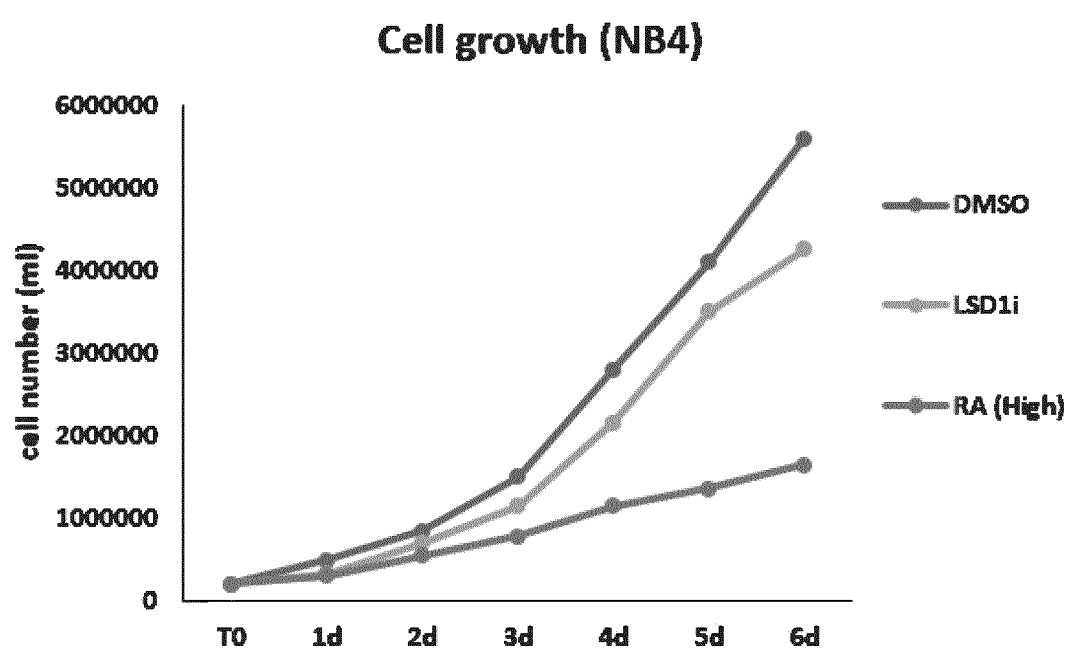
(FIG. 1A) Relative proliferation of NB4 APL cells treated with MC2580 (2 M) and RA (1 μM) for indicated times (DMSO serves as control).

In the present application, the term "cell cycle inhibitor" refers to a CDK4/6 inhibitor or a p21 enhancer.

In the present application, the term "CDK4/6 inhibitor" refers to a compound that inhibits the enzyme in humans referred to cyclin-dependent kinase (CDK) 4 and/or CDK6.

The p21 gene encodes a cyclin dependent kinase inhibitor which affects cell cycle progression. Expression of p21 resulted in an accumulation of cells in G0/G1, alteration in morphology, and cell differentiation. In the present application, the term "p21 enhancer" refers to any compound that increases expression of p21. In one embodiment, the p21 enhancer is a HDAC (histone deacetylase) inhibitor.

In the present application, a HDAC inhibitor is any compound that inhibits histone deacetylase. For example, without limitation, the group examples of HDAC inhibitors include: trichostatin A (TSA), vorinostat (suberoylanilide hydroxamic acid, SAHA), entinostat, panobinostat, romidepsin, belinostat, mocetinostat, givinostat, pracinostat, chidamide, quisinostat, abexinostat, or any pharmaceutically acceptable salt thereof.

In the present application the LSD1 inhibitor is any known LSD1 inhibitor, for instance an LSD1 inhibitor as described in WO2013/057322, WO2011/131576, WO2014/086790, WO2012/135113, WO 2015/181380 and WO 2016/034946, each of which are incorporated herein by reference in their entireties.

In one embodiment, the LSD1 inhibitor may also be an antisense, an antibody, or a monoclonal antibody.

In one embodiment, the LSD1 inhibitor may also be referred to as a KDM1A inhibitor.

In one embodiment, the LSD1 inhibitor is a compound referred to herein as DDP 38003, DDP38003, DDP-38003 (CAS No. 1831167-97-5), or any pharmaceutically acceptable salt thereof. The structure of the compound referred to as DDP38003 is:

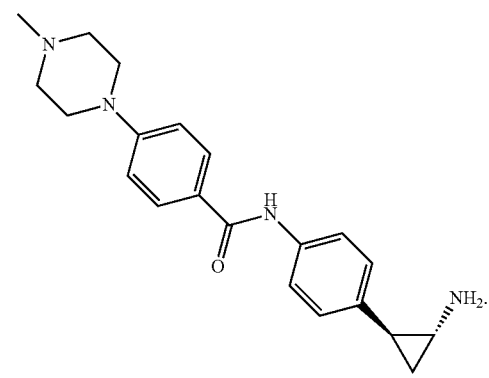 [SMILES: CN1CCN(c2ccc(C(=O)Nc3ccc([C@@H]4C[C@H]4N)cc3)cc2)CC1]

In one embodiment, the LSD1 inhibitor is a compound that is disclosed in Binda et al. in *J. Am. Chem. Soc.* 2010, 132, 6827-6833, which is incorporated by reference herein in its entirety.

In one embodiment, the LSD1 inhibitor is a compound referred to herein as MC 2580, MC2580, MC-2580, or any pharmaceutically acceptable salt thereof. The structure of the compound referred to as MC2580 is: $NH_2$.

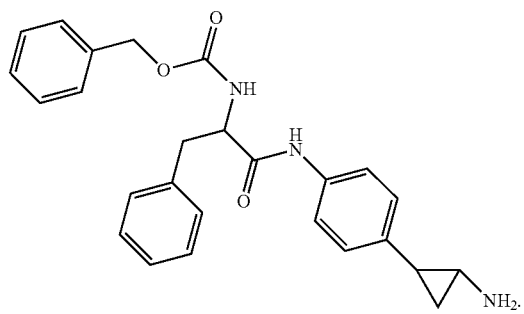 [SMILES: NC1CC1c1ccc(NC(=O)C(Cc2ccccc2)NC(=O)OCc2ccccc2)cc1]

In one embodiment the LSD1 inhibitor is selected from a compound of Formula (I)

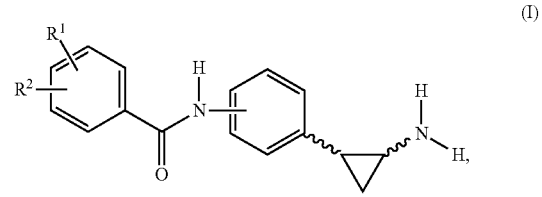

or a stereoisomer or pharmaceutically acceptable salt, solvate or prodrug thereof, wherein:

R¹ is heterocyclyl or heterocyclyl substituted by oxo, wherein the heterocyclyl is unsubstituted or substituted by one or more $C_1$-$C_6$ alkyl;

R² is hydrogen, halogen, $C_1$-$C_6$ alkyl, $C_1$-$C_6$ alkoxy, $C_1$-$C_6$ haloalkyl, $C_1$-$C_6$ haloalkoxy, or benzyloxycarbonylamino.

In one embodiment, the LSD1 inhibitor is selected from a compound of Formula (I) that is: N-[4-[trans-2-aminocyclopropyl]phenyl]-4-(4-methylpiperazin-1-yl)benzamide; N-[4-[trans-2-aminocyclopropyl]phenyl]-4-(1-methyl-4-piperidyl)benzamide; N-[4-[trans-2-aminocyclopropyl]phenyl]-3-(2-oxooxazolidin-3-yl)benzamide; N-[4-[trans-2-aminocyclopropyl]phenyl]-4-morpholino-benzamide; N-[4-[trans-2-aminocyclopropyl]phenyl]-4-(2-oxooxazolidin-3-yl)benzamide; benzyl N-[5-[[4-[(trans-2-aminocyclopropyl)phenyl]carbamoyl]-2-(4-methylpiperazin-1-yl)phenyl]carbamate; benzyl N-[4-[[4-[trans-2-aminocyclopropyl]phenyl]carbamoyl]-2-(4-methylpiperazin-1-yl)phenyl]carbamate; benzyl N-[5-[[4-[trans-2-aminocyclopropyl]phenyl]carbamoyl]-2-(1-piperidyl)phenyl]carbamate; benzyl N-[5-[[4-[trans-2-aminocyclopropyl]phenyl]carbamoyl]-2-morpholino-phenyl]carbamate; N-[4-[(1S,2R)-2-aminocyclopropyl]phenyl]-4-(4-methylpiperazin-1-yl)benzamide; N-[4-[(1S,2R)-2-aminocyclopropyl]phenyl]-3-(2-oxooxazolidin-3-yl)benzamide; N-[4-[(1R,2S)-2-aminocyclopropyl]phenyl]-4-(4-methylpiperazin-1-yl)benzamide; N-[4-[(1R,2S)-2-aminocyclopropyl]phenyl]-3-(2-oxooxazolidin-3-yl)benzamide; or a pharmaceutically acceptable salt, solvate, or prodrug thereof.

In one embodiment the LSD1 inhibitor is selected from a compound of Formula (Ia)

(Ia)

or a stereoisomer or pharmaceutically acceptable salt thereof, wherein:

A is

R is L1-R⁴;

R¹ is H, halogen, $C_1$-$C_6$-alkyl, $C_1$-$C_6$-alkoxy, —$CH_2$—Z—R⁵, or —Z—$CH_2$—R⁶;

R² and R³ are $C_1$-$C_4$-alkyl;

L1 is —$(CH_2)_j$—Y—, —Y—$(CH_2)_k$—, —$CH_2$—$CH_2$— or —CO—NH—;

j and k are, independently, each an integer from 1 to 6;

Y is oxygen, sulphur, NH or N($C_1$-$C_6$-alkyl);

Z is a bond, oxygen, sulphur, NH or N($C_1$-$C_6$-alkyl);

R⁴, R⁵, and R⁶ are, independently, $C_1$-$C_6$-alkyl, aryl, heteroaryl, wherein the aryl or heteroaryl are optionally substituted by halogen, $C_1$-$C_6$-alkyl, or L2-R⁷; or heterocyclyl, wherein the heterocyclyl is optionally substituted by $C_1$-$C_6$-alkyl;

L2 is —$(CH_2)_m$— or —$(CH_2)_n$—W—$(CH_2)_6$—;

R⁷ is $C_1$-$C_6$-alkylamino, $C_3$-$C_7$ cycloalkyl or heterocyclyl, wherein the $C_3$-$C_7$ cycloalkyl or heterocyclyl are optionally substituted by $C_1$-$C_6$-alkyl, or $NH_2$; or guanidine;

m, n, o are, independently, each zero or an integer from 1 to 6;

W is oxygen, sulphur, NH, or $CH_2$;

wherein aryl is a mono or bicyclic aromatic ring system of 6 or 9 or 10 atoms; heteroaryl is a mono or bicyclic heteroaromatic ring system of 5 to 10 members, which contains one, two, three or four heteroatoms selected from nitrogen, oxygen and sulphur, and one to nine carbon atoms;

and heterocyclyl is a mono, bicyclic or a spirocyclic saturated or partially saturated non-aromatic ring system of 4 to 12 members, which contains one, two, or three heteroatoms selected from nitrogen, oxygen, and sulphur, and three to eleven carbon atoms;

In one embodiment, the LSD1 inhibitor is selected from a compound of Formula (Ia) that is: 4-methyl-N-[2-[[4-(4-piperidyloxy)phenoxy]methyl]phenyl]thieno[3,2-b]pyrrole-5-carboxamide; 4-methyl-N-[2-[[4-(4-piperidylmethoxy)phenoxy]methyl]phenyl]thieno-[3,2-b]pyrrole-5-carboxamide; N-[2-[[4-[(1-ethyl-4-piperidyl)oxy]phenoxy]methyl]phenyl]-4-methyl-thieno[3,2-b]pyrrole-5-carboxamide; 4-methyl-N-[2-[[4-[[(3R)-pyrrolidin-3-yl]methoxy]phenoxy]methyl]phenyl]thieno[3,2-b]pyrrole-5-carboxamide; 4-methyl-N-[2-[[4-(pyrrolidin-3-ylmethoxy)phenoxy]methyl]phenyl]thieno[3,2-b]pyrrole-5-carboxamide; 4-ethyl-N-[3-[[4-(4-piperidyloxy)phenoxy]methyl]phenyl]thieno[3,2-b]pyrrole-5-carboxamide; N-[2-[[4-(azepan-4-yloxy)phenoxy]methyl]phenyl]-4-methyl-thieno[3,2-b]pyrrole-5-carboxamide; 4-ethyl-N-[2-[[4-(4-piperidyloxy)phenoxy]methyl]phenyl]thieno[3,2-b]pyrrole-5-carboxamide; N-[2-[[4-(cis-4-aminocyclohexoxy)phenoxy]methyl]phenyl]-4-methyl-thieno[3,2-b]pyrrole-5-carboxamide; 4-methyl-N-[3-[[4-(4-piperidyloxy)phenoxy]methyl]phenyl]thieno[3,2-b]pyrrole-5-carboxamide; 4-methyl-N-[2-[[4-[[(3S)-pyrrolidin-3-yl]methoxy]phenoxy]methyl]phenyl]thieno[3,2-b]pyrrole-5-carboxamide; 4-ethyl-N-[2-[[4-[(1-methyl-4-piperidyl)oxy]phenoxy]methyl]phenyl]thieno[3,2-b]pyrrole-5-carboxamide; 4-methyl-N-[2-[[4-[(1-methyl-4-piperidyl)oxy]phenoxy]methyl]phenyl]thieno[3,2-b]pyrrole-5-carboxamide; N-[2-[[4-(trans-4-aminocyclohexoxy)phenoxy]methyl]phenyl]-4-methyl-thieno[3,2-b]pyrrole-5-carboxamide; 4-methyl-N-[3-[[4-[(1-methyl-4-piperidyl)oxy]phenoxy]methyl]phenyl]thieno[3,2-b]pyrrole-5-carboxamide; 4-methyl-N-[2-[(4-pyrrolidin-3-yloxyphenoxy)methyl]phenyl]thieno[3,2-b]pyrrole-5-carboxamide; 4-methyl-N-[2-[[3-[(1-methyl-4-piperidyl)oxy]phenoxy]methyl]phenyl]thieno[³,2-b]pyrrole-5-carboxamide; 4-methyl-N-[2-[[3-(4-piperidyloxy)phenoxy]methyl]phenyl]thieno[³,2-b]pyrrole-5-carboxamide; 4-methyl-N-[3-[(1-methyl-3-piperidyl)methoxy]phenyl]thieno[3,2-b]pyrrole-5-carboxamide; 4-methyl-N-[2-[[4-[(4-methylpiperazin-1-yl)methyl]phenoxy]methyl]phenyl]thieno[3,2-b]pyrrole-5-carboxamide; 4-methyl-N-[3-(4-pyridylmethoxy)phenyl]thieno[3,2-b]pyrrole-5-carboxamide; 4-methyl-N-[3-(4-pyridyloxymethyl)phenyl]thieno[3,2-b]pyrrole-5-carboxamide; 4-methyl-N-[4-[[4-[(1-methyl-4-piperidyl)oxy]phenoxy]methyl]phenyl]thieno[3,2-b]pyrrole-5-carboxamide; N-[2-[[4-[[(1S,5R)-8-azabicyclo[3.2.1]octan-3-yl]oxy]phenoxy]methyl]phenyl]-4-methyl-thieno[3,2-b]pyrrole-5-carboxamide; N-[3-[[4-[[(1S,5R)-8-azabicyclo[3.2.1]octan-3-yl]oxy]phenoxy]methyl]phenyl]-4-methyl-thieno[3,2-b]pyrrole-5- carboxamide; 4-methyl-N-[3-[[4-(4-piperidylmethoxy)phenoxy]methyl]phenyl]thieno[3,2-b]pyrrole-5-carboxamide; 4-methyl-N-[2-[[4-(3-piperidyloxy)phenoxy]methyl]phenyl]thieno[3,2-b]pyrrole-5-carboxamide; 4-methyl-N-[3-[[4-(3-piperidyloxy)phenoxy]methyl]phenyl]thieno[3,2-b]pyrrole-5-carboxamide; N-[3-[[4-(trans-4-aminocyclohexoxy)phenoxy]methyl]phenyl]-4-methyl-thieno[3,2-b]pyrrole-5-carboxamide; N-[3-[[4-(azetidin-3-ylmethoxy)phenoxy]methyl]phenyl]-4-methyl-thieno[3,2-b]pyrrole-5-carboxamide; 4-methyl-N-[2-[[4-(3-methylaminopropoxy)phenoxy]methyl]phenyl]thieno[3,2-b]pyrrole-5-carboxamide; 4-methyl-N-[3-[(4-pyrrolidin-3-yloxyphenoxy)methyl]phenyl]thieno[3,2-b]pyrrole-5-carboxamide; N-[3-[[4-(azepan-4-yloxy)phenoxy]methyl]phenyl]-4-methyl-thieno[3,2-b]pyrrole-5-carboxamide; N-[3-[[4-(cis-4-aminocyclohexoxy)phenoxy]methyl]phenyl]-4-methyl-thieno[3,2-b]pyrrole-5-carboxamide; 4-methyl-N-[3-[[4-(pyrrolidin-3-ylmethoxy)phenoxy]methyl]phenyl]thieno[3,2-b]pyrrole-5-carboxamide; 4-methyl-N-[2-[[4-(4-piperidyloxy)phenyl]carbamoyl]phenyl]thieno[3,2-b]pyrrole-5-carboxamide; 4-methyl-N-[2-[(4-piperazin-1-ylphenoxy)methyl]phenyl]thieno[3,2-b]pyrrole-5-carboxamide; 4-methyl-N-[2-[[4-[(1-methyl-4-piperidyl)oxy]phenyl]methoxy]phenyl]thieno[3,2-b]pyrrole-5-carboxamide; 4-methyl-N-[2-[[4-(4-piperidylamino)phenoxy]methyl]phenyl]thieno[3,2-b]pyrrole-5-carboxamide; N-[2-[[4-(azetidin-3-ylmethoxy)phenoxy]methyl]phenyl]-4-methyl-thieno[3,2-b]pyrrole-5-carboxamide; N-[2-[[4-(2,8-diazaspiro[4.5]decan-2-ylmethyl)phenoxy]methyl]phenyl]-4-methyl-thieno[3,2-b]pyrrole-5-carboxamide; N-[3-(methoxymethyl)-2-[[4-[[(3R)-pyrrolidin-3-yl]methoxy]phenoxy]methyl]phenyl]-4-methyl-thieno[3,2-b]pyrrole-5-carboxamide; N-[3-(methoxymethyl)-2-[[4-(4-piperidyloxy)phenoxy]methyl]phenyl]-4-methyl-thieno[3,2-b]pyrrole-5-carboxamide; N-[2-[[4-(azepan-4-yloxy)phenoxy]methyl]-3-(methoxymethyl)phenyl]-4-methyl-thieno[3,2-b]pyrrole-5-carboxamide; N-[3-(methoxymethyl)-2-[[4-[[(3S)-pyrrolidin-3-yl]methoxy]phenoxy]methyl]phenyl]-4-methyl-thieno[3,2-b]pyrrole-5-carboxamide; N-[3-(ethoxymethyl)-2-[[4-(4-piperidyloxy)phenoxy]methyl]phenyl]-4-methyl-thieno[3,2-b]pyrrole-5-carboxamide; N-[3-(isopropoxymethyl)-2-[[4-(4-piperidyloxy)phenoxy]methyl]phenyl]-4-methyl-thieno[3,2-b]pyrrole-5-carboxamide; N-[3-(ethoxymethyl)-2-[[4-[[(3R)-pyrrolidin-3-yl]methoxy]phenoxy]methyl]phenyl]-4-methyl-thieno[3,2-b]pyrrole-5-carboxamide; 4-ethyl-N-[3-(methoxymethyl)-2-[[4-[[(3R)-pyrrolidin-3-yl]methoxy]phenoxy]methyl]phenyl]thieno[3,2-b]pyrrole-5-carboxamide; 4-methyl-N-[3-(morpholinomethyl)-2-[[4-(4-piperidyloxy)phenoxy]methyl]phenyl]thieno[3,2-b]pyrrole-5-carboxamide; 4-methyl-N-[5-methyl-2-[[4-(pyrrolidin-3-ylmethoxy)phenoxy]methyl]phenyl]thieno[3,2-b]pyrrole-5-carboxamide; 4-methyl-N-[2-[[5-(4-piperidyloxy)-2-pyridyl]oxymethyl]phenyl]thieno[3,2-b]pyrrole-5-carboxamide; 4-methyl-N-[2-(4-piperidylmethoxy)phenyl]thieno[3,2-b]pyrrole-5-carboxamide; 4-methyl-N-[3-[[3-(4-piperidyloxy)phenoxy]methyl]phenyl]thieno[3,2-b]pyrrole-5-carboxamide; N-[3-[[4-(guanidinomethyl)phenoxy]methyl]phenyl]-4-methyl-thieno[3,2-b]pyrrole-5-carboxamide; N-[2-[[4-(guanidinomethyl)phenoxy]methyl]phenyl]-4-methyl-thieno[3,2-b]pyrrole-5-carboxamide; 4-methyl-N-[2-[2-[4-(4-piperidyloxy)phenyl]ethyl]phenyl]thieno[3,2-b]pyrrole-5-carboxamide; 4-methyl-N-[3-[2-[4-(4-piperidyloxy)phenyl]ethyl]phenyl]thieno[3,2-b]pyrrole-5-carboxamide; 4-methyl-N-[2-[[4-(4-piperidyloxy)anilino]methyl]phenyl]thieno[3,2-b]pyrrole-5-carboxamide; 6-methyl-N-[2-[[3-(4-piperidyloxy)phenoxy]methyl]phenyl]thieno[2,3-b]pyrrole-5-carboxamide; 6-ethyl-N-[2-[[3-(4-piperidyloxy)phenoxy]methyl]phenyl]thieno[2,3-b]pyrrole-5-carboxamide; 6-ethyl-N-[2-[[4-(4-piperidyloxy)phenoxy]methyl]phenyl]thieno[2,3-b]pyrrole-5-carboxamide; 6-methyl-N-[2-[[4-(4-piperidyloxy)phenoxy]methyl]phenyl]thieno[2,3-b]pyrrole-5-carboxamide; 6-methyl-N-[2-[[4-(pyrrolidin-3-ylmethoxy)phenoxy]methyl]phenyl]thieno[2,3-b]pyrrole-5-carboxamide; 4-methyl-N-[4-[[4-(4-piperidyloxy)phenyl]carbamoyl]-2-pyridyl]thieno[3,2-b]pyrrole-5-carboxamide; or a stereoisomer or pharmaceutically acceptable salt thereof.

In one embodiment, the LSD1 inhibitor is selected from a compound of Formula (II)

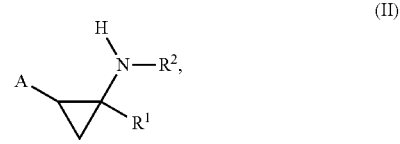

wherein:
A is aryl or heteroaryl, wherein the aryl or heteroaryl may be optionally substituted by one or more substituents independently selected from the group consisting of halogen, $C_1$-$C_6$ alkyl, $C_1$-$C_6$ alkoxy, $C_1$-$C_6$ haloalkyl, $C_1$-$C_6$ haloalkoxy, CN, nitro, $NH_2$, azide, OH, $C_1$-$C_6$ alkylamino, and R-L-;

R is aryl, wherein the aryl may be optionally substituted by one, two or more substituents independently selected from the group consisting of halogen, $C_1$-$C_6$ alkyl, $C_1$-$C_6$ alkoxy, $C_1$-$C_6$ haloalkyl, $C_1$-$C_6$ haloalkoxy, CN, nitro, $NH_2$, azide, $C_1$-$C_6$ alkylamino optionally substituted by OH, heterocyclylamino optionally substituted by $C_1$-$C_6$ alkyl, OH, phenyl, heterocyclyl optionally substituted by $C_1$-$C_6$ alkyl, heterocyclyl substituted by oxo, heteroaryl, and benzyloxycarbonylamino; or heteroaryl;

L is a single bond; $C_1$-$C_6$ alkylene; $C_2$-$C_6$ alkenylene; —$(CH_2)_m$X—$(CH_2)_r$—; —$(CH_2)$O$(SO_2)$NH—; —$(CH_2)_p$(CO)$NR^3$—; —$(CH_2)_q$$NR^4$(CO)—; heterocyclyl substituted by oxo; or heteroaryl;

$R^1$ is $C_1$-$C_6$ alkyl, optionally substituted by aryl or heteroaryl; aryl; heteroaryl; or —$(CH_2)_r$—Y—$R^5$;

and wherein the aryl or heteroaryl group may be optionally substituted by one or more substituents independently selected from the group consisting of halogen, $C_1$-$C_6$ alkyl, $C_1$-$C_6$ alkoxy, $C_1$-$C_6$ haloalkyl, $C_1$-$C_6$ haloalkoxy, nitro, acetamido, and phenyl;

$R^2$ is hydrogen; $C_1$-$C_6$ alkyl, optionally substituted by aryl, heteroaryl, or by heterocyclyl and wherein the aryl or heteroaryl may be optionally substituted by one or more substituents independently selected from the group consisting of halogen, $C_1$-$C_6$ alkyl, $C_1$-$C_6$ alkoxy, $C_1$-$C_6$ haloalkyl, $C_1$-$C_6$ haloalkoxy, and $NH_2$; or —$CH_2$(CO)$NR^6R^7$;

m, n, o, p, q are, independently, zero or an integer from 1 to 6;

r is an integer from 1 to 6;

X and Y are, independently, $NR^8$; O; or S;

$R^3$ and $R^4$ are, independently, hydrogen; or $C_1$-$C_6$ alkyl;

$R^5$ is hydrogen, aryl or heteroaryl, wherein the aryl or heteroaryl may be optionally substituted by one or more independently selected from the group consisting of halogen, $C_1$-$C_6$ alkyl, $C_1$-$C_6$ alkoxy, $C_1$-$C_6$ haloalkyl, $C_1$-$C_6$ haloalkoxy, and phenyl;

$R^6$ and $R^7$ are, independently, hydrogen; $C_1$-$C_6$ alkyl; or $R^6$ and $R^7$ together with the nitrogen to which they are bound form a $C_4$-$C_{10}$-heterocyclic ring, optionally containing one or more further heteroatoms in the ring independently selected from $NR^9$, O or S and being optionally substituted by $NH_2$;

$R^8$ is hydrogen; $C_1$-$C_6$ alkyl, optionally substituted by aryl or heterocyclyl; or $C_{3-4}$ cycloalkyl;

$R^9$ is hydrogen or $C_1$-$C_6$ alkyl;

or stereoisomers or pharmaceutically acceptable salts thereof.

In one embodiment, the LSD1 inhibitor is selected from a compound of Formula (II) that is: (1S,2R)-1-ethyl-2-phenyl-cyclopropanamine; (1R,2S)-1-ethyl-2-phenyl-cyclopropanamine; trans-1-methyl-2-phenyl-cyclopropanamine; (1R,2S)-1-methyl-2-phenyl-cyclopropanamine; (1S,2R)-1-methyl-2-phenyl-cyclopropanamine; trans-1-propyl-2-phenyl-cyclopropanamine; trans-1-isopropyl-2-phenyl-cyclopropanamine; trans-1-benzyl-2-phenyl-cyclopropanamine; (1S,2S)-1-benzyl-2-phenyl-cyclopropanamine; (1R,2R)-1-benzyl-2-phenyl-cyclopropanamine; trans-1-phenethyl-2-phenyl-cyclopropanamine; trans-2-(4-bromophenyl)-1-ethyl-cyclopropanamine; trans-1-benzyl-2-(4-bromophenyl) cyclopropanamine; trans-1-ethyl-2-(6-quinolyl) cyclopropanamine; trans-1-(2-naphthylmethyl)-2-phenyl-cyclopropanamine; trans-1-ethyl-2-(4-fluorophenyl) cyclopropanamine; trans-1-ethyl-2-(4-chlorophenyl) cyclopropanamine; trans-1-ethyl-2-[3-(trifluoromethyl) phenyl]cyclopropanamine; trans-1-ethyl-2-[4-(trifluormethyl)phenyl]cyclopropanamine; trans-1-ethyl-2-(3-fluorophenyl)cyclopropanamine; trans-1-ethyl-2-(3-chlorophenyl)-cyclopropanamine; trans-1-ethyl-2-(3-bromophenyl)-cyclopropanamine; trans-1-ethyl-2-[3-methoxyphenyl]cyclopropanamine; 1-ethyl-(trans)-2-[4-(trifluoromethoxy)phenyl]cyclopropanamine; trans-1-ethyl-2-(2-fluorophenyl)cyclopropanamine; trans-1-ethyl-2-(2-chlorophenyl)-cyclopropanamine; trans-1-ethyl-2-(2-bromophenyl)-cyclopropanamine; trans-1-(1-naphthylmethyl)-2-phenyl-cyclopropanamine; trans-2-(4-bromophenyl)-1-(2-naphthylmethyl)cyclopropanamine; trans-N-[4-[2-amino-2-ethyl-cyclopropyl]phenyl]naphthalene-2-carboxamide; N-[2-[(trans)-2-amino-2-ethyl-cyclopropyl]phenyl]benzamide; benzyl N-[3-[[2-[(trans)-2-amino-2-ethyl-cyclopropyl]phenyl]carbamoyl]phenyl] carba-mate; benzyl N-[3-[[3-[(trans)-2-amino-2-ethyl-cyclopropyl]phenyl]carbamoyl]phenyl]carba-mate; N-[4-[(trans)-2-amino-2-ethyl-cyclopropyl]phenyl]-3-chloro-benzamide N-[4-[(trans)-2-amino-2-ethyl-cyclopropyl] phenyl]-3-phenyl-benzamide; N-[4-[(trans)-2-amino-2-ethyl-cyclopropyl]phenyl]-4-phenyl-benzamide; benzyl N-[3-[[4-[(trans)-2-amino-2-ethyl-cyclopropyl]phenyl]carbamoyl]phenyl]carba-mate; N-[4-[[4-[(trans)-2-amino-2-ethyl-cyclopropyl]phenyl]carbamoyl]phenyl]carba-mate; N-[4-[(trans)-2-amino-2-ethyl-cyclopropyl]phenyl]-2-phenyl-acetamide; N-[4-[(trans)-2-amino-2-ethyl-cyclopropyl] phenyl]-3-phenyl-propanamide; 2-(4-benzyloxyphenyl)-trans-1-ethyl-cyclopropanamine; N-[4-[(2-amino-trans-2-ethyl-cyclopropyl]phenyl]benzenesulfonamide; trans-1-benzyl-2-(4-benzyloxyphenyl)cyclopropanamine; N-[4-[trans-2-amino-2-(2-naphthylmethyl)cyclopropyl]phenyl] benzamide; benzyl-N-[3-[[4-[(trans)-2-amino-2-(2-naphthylmethyl)cyclopropyl]phenyl]carbamoyl]phenyl] carbamate; N-[4-[(trans)-2-amino-2-(2-naphthylmethyl) cyclopropyl]phenyl]-2-phenyl-acetamide; N-[4-[trans-2-amino-2-ethyl-cyclopropyl]phenyl]benzamide; trans-4-(2-amino-2-ethyl-cyclopropyl)aniline; trans-2-(3-azidophenyl)-1-ethyl-cyclopropanamine; 1-amino-(trans)-2-phenyl-cyclopropyl]methanol; 1-amino-(cis)-2-phenyl-cyclopropyl]methanol; (1R,2S)-1-ethyl-N-[(2-methoxyphenyl)methyl]-2-phenyl-cyclopropanamine; (1R, 2S)-1-ethyl-N-[(2-methoxy-1-naphthyl)methyl]-2-phenyl-cyclopropanamine; 2-[[(1S,2R)-1-methyl-2-phenyl-cyclopropyl]amino]-1-(4-methylpiperazin-1-yl)ethanone; 2-[[(1S,2S)-1-methyl-2-phenyl-cyclopropyl]amino]-1-(4-methylpiperazin-1-yl)ethanone; 1-[(3S)-3-aminopyrrolidin-1-yl]-2-[[(1S,2R)-1-methyl-2-phenyl-cyclopropyl]amino] ethanone; trans-2-[[(1-ethyl-2-phenyl-cyclopropyl]amino]-1-(4-methylpiperazin-1-yl)ethanone; cis-2-[[(1-ethyl-2-phenyl-cyclopropyl]amino]-1-(4-methylpiperazin-1-yl) ethanone; trans-1-ethyl-N-methyl-2-phenyl-cyclopropanamine; cis-1-ethyl-N-methyl-2-phenyl-cyclopropanamine; trans-1-ethyl-N-ethyl-2-phenyl-cyclopropanamine; cis-1-ethyl-N-ethyl-2-phenyl-cyclopropanamine; trans-2-[[1-ethyl-2-phenyl-cyclopropyl] amino]acetamide; trans-N-benzyl-1-ethyl-2-phenyl-cyclopropanamine; trans-N-[(3,4-dimethoxyphenyl) methyl]-1-ethyl-2-phenyl-cyclopropanamine; trans-N-[(4,7-dimethoxy-1-naphthyl)methyl]-1-ethyl-2-phenyl-cyclopropanamine; trans-N-[(2-chloro-3-pyridyl)methyl]-1-ethyl-2-phenyl-cyclopropanamine; trans-N-[(2,2-dimethylchroman-6-yl)methyl]-1-ethyl-2-phenyl-cyclopropanamine; cis-1,2-diphenylcyclopropanamine; trans-1,2-diphenylcyclopropanamine; trans-1-ethyl-2-phenyl-cyclopropanamine; trans-2-(4-bromo-3-fluoro-phenyl)-1-ethyl-cyclopropanamine; trans 2-(3-bromophenyl)-1-phenethyl-cyclopropanamine; (1R,2S)-1,2-diphenylcyclopropanamine; (1S,2R)-1,2-diphenylcyclopropanamine; trans-2-(4-fluorophenyl)-1-(2-naphthylmethyl)cyclopropanamine; trans-2-(4-chlorophenyl)-1-(2-naphthylmethyl)cyclopropanamine; trans-2-(3-chlorophenyl)-1-(2-naphthylmethyl)cyclopropanamine; trans-2-(3-bromophenyl)-1-(2-naphthylmethyl) cyclopropanamine; trans-2-(4-chlorophenyl)-1-phenethyl-cyclopropanamine; trans-2-(4-fluorophenyl)-1-phenethyl-cyclopropanamine; trans-1-benzyl-2-(4-fluorophenyl) cyclopropanamine; trans-1-benzyl-2-(4-chlorophenyl) cyclopropanamine; trans 2-(4-bromophenyl)-1-phenethyl-cyclopropanamine; cis-1-ethyl-2-phenyl-cyclopropanamine; N-[4-(trans-2-amino-2-ethyl-cyclopropyl)phenyl]-3-[(1-methyl-4-piperidyl)amino]-4-phenyl-benzamide; 2-(4-benzyloxyphenyl)-1-(2-naphthylmethyl)cyclopropanamine; N-[4-trans-[2-amino-2-ethyl-cyclopropyl]phenyl]-2-(1-naphthyl)acetamide; N-[4-trans-[2-amino-2-ethyl-cyclopropyl]phenyl]-2-(4-nitrophenyl)acetamide; benzyl N-[4-[[4-[trans-2-amino-2-(2-naphthylmethyl)cyclopropyl]phenyl]carbamoyl] phenyl] carbamate; N-[4-(trans-2-amino-2-ethyl-cyclopropyl) phenyl]naphthalene-1-carboxamide; N-[4-[trans-2-amino-2-(2-naphthylmethyl)cyclopropyl]phenyl]naphthalene-2-carboxamide; N-[4-[trans-2-amino-2-(2-naphthylmethyl) cyclopropyl]phenyl]-4-phenyl-benzamide; N-[4-trans-2-amino-2-ethyl-cyclopropyl]phenyl]-2-(2-naphthyl) acetamide; N-[4-[trans-2-amino-2-phenyl-cyclopropyl] phenyl]benzamide; N-[4-[trans-2-amino-2-(2-naphthylmethyl)cyclopropyl]phenyl]-2-(1-naphthyl) acetamide; N-[3-[trans-2-amino-2-ethyl-cyclopropyl] phenyl]-2-(1-naphthyl)acetamide; N-[4-[trans-2-amino-2-ethyl-cyclopropyl]phenyl]-4-(3-furyl)benzamide; N-[4-[trans-2-amino-2-(2-naphthylmethyl)cyclopropyl]phenyl]-3-chloro-benzamide; N-[3-[trans-2-amino-2-ethyl-cyclopropyl]phenyl]-3-chloro-benzamide; N-[4-[trans-2-amino-2-(2-naphthylmethyl)cyclopropyl]phenyl]-3-phenylpropanamide; N-[4-[trans-2-amino-2-(2-naphthylmethyl)cyclopropyl]phenyl]-3-phenyl-benzamide; N-[4-[trans-2-amino-2-ethyl-cyclopropyl]phenyl]-4-(2-oxooxazolidin-3-yl)benzamide; benzyl N-[3-[(4-[trans-2-amino-2-phenyl-cyclopropyl]phenyl)carbamoyl]phenyl] carbamate; N-[4-[trans-2-amino-2-phenyl-cyclopropyl]phenyl]naphthalene-2-carboxamide; N-[4-[trans-2-amino-2-ethyl-cyclopropyl]-2-fluoro-phenyl]benzamide; N-[4-[trans-2-amino-2-ethyl-cyclopropyl]-2-fluoro-phenyl]-4-phenyl-benzamide; N-[4-[trans-2-amino-2-ethyl-cyclopropyl]phenyl]-4-morpholino-benzamide; N-[4-[trans-2-amino-2-phenyl-cyclopropyl]phenyl]-4-phenyl-benzamide; N-[4-[trans-2-amino-2-phenyl-cyclopropyl]phenyl]naphthalene-1-carboxamide; N-[3-[trans-2-amino-2-ethyl-cyclopropyl]phenyl]-4-phenyl-benzamide; N-[3-[trans-2-amino-2-ethyl-cyclopropyl]phenyl]naphthalene-2-carboxamide; N-[3-[trans-2-amino-2-ethyl-cyclopropyl]phenyl]benzamide; N-[4-[trans-2-amino-2-ethyl-cyclopropyl]-2-fluoro-phenyl]-2-(1-naphthyl)acetamide; benzyl N-[4-[[4-[trans-2-amino-2-ethyl-cyclopropyl]-2-fluoro-phenyl]carbamoyl]phenyl] carbamate; N-[4-[trans-2-amino-2-ethyl-cyclopropyl]-2-fluoro-phenyl]-4-(4-methylpiperazin-1-yl)benzamide; N-[4-[trans-2-amino-2-ethyl-cyclopropyl]phenyl]-4-(4-methylpiperazin-1-yl)benzamide; N-[4-[trans-2-amino-2-ethyl-cyclopropyl]phenyl]-3-(2-oxooxazolidin-3-yl)benzamide; benzyl N-[5-[[4-[trans-2-amino-2-ethyl-cyclopropyl]phenyl]carbamoyl]-2-morpholino-phenyl]carbamate; N-[4-[trans-2-amino-2-ethyl-cyclopropyl]phenyl]-4-(1-methyl-4-piperidyl)benzamide; N-[4-(trans-2-amino-2-ethyl-cyclopropyl)phenyl]pyridine-4-carboxamide; N-[4-(trans-2-amino-2-ethyl-cyclopropyl]phenyl)-4-(4-pyridyl)benzamide; N-[4-(trans-2-amino-2-phenyl-cyclopropyl]phenyl]-3-chloro-benzamide; N-[4-(trans-2-amino-2-phenyl-cyclopropyl)phenyl]-2-(1-naphthyl)acetamide; N-[4-(trans-2-amino-2-phenyl-cyclopropyl)phenyl]-2-phenyl-acetamide; N-[4-(trans-2-amino-2-phenyl-cyclopropyl)phenyl]-3-phenyl-benzamide; N-[4-(trans-2-amino-2-phenyl-cyclopropyl)phenyl]-2-(2-naphthyl)acetamide; N-[4-(trans-2-amino-2-phenyl-cyclopropyl)phenyl]pyridine-4-carboxamide; N-[4-(trans-2-amino-2-phenyl-cyclopropyl]phenyl)-4-(1-methyl-4-piperidyl)benzamide; N-[4-(trans-2-amino-2-phenyl-cyclopropyl)phenyl]-4-(4-methylpiperazin-1-yl)benzamide; N-[4-(trans-2-amino-2-phenyl-cyclopropyl)phenyl]-3-(2-oxooxazolidin-3-yl)benzamide; N-[4-(trans-2-amino-2-phenethyl-cyclopropyl)phenyl]pyridine-4-carboxamide; N-[4-(trans-2-amino-2-phenethyl-cyclopropyl)phenyl]-4-phenyl-benzamide; N-[4-trans-2-amino-2-phenethyl-cyclopropyl)phenyl]benzamide; N-[4-(trans-2-amino-2-phenethyl-cyclopropyl)phenyl]-4-(1-methyl-4-piperidyl)benzamide; N-[4-(trans-2-amino-2-phenethyl-cyclopropyl)phenyl]-4-(4-methylpiperazin-1-yl)benzamide; benzyl N-[5-[[4-[trans-2-amino-2-ethyl-cyclopropyl]phenyl]carbamoyl]-2-(4-methylpiperazin-1-yl)phenyl]carbamate; N-[4-(trans-2-amino-2-phenethyl-cyclopropyl)phenyl]-3-(2-oxooxazolidin-3-yl)benzamide; 4-[trans-2-amino-2-(2-naphthylmethyl)cyclopropyl]aniline; N-[4-(trans-2-amino-2-ethyl-cyclopropyl)phenyl]-4-(2-hydroxyethylamino)benzamide; benzyl N-[3-[1-[4-[2-amino-2-ethyl-cyclopropyl]phenyl]triazol-4-yl]phenyl]carbamate; trans-1-ethyl-2-[3-(4-phenyltriazol-1-yl)phenyl]cyclopropanamine; benzyl N-[3-[1-[4-[2-amino-2-(2-naphthylmethyl)cyclopropyl]phenyl]triazol-4-yl]phenyl]carbamate; trans-1-(2-naphthylmethyl)-2-[4-(4-phenyltriazol-1-yl)phenyl]cyclopropanamine; trans 1-ethyl-2-[2-(4-phenyltriazol-1-yl)phenyl]cyclopropanamine; trans-1-benzyl-2-[4-(4-phenyltriazol-1-yl)phenyl]cyclopropanamine; N-[4-[(1S,2R)-2-amino-2-ethyl-cyclopropyl]phenyl]-4-phenyl-benzamide; N-[4-[(1R,2S)-2-amino-2-ethyl-cyclopropyl]phenyl]-4-phenyl-benzamide; trans 1-benzyl-2-(3-methoxyphenyl)cyclopropanamine; 1-[3-[(trans-2-amino-2-ethyl-cyclopropyl]phenyl]-3-phenyl-imidazolidin-2-one; trans-1-ethyl-2-[4-(4-phenyltriazol-1-yl)phenyl]cyclopropanamine; trans 1-[(benzylamino)methyl]-2-phenyl-cyclopropanamine; trans 1-[(cyclopropylamino)methyl]-2-phenyl-cyclopropanamine; trans 1-[(4-methylpiperazin-1-yl)methyl]-2-phenyl-cyclopropanamine; 5-[[[trans-1-methyl-2-phenyl-cyclopropyl]amino]methyl]pyrimidin-2-amine; trans-N-[(2-methoxy-3-pyridyl)methyl]-1-methyl-2-phenyl-cyclopropanamine; trans-N-(2,3-dihydro-1,4-benzodioxin-6-ylmethyl)-1-methyl-2-phenyl-cyclopropanamine; cis-N,1-dimethyl-2-phenyl-cyclopropanamine; 2-[[trans-1,2-diphenylcyclopropyl]amino]-1-(4-methylpiperazin-1-yl)ethanone; 1-(4-methylpiperazin-1-yl)-2-[[trans-1-(2-naphthylmethyl)-2-phenyl-cyclopropyl]amino]ethanone; 2-[[(1R,2S)-1-methyl-2-phenyl-cyclopropyl]amino]-1-(4-methylpiperazin-1-yl)ethanone; 2-[[(1R,2R)-1-methyl-2-phenyl-cyclopropyl]amino]-1-(4-methylpiperazin-1-yl)ethanone; 2-[[trans-1-methyl-2-phenyl-cyclopropyl]amino]-1-(4-methylpiperazin-1-yl)ethanone; 2-[[cis-1-methyl-2-phenyl-cyclopropyl]amino]-1-(4-methylpiperazin-1-yl)ethanone; trans-N,1-dimethyl-2-phenyl-cyclopropanamine; 2-[[trans-1-ethyl-2-phenyl-cyclopropyl]amino]-1-(1-piperidyl)ethanone; trans-1-ethyl-2-phenyl-N-[2-(1-piperidyl)ethyl]cyclopropanamine; 5-[[[trans-1-methyl-2-phenyl-cyclopropyl]amino]methyl]-1,3,4-oxadiazol-2-amine; trans-1-(4-nitrophenyl)-2-phenyl-cyclopropanamine; trans-2-(4-chlorophenyl)-1-phenyl-cyclopropanamine; trans-2-(4-bromophenyl)-1-phenyl-cyclopropanamine; N-[4-(trans-1-amino-2-phenyl-cyclopropyl]phenyl]acetamide; or a stereoisomer or pharmaceutically acceptable salt thereof.

In one embodiment, the LSD1 inhibitor is selected from a compound of Formula (III)

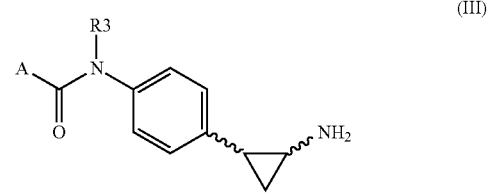

(III)

or an isomer, tautomer, racemic form, enantiomer, diastereomer, epimer, polymorph, solvate, mixtures thereof, pharmaceutically acceptable salt thereof, wherein:

A is R or $CH(R_1)$—NH—CO—$R_2$;

R and $R^2$ are selected from: alkyl, alkenyl, alkynyl, cycloalkyl, aryl, heteroaryl, heterocycloalkyl, cycloalkylalkyloxy, arylalkyloxy, heteroarylalkyloxy, heterocycloalkylalkyloxy, cycloalkylalkyl, arylalkyl, heteroarylalkyl, heterocycloalkylalkyl, cycloalkylalkylamino, arylalkylamino, heteroarylalkylamino, heterocycloalkylalkylamino;

$R_1$ is selected from: alkyl, alkenyl, alkynyl, cycloalkyl, aryl, heteroaryl, heterocycloalkyl, cycloalkylalkyl, arylalkyl, heteroarylalkyl, heterocycloalkylalkyl;

$R_3$ is H, $C_1$-$C_6$ alkyl.

In one embodiment, the LSD1 inhibitor is selected from a compound of Formula (III) that is: trans benzyl 4-(2-aminocyclopropyl)phenylcarbamate; trans N-(4-(2-aminocyclopropyl)phenyl)benzamide; trans N-(4-(2-aminocyclopropyl)phenyl)-1-naphthamide; trans N-(4-(2-aminocyclopropyl)phenyl)-2-naphthamide; trans N-(4-(2- aminocyclopropyl)phenyl)biphenyl-4-carboxamide; trans N-(4-(2-aminocyclopropyl)phenyl)-2-phenylacetamide; trans N-(4-(2-aminocyclopropyl)phenyl)-2-(naphthalen-1-yl)acetamide; trans N-(4-(2-aminocyclopropyl)phenyl)-2-(naphthalen-2-yl)acetamide; trans benzyl 1-(4-(2-aminocyclopropyl)phenylamino)-3-methyl-1-oxobutan-2-ylcarbamate; trans benzyl 1-(4-(2-aminocyclopropyl)phenylamino)-4-methyl-1-oxopentan-2-ylcarbamate; trans benzyl 1-(4-(2-aminocyclopropyl)phenylamino)-3-cyclohexyl-1-oxopropan-2-ylcarbamate; trans benzyl 2-(4-(2-aminocyclopropyl)phenylamino)-2-oxo-1-phenylethylcarbamate; trans benzyl 1-(4-(2-aminocyclopropyl)phenylamino)-1-oxo-3-phenylpropan-2-ylcarbamate; trans benzyl 1-(4-(2-aminocyclopropyl)phenylamino)-3-(4-bromophenyl)-1-oxopropan-2-ylcarbamate; trans benzyl 1-(4-(2-aminocyclopropyl)phenylamino)-3-(4-methoxyphenyl)-1-oxopropan-2-ylcarbamate; trans benzyl 1-(4-(2-aminocyclopropyl)phenylamino)-1-oxo-4-phenylbutan-2-ylcarbamate; trans benzyl 1-(4-(2-aminocyclopropyl)phenylamino)-1-oxo-3,3-diphenylpropan-2-ylcarbamate; trans benzyl 1-(4-(2-aminocyclopropyl)phenylamino)-3-(naphthalen-1-yl)-1-oxopropan-2-ylcarbamate; trans benzyl 1-(4-(2-aminocyclopropyl)phenylamino)-3-(naphthalen-2-yl)-1-oxopropan-2-ylcarbamate; trans benzyl 1-(4-(2-aminocyclopropyl)phenylamino)-4-(1H-indol-3-yl)-1-oxobutan-2-ylcarbamate; trans benzyl 1-(4-(2-aminocyclopropyl)phenylamino)-4-(benzo[b]thiophen-3-yl)-1-oxobutan-2-ylcarbamate; trans 4-bromobenzyl 1-(4-(2-aminocyclopropyl)phenylamino)-1-oxo-3-phenylpropan-2-ylcarbamate; cis benzyl 1-(4-(2-aminocyclopropyl)phenylamino)-1-oxo-3-phenylpropan-2-ylcarbamate; trans N1-(4-(2-aminocyclopropyl)phenyl)-N8-hydroxyoctanediamide; trans benzyl 1-((4-(2-aminocyclopropyl)phenylXmethyl)amino)-1-oxo-3-phenylpropan-2-ylcarbamate; trans N-(4-(2-aminocyclopropyl)phenyl)-2-(3-benzylureido)-3-phenylpropanamide or a isomer, tautomer, racemic form, enantiomer, diastereomer, epimer, polymorph, solvate, mixtures thereof, pharmaceutically acceptable salt thereof.

In one embodiment, the LSD1 inhibitor is selected from: N1-((trans)-2-phenylcyclopropyl)cyclohexane-1,4-diamine; (cis)-N1-((1S,2R)-2-phenylcyclopropyl)cyclohexane-1,4-diamine; (trans)-N1-((1S,2R)-2-phenylcyclopropyl)cyclohexane-1,4-diamine; (cis)-N1-((1R,2S)-2-phenylcyclopropyl)cyclohexane-1,4-diamine; (trans)-N1-((1R,2S)-2-phenylcyclopropyl)cyclohexane-1,4-diamine; N1-((trans)-2-(thiazol-5-yl)cyclopropyl)cyclohexane-1,4-diamine; 1-((trans)-2-(pyridin-3-yl)cyclopropyl)cyclohexane-1,4-diamine; N1-((trans)-2-(6-(3-(trifluoromethyl)phenyl)pyridin-3-yl)cyclopropyl)cyclohexane-1,4-diamine; N1-((trans)-2-(3'-(trifluoromethyl)-[1,1'-biphenyl]-4-yl)cyclopropyl)cyclohexane-1,4-diamine; N1-((trans)-2-(4-(benzyloxy)phenyl)cyclopropyl)cyclohexane-1,4-diamine; 4-(((trans)-2-(6-(3-(trifluoromethyl)phenyl)pyridin-3-yl)cyclopropyl)amino)cyclohexanol; 4-(((trans)-2-(6-(3-(trifluoromethyl)phenyl)pyridin-3-yl)cyclopropyl)amino)cyclohexanecarboxamide; N-(4-(((trans)-2-(6-(3-(trifluoromethyl)phenyl)pyridin-3-yl)cyclopropyl)amino)cyclohexyl)acetamide; (4-(((trans)-2-(6-(3-(trifluoromethyl)phenyl)pyridin-3-yl; (R)-1-(4-(((trans)-2-phenylcyclopropyl)amino)cyclohexyl)pyrrolidin-3-amine; N1-((trans)-2-(4'-chloro-[1,1'-biphenyl]-4-yl)cyclopropyl)cyclohexane-1,4-diamine; N1-((trans)-2-(3'-chloro-[1,1'-biphenyl]-4-yl)cyclopropyl)cyclohexane-1,4-diamine; 4'-((trans)-2-((4-aminocyclohexyl)amino)cyclopropyl)-[1,1'-biphenyl]-3-ol; N-(4'-((trans)-2-((4-aminocyclohexyl)amino)-[1,1'-biphenyl]-3-yl)methanesulfonamide; N1-((trans)-2-(4-((2-fluorobenzyl)oxy)phenyl)cyclopropyl)cyclohexane-1,4-diamine; N1-((trans)-2-(4-((3-fluorobenzyl)oxy)phenyl)cyclopropyl)cyclohexane-1,4-diamine; N1-((trans)-2-(4-((4-fluorobenzyl)oxy)phenyl)cyclopropyl)cyclohexane-1,4-diamine; N1-methyl-N4-((trans)-2-phenylcyclopropyl)cyclohexane-1,4-diamine; N1-methyl-N4-((trans)-2-(3'-(trifluoromethyl)-[1,1'-biphenyl]-4-yl)cyclopropyl)cyclohexane-1,4-diamine; N1-((trans)-2-(4-(benzyloxy)phenyl)cyclopropyl)-N4-methylcyclohexane-1,4-diamine; N1-((trans)-2-phenylcyclopropyl)cyclobutane-1,3-diamine; N1-((trans)-2-(3'-(trifluoromethyl)-[1,1'-biphenyl]-4-yl)cyclopropyl)cyclobutane-1,3-diamine; N1-((trans)-2-(4-(benzyloxy)phenyl)cyclopropyl)cyclobutane-1,3-diamine; N1-((trans)-2-phenylcyclopropyl)-2,3-dihydro-1H-indene-1,3-diamine; N1-((trans)-2-(3'-(trifluoromethyl)-[1,1'-biphenyl]-4-yl)cyclopropyl)-2,3-dihydro-1H-indene-1,3-diamine; N1-((trans)-2-(4-(benzyloxy)phenyl)cyclopropyl)-2,3-dihydro-1H-indene-1,3-diamine; N1-((trans)-2-fluoro-2-phenylcyclopropyl)cyclohexane-1,4-diamine; N1-((1S,2S)-2-fluoro-2-phenylcyclopropyl)cyclohexane-1,4-diamine; N1-((1R,2R)-2-fluoro-2-phenylcyclopropyl)cyclohexane-1,4-diamine; 1-methyl-N4-((trans)-2-phenylcyclopropyl)cyclohexane-1,4-diamine; 4-(aminomethyl)-N-((trans)-2-phenylcyclopropyl)cyclohexanamine; N1-((trans)-2-phenylcyclopropyl)cyclohexane-1,3-diamine; N1-((cis)-2-phenylcyclopropyl)cyclohexane-1,4-diamine; tert-butyl (4-(((trans)-2-phenylcyclopropyl)amino)cyclohexyl)carbamate; 1-ethyl-3-(4-(((trans)-2-phenylcyclopropyl)amino)cyclohexyl)urea; 4-morpholino-N-((trans)-2-phenylcyclopropyl)cyclohexanamine; N1-((trans)-2-(4-bromophenyl)cyclopropyl)cyclohexane-1,4-diamine; N1-{2-(o-tolyl)cyclopropyl)cyclohexane-1,4-diamine; N1-(2-(4-(trifluoromethyl)phenyl)cyclopropyl)cyclohexane-1,4-diamine; N1-(2-(4-methoxyphenyl)cyclopropyl)cyclohexane-1,4-diamine; 4-(2-((4-aminocyclohexyl)amino)cyclopropyl)phenol; N1-(2-(2-fluorophenyl)cyclopropyl)cyclohexane-1,4-diamine; N1-(2-(3,4-difluorophenyl)cyclopropyl)cyclohexane-1,4-diamine; N1-(2-(naphthalen-2-yl)cyclopropyl)cyclohexane-1,4-diamine; N1-(2-methyl-2-phenylcyclopropyl)cyclohexane-1,4-diamine; (R)-1-(4-(((trans)-2-(3'-(trifluoromethyl)-[1,1'-biphenyl]-4-ylcyclopropyl)amino)cyclohexyl)pyrrolidin-3-amine; (cis)-N1-((1S,2R)-2-(3'-(trifluoromethyl)-[1,1'-biphenyl]-4-yl)cyclopropyl)cyclohexane-1,4-diamine; (trans)-N1-((1S,2R)-2-(3'-(trifluoromethyl)-[1,1'-biphenyl]-4-yl)cyclopropyl)cyclohexane-1,4-diamine; (cis)-N1-((1R,2S)-2-(3'-(trifluoromethyl)-[1,1'-biphenyl]-4-yl)cyclo-propyl)cyclohexane-1,4-diamine; (Trans)-N1-((1R,2S)-2-(3'-(trifluoromethyl)-[1,1'-biphenyl]-yl)cyclopropyl)cyclohexane-1,4-diamine; N1-((trans)-2-(4-cyclopropylphenyl)cyclopropyl)cyclohexane-1,4-diamine; N1-((trans)-2-(4-(pyridin-3-yl)phenyl)cyclopropyl)cyclohexane-1,4-diamine; N1-((trans)-2-(4-(1H-indazol-6-yl)phenyl)cyclopropyl)cyclohexane-1,4-diamine; N1-((trans)-2-(4-(1H-pyrazol-5-yl)phenyl)cyclopropyl)cyclohexane-1,4-diamine; 3-(5-((trans)-2-((4-aminocyclohexyl)amino)cyclopropyl)thiophen-2-yl)phenol; 3-(5-((trans)-2-((4-aminocyclohexyl)amino)cyclopropyl)thiazol-2-yl)phenol; 3-(5-((trans)-2-((4-aminocyclohexyl)amino)cyclopropyl)pyridin-2-yl)-5-methoxybenzonitrile; 5-5-((trans)-2-((4-aminocyclohexyl)amino)cyclopropyl)pyridin-2-yl)-2-methylphenol; N-(4'-((trans)-2-((4-aminocyclohexyl)amino)cyclopropyl)-6-methoxy-[1,1-biphenyl]-3-yl)methanesulfonamide; N-(3-(5-((trans)-2-((4-aminocyclohexyl)amino)cyclopropyl)thiazol-2-yl)phenyl)-2-cyanobenzenesulfonamide; N-(4'-((trans)-2-((4-aminocyclohexyl)amino)cyclopropyl)-[1,1'-biphenyl]-3- yl)-2-cyanobenzenesulfonamide; 6-amino-N-(4'-((trans)-2-((4-aminocyclohexyl)amino)cyclopropyl)-[1,1'-biphenyl]-3-yl)pyridine-3-sulfonamide; N-(4'-((trans)-2-((4-aminocyclohexyl)amino)cyclopropyl)-[1,1'-biphenyl]-3-yl)piperazine-1-sulfonamide; N1-((cis)-2-fluoro-2-phenylcyclopropyl)cyclohexane-1,4-diamine; N1-((trans)-2-(4-((3-(piperazin-1-yl)benzyl)oxy)phenyl)cyclopropyl)cyclohexane-1,4-diamine; N1-((trans)-2-(4-(pyridin-3-ylmethoxy)phenyl)cyclopropyl)cyclohexane-1,4-diamine; N1-((trans)-2-(6-((3-methylbenzyl)amino)pyridin-3-yl)cyclopropyl)cyclohexane-1,4-diamine; 3-((5-((trans)-2-((4-aminocyclohexyl)amino)cyclopropyl)pyridin-2-yl)amino)benzonitrile; N1-((trans)-2-(naphthalen-2-yl)cyclopropyl)cyclohexane-1,4-diamine; N1-((trans)-2-(o-tolyl)cyclopropyl)cyclohexane-1,4-diamine; N1-((trans)-2-(4-(trifluoromethyl)phenyl)cyclopropyl)cyclohexane-1,4-diamine; N1-((trans)-2-(4-methoxyphenyl)cyclopropyl)cyclohexane-1,4-diamine; N1-((trans)-2-(2-fluorophenyl)cyclopropyl)cyclohexane-1,4-diamine; N1-((trans)-2-(3,4-difluorophenyl)cyclopropyl)cyclohexane-1,4-diamine; N1-((trans)-2-methyl-2-phenylcyclopropyl)cyclohexane-1,4-diamine; (cis)-N1-((1S,2R)-2-(pyridin-3-yl)cyclopropyl)cyclohexane-1,4-diamine; (trans)-N1-((1R,2S)-2-(pyridin-3-yl)cyclopropyl)cyclohexane-1,4-diamine; (cis)-N1-((1R,2S)-2-(pyridin-3-yl)cyclopropyl)cyclohexane-1,4-diamine; (trans)-N1-((1S,2R)-2-(pyridin-3-yl)cyclopropyl)cyclohexane-1,4-diamine; (cis)-N1-((1S,2R)-2-phenylcyclopropyl)cyclobutane-1,3-diamine; trans N1-(1R,2S)-2-phenylcyclopropyl)cyclobutane-1.3-diamine; (cis)-N1-((1R,2S)-2-phenylcyclopropyl)cyclobutane-1,3-diamine; (trans)-N1-((1S,2R)-2-phenylcyclopropyl)cyclobutane-1,3-diamine; (cis)-N1-((1S,2R)-2-(3,4-difluorophenyl)cyclopropyl)cyclohexane-1,4-diamine; (trans)-N1-((1R,2S)-2-(3,4-difluorophenyl)cyclopropyl)cyclohexane-1,4-diamine; (cis)-N1-((1R,2S)-2-(3,4-difluorophenyl)cyclopropyl)cyclohexane-1,4-diamine; (trans)-N1-((1S,2R)-2-(3,4-difluorophenyl)cyclopropyl)cyclohexane-1,4-diamine; (cis)-N1-((1S,2R)-2-(naphthalen-2-yl)cyclopropyl)cyclohexane-1,4-diamine; (trans)-N1-((1R,2S)-2-(naphthalen-2-yl)cyclopropyl)cyclohexane-1,4-diamine; (cis)-1-((1R,2S)-2-(naphthalen-2-yl)cyclopropyl)cyclohexane-1,4-diamine; (trans)-N1-((1S,2R)-2-(naphthalen-2-yl)cyclopropyl)cyclohexane-1,4-diamine; (cis)-N1-((1S,2R)-2-(4-(1H-pyrazol-5-yl)phenyl)cyclopropyl)cyclohexane-1,4-diamine; (trans)-N1-((1R,2S)-2-(4-(1H-pyrazol-5-yl)phenyl)cyclopropyl)cyclohexane-1,4-diamine; (cis)-N1-((1R,2S)-2-(4-(1H-pyrazol-5-yl)phenyl)cyclopropyl)cyclohexane-1,4-diamine; (trans)-N1-((1S,2R)-2-(4-(1H-pyrazol-5-yl)phenyl)cyclopropyl)cyclohexane-1,4-diamine; N-(4'-((1R,2S)-2-(((cis)-4-aminocyclohexyl)amino)cyclopropyl)-[1,1'-biphenyl]-3-yl)piperazine-1-sulfonamide; N-(4'-((1S,2R)-2-(((trans)-4-aminocyclohexyl)amino)cyclopropyl)-[1,1'-biphenyl]-3-yl)piperazine-1-sulfonamide; N-(4'-((1S,2R)-2-(((cis)-4-aminocyclohexyl)amino)cyclopropyl)-[1,1'-biphenyl]-3-yl)piperazine-1-sulfonamide; N-(4'-((1R,2S)-2-(((trans)-4-aminocyclohexyl)amino)cyclopropyl)-[1,1'-biphenyl]-3-yl)piperazin; (cis)-N1-((1S,2R)-2-(4-((2-fluorobenzyl)oxy)phenyl)cyclopropyl)cyclohexane-1,4-diamine; (trans)-N1-((1R,2S)-2-(4-((2-fluorobenzyl)oxy)phenyl)cyclopropyl)cyclohexane-1,4-diamine; (cis)-N1-((1R,2S)-2-(4-((2-fluorobenzyl)oxy)phenyl)cyclopropyl)cyclohexane-1,4-diamine; (trans)-N1-((1S,2R)-2-(4-((2-fluorobenzyl)oxy)phenyl)cyclopropyl)cyclohexane-1,4-diamine; or a pharmaceutically acceptable salt or solvate thereof.

In one embodiment, the LSD1 inhibitor is selected from: 1,1-Dimethylethyl 4-({[trans-2-phenylcyclopropyl]amino}methyl)-1-piperidinecarboxylate; 1,1-Dimethylethyl 4-({[(1R,2S)-2-phenylcyclopropyl]amino}methyl)-1-piperidinecarboxylate; 1,1-Dimethylethyl 4-({[(1S,2R)-2-phenylcyclopropyl]amino}methyl)-1-piperidinecarboxylate; [trans-2-Phenylcyclopropyl]([1-(phenylmethyl)-4-piperidinyl]methyl)amine; N-Phenyl-4-(((trans-2-phenylcyclopropyl)amino)methyl)piperidine-1-carboxamide; Phenyl(4-(((trans-2-phenylcyclopropyl)amino)methyl)piperidin-1-yl)methanone; 1-(4-(((trans-2-Phenylcyclopropyl)amino)methyl)piperidin-1-yl)ethanone; Benzyl 4-(((trans-2-phenylcyclopropyl)amino)methyl)piperidine-1-carboxylate; 1,1-Dimethylethyl 4-(([trans-2-phenylcyclopropyl]amino)methyl)hexahydro-1H-azepine-1-carboxylate 2-(4-(((trans-2-phenylcyclopropyl)amino)methyl)piperidin-1-yl)acetic acid; 4-{[(3R)-3-({[(1R,2S)-2-Phenylcyclopropyl]amino}methyl)-1-pyrrolidinyl]methyl}benzoic acid; 4-{[(3S)-3-({[(1R,2S)-2-Phenylcyclopropyl]amino}methyl)-1-pyrrolidinyl]methyl}benzoic acid; 4-{3-[4-({[(1R,2S)-2-Phenylcyclopropyl]amino}methyl)-1-piperidinyl]propyl}benzoic acid; trans-2-Phenyl-N-((1-(pyridin-4-ylmethyl)piperidin-4-yl)methyl)cyclopropanamine; trans-N-((1-(2-Fluorobenzyl)piperidin-4-yl)methyl)-2-phenylcyclopropanamine; trans-N-((1-(3-Fluorobenzyl)piperidin-4-yl)methyl)-2-phenylcyclopropanamine; trans-N-((1-(4-Fluorobenzyl)piperidin-4-yl)methyl)-2-phenylcyclopropanamine; trans-N-((1-(2,4-Difluorobenzyl)piperidin-4-yl)methyl)-2-phenylcyclopropanamine; Ethyl 4-((4-(((trans-2-phenylcyclopropyl)amino)methyl)piperidin-1-yl)methyl)benzoate; trans-N-((1-(4-(Methylsulfonyl)benzyl)piperidin-4-yl)methyl)-2-phenylcyclopropanamine; 2-((4-(((trans-2-Phenylcyclopropyl)amino)methyl)piperidin-1-yl)methyl)benzonitrile; trans-2-Phenyl-N-((1-(2-(trifluoromethyl)benzyl)piperidin-4-yl)methyl)cyclopropanamine; trans-N-((1-((5-Methylisoxazol-3-yl)methyl)piperidin-4-yl)methyl)-2-phenylcyclopropanamine; trans-N-((1-((1H-Pyrazol-4-yl)methyl)piperidin-4-yl)methyl)-2-phenylcyclopropanamine; N-(4-((4-(((trans-2-Phenylcyclopropyl)amino)methyl)piperidin-1-yl)methyl)phenyl)acetamide; 4-((4-(((trans-2-Phenylcyclopropyl)amino)methyl)piperidin-1-yl)methyl)benzo[c][1,2]oxaborol-1(3H)-ol; 5-((4-(((trans-2-Phenylcyclopropyl)amino)methyl)piperidin-1-yl)methyl)benzo[c][1,2]oxaborol-1(3H)-ol; (4-((4-(((trans-2-phenylcyclopropyl)amino)methyl)piperidin-1-yl)methyl)phenyl)boronic acid; 2-((4-(((trans-2-Phenylcyclopropyl)amino)methyl)piperidin-1-yl)methyl)benzoic acid; 3-((4-(((trans-2-Phenylcyclopropyl)amino)methyl)piperidin-1-yl)-methyl)benzoic acid; 4-((4-(((trans-2-(4-Bromophenyl)cyclopropyl)amino)methyl)piperidin-1-yl)methyl)benzoic acid; 4-((4-(((trans-2-(4-Chlorophenyl)cyclopropyl)amino)methyl)piperidin-1-yl)methyl)benzoic acid; 4-((4-(((trans-2-(3,4-Dichlorophenyl)cyclopropyl)amino)methyl)piperidin-1-yl)methyl)benzoic acid; 4-((4-(((trans-2-(4-(Trifluoromethyl)phenyl)cyclopropyl)amino)methyl)piperidin-1-yl)methyl)benzoic acid; 4-((4-(((trans-2-(3,4-Dimethoxyphenyl)cyclopropyl)amino)methyl)piperidin-1-yl)methyl)benzoic acid; 4-((4-(((trans-2-(4-Acetamidophenyl)cyclopropyl)amino)methyl)piperidin-1-yl)methyl)benzoic acid; 4-((4-(((trans-2-(4-Benzamidophenyl)cyclopropyl)amino)methyl)piperidin-1-yl)methyl)benzoic acid; trans-2-Phenyl-N-((1-phenylpiperidin-4-yl)methyl)cyclopropanamine; Ethyl 4-(((trans-2-phenylcyclopropyl)amino)methyl)piperidine-1-carboxylate; trans-4-((4-(((trans-2-Phenylcyclopropyl)amino)methyl)piperidin-1-yl)methyl)cyclohexanecarboxylic acid; (trans)-N-((1-(Methylsulfonyl)piperidin-4-yl)methyl)-2-phenylcyclopropanamine; N-ethyl-4-((((trans)-2-phenylcyclopropyl)amino)methyl)piperidine-1-carboxamide; N-cyclopropyl-4-((((trans)-2-phenylcyclopropyl)amino)methyl)piperidine-1-carboxamide; N,N-dimethyl-4-((((trans)-2-phenylcyclopropyl)amino)methyl)piperidine-1-carboxamide, (4-((((trans)-2-phenylcyclopropyl)amino)methyl)piperidin-1-yl)(pyrrolidin-1-yl)methanone; trans-N-((1-((cyclopropylsulfonyl)piperidin-4-yl)methyl)-2-phenylcyclopropanamine; trans-N-((1-((isopropylsulfonyl)piperidin-4-yl)methyl)-2-phenylcyclopropanamine; trans-N-((1-(3,5-dimethylisoxazol-4-yl)sulfonyl)piperidin-4-yl)methyl)-2-phenylcyclopropanamine; trans-N-((1-((1,2-dimethyl-1H-imidazol-4-yl)sulfonyl)piperidin-4-yl)methyl)-2-phenylcyclopropanamine; (trans)-2-Phenyl-N-(2-(1-(pyridin-2-yl)piperidin-4-yl)ethyl)cyclopropanamine; 6-(4-(2-(((trans)-2-Phenylcyclopropyl)amino)ethyl)piperidin-1-yl) nicotinic acid; trans-2-phenyl-N-(2-(1-(pyridin-4-yl)piperidin-4-yl)ethyl)cyclopropanamine; trans-2-phenyl-N-(2-(1-(pyrimidin-4-yl)piperidin-4-yl)ethyl)cyclopropanamine; trans-2-phenyl-N-(2-(1-phenylpiperidin-4-yl)ethyl)cyclopropanamine; trans-2-phenyl-N-(2-(1-(pyridin-3-yl)piperidin-4-yl)ethyl)cyclopropanamine; trans-2-phenyl-N-(2-(1-(pyrimidin-2-yl)piperidin-4-yl)ethyl)cyclopropan-amine; 3-Cyano-4-((4-((((trans)-2-phenylcyclopropyl)amino)methyl)piperidin-1-yl)methyl)benzoic acid; 2-fluoro-4-((4-((((trans)-2-phenylcyclopropyl)amino)methyl)piperidin-1-yl)methyl)benzoic acid; 3-fluoro-4-((4-((((trans)-2-phenylcyclopropyl)amino)methyl)piperidin-1-yl-)methyl)benzoic acid; 3-chloro-4-((4-((((trans)-2-phenylcyclopropyl)amino)methyl)piperidin-1-yl-)methyl)benzoic acid; 3-methoxy-4-((4-((((trans)-2-phenylcyclopropyl)amino)methyl)piperidin-1-yl)methyl)benzoic acid; 2-chloro-4-((4-((((trans)-2-phenylcyclopropyl)amino)methyl)piperidin-1-yl)methyl)benzoic acid; 4-(3-(4-(Cyano(((1R,2S)-2-phenylcyclopropyl)amino)methyl)piperidin-1-yl)propyl)benzoic acid; 4-{3-[4-({[(trans))-2-phenylcyclopropyl]amino}methyl)-1-piperidinyl]propyl}benzoic acid; 4-(4-(4-((((1R,2S)-2-Phenylcyclopropyl)amino)methyl)piperidin-1-yl)butyl)benzoic acid; 4-(4-(4-(Cyano(((1R,2S)-2-phenylcyclopropyl)amino)methyl)piperidin-1-yl)butyl)benzoic acid; 4-(2-(4-((((trans)-2-Phenylcyclopropyl)amino)methyl)piperidin-1-yl)ethyl)benzoic acid; 4-(2-(4-((((1R,2S)-2-phenylcyclopropyl)amino)methyl)piperidin-1-yl)ethyl)benzoic acid; 6-((4-((((trans)-2-Phenylcyclopropyl)amino)methyl)piperidin-1-yl)methyl)-2-naphthoic acid; 6-((4-((((1R,2S)-2-Phenylcyclopropyl)amino)methyl)piperidin-1-yl)methyl)-2-naphthoic acid; (trans)-N-((1-(4-(1H-Tetrazol-5-yl)benzyl)piperidin-4-yl)methyl)-2-phenylcyclopropanamine; 2-(4-((4-((((trans)-2-Phenylcyclopropyl)amino)methyl)piperidin-1-yl)methyl)benzamido)acetic acid; N-(4-((4-((((trans)-2-Phenylcyclopropyl)amino)methyl)piperidin-1-yl)methyl)phenyl)methanesulfonamide; (trans)-N-((1-(3-(1H-Tetrazol-5-yl)propyl)piperidin-4-yl)methyl)-2-phenylyclopropanamine; 4-((4-(2-(((trans)-2-Phenylcyclopropyl)amino)ethyl)piperidin-1-yl)methyl)-benzoic acid; 6-((4-(((((trans)-2-Phenylcyclopropyl)amino)methyl)piperidin-1-yl)methyl)nicotinic acid; 2-(4-((4-(((((trans)-2-Phenylcyclopropyl)amino)methyl)piperidin-1-yl)methyl)phenyl)acetic acid; 2-((4-(((((trans)-2-Phenylcyclopropyl)amino)methyl)piperidin-1-yl)methyl)oxazole-4-carboxylic acid; 2-(4-((4-(((((trans)-2-phenylcyclopropyl)amino)methyl)piperidin-1-yl)methyl)phenoxy)acetic acid; N-(Methylsulfonyl)-4-((4-(((((trans)-2-phenylcyclopropyl)amino)methyl)piperidin-1-yl)methyl)benzamide; 4-((4-(((((trans)-2-(4-Iodophenyl)cyclopropyl)amino)methyl)piperidin-1-yl)methyl)benzoic acid; 4-((trans)-2-(((1-Benzylpiperidin-4-yl)methyl)amino)cyclopropyl)benzoic acid; 4-((4-(((((trans)-2-(4-(1-Methyl-1H-pyrazol-4-yl)phenyl)cyclopropyl)amino)methyl)piperidin-1-yl)methyl)benzoic acid; 4-((4-(((((trans)-2-(4-Cyclopropylphenyl)cyclopropyl)amino)methyl)piperidin-1-yl)methyl)benzoic acid; 2-Chloro-4-((4-(((((1R,2S)-2-phenylcyclopropyl)amino)methyl)piperidin-1-yl)methyl)benzoic acid; 3-(3-(4-(((((trans)-2-Phenylcyclopropyl)amino)methyl)piperidin-1-yl)propyl)benzoic acid; or 2-(4-((4-(((((1R,2S)-2-Phenylcyclopropyl)amino)methyl)piperidin-1-yl)methyl)phenyl)acetic acid or a pharmaceutically acceptable salt or solvate thereof.

In one embodiment, the LSD1 inhibitor, which may also be referred to as a KDM1A inhibitor, is selected from the group consisting of:
tranylcypromine;

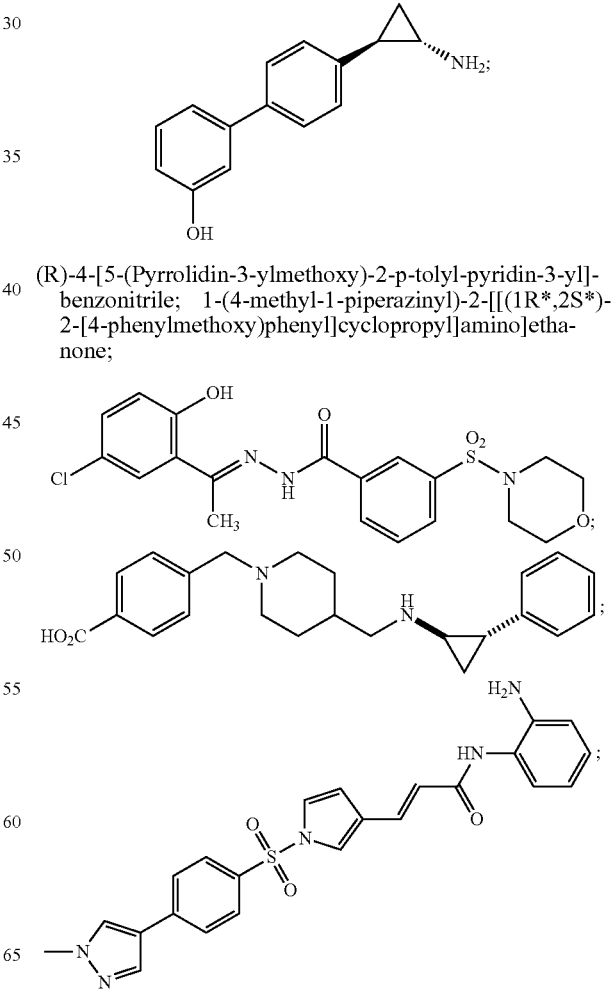

(R)-4-[5-(Pyrrolidin-3-ylmethoxy)-2-p-tolyl-pyridin-3-yl]-benzonitrile; 1-(4-methyl-1-piperazinyl)-2-[[(1R*,2S*)-2-[4-phenylmethoxy)phenyl]cyclopropyl]amino]ethanone;

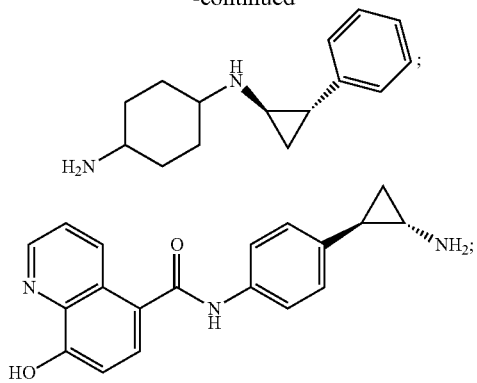

N-[4-[trans-2-aminocyclopropyl]phenyl]-4-(4-methylpiperazin-1-yl)benzamide; and a pharmaceutically acceptable salt thereof. (Maes, T. et al. Current Opinion in Phamacol. 2015, 23:52-60).

In one embodiment, the LSD1 inhibitor is N-[4-[trans-2-aminocyclopropyl]phenyl]-4-(4-methylpiperazin-1-yl)benzamide, or a pharmaceutically acceptable salt thereof.

In one aspect, the disclosure relates to a pharmaceutical composition in the form of tablets, capsules, oral preparations, powders, granules, pills, injectable or infusible liquid, solutions, suspensions, emulsions, suppositories, ointments, creams, lotions, lozenges, chews, gels, pastes, multi- and nano-particulates, gels, solid solutions, liposomes, nanoparticles, films, ovules, sprays, injectables, and liquid formulations or transdermal delivery devices. A reference for the formulations is the book by Remington ("Remington: The Science and Practice of Pharmacy", Lippincott Williams & Wilkins, 2000).

Compounds and/or compositions of the application may be administered to a subject in a total daily dose of, for example, from 0.001 to 1000 mg/kg body weight daily. Dosage unit compositions may contain such amounts of submultiples thereof to make up the daily dose. The determination of optimum dosages for a particular subject is well known to one skilled in the art.

Any of the compounds, combinations, pharmaceutical compositions, and/or dosage forms described herein can be administered to the subject via an oral, topical, intravenous, inhalational, otic, intramucosal, intraarterial, intraocular, intraperitoneal, intrathecal, intraventricular, intraurethral, intrasternal, intracranial, intramuscular, and/or subcutaneous route of administration.

Any of the compounds, combinations, pharmaceutical compositions, and/or dosage forms described herein can be administered to the subject on a daily (e.g., 1, 2, or 3 times daily), weekly (e.g., 1, 2, 3, 4, or 5 times weekly), or monthly basis (e.g., 1, 2, 3, 4, 5, 6, 7, 8, 9, or 10 times monthly). Determination of the appropriate dosing schedule is within the routine level of skill in the art.

Any of the compounds, combinations, pharmaceutical compositions, and/or dosage forms described herein may be formulated with pharmaceutically acceptable carriers or diluents as well as any other known adjuvants and excipients in accordance with conventional techniques such as those disclosed in Remington: The Science and Practice of Pharmacy, 21st Edition, 2000, Lippincott Williams & Wilkins, which is incorporated herein in its entirety.

As is common practice, the compositions are normally accompanied by written or printed instructions for use in the treatment in question.

Another aspect of the disclosure is a kit comprising an LSD1 inhibitor, combination or pharmaceutical composition as defined herein and at least one therapeutic agent selected from the group consisting of: histone deacetylase inhibitors, retinoid receptor modulators, antiproliferative/antineoplastic agents, cytostatic agents, agents which inhibit cancer cell invasion, inhibitors of growth factor function, antiangiogenic agents, cell cycle inhibitors, proteasome inhibitors, HSP90 inhibitors, Selective COX-2 inhibitors and chemotherapeutic agents.

Optionally, the compound of the disclosure and the at least one therapeutic agent are in separated containers.

Also, various inventive concepts may be embodied as one or more methods or pharmaceutical compositions for use, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All publications, patent applications, patents, and other references mentioned herein are incorporated by reference in their entirety.

Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

All definitions, as defined and used herein, should be understood to control over dictionary definitions, definitions in documents incorporated by reference, and/or ordinary meanings of the defined terms.

The phrase "pharmaceutically acceptable excipient" refers to any of the following classes of ingredients: fillers, binders, lubricants, disintegrating agents, glidants (e.g., silicon dioxide), flavoring agents and colorants. Suitable binders include, e.g., microcrystalline cellulose (e.g., Avicel PH200 LM, PH112, PH101, PH102, PH103, PH113, PH105, PH200, DG), mannitol, dicalcium phosphate, dicalcium phosphate anhydrous, povidone, lactose, glucose, starch, gelatin, acacia gum, tragacanth gum, sodium alginate, carboxymethylcellulose, polyethylene glycol, waxes or the like. Lubricants include, e.g., glyceryl dibehenate, hydrogenated vegetable oil, sodium oleate, sodium stearate, magnesium stearate, silicon dioxide, sodium benzoate, sodium acetate, sodium chloride or the like. Other excipients include, e.g., starch, methyl cellulose, agar, bentonite, xanthan gum, sodium starch glycolate, crospovidone, croscarmellose sodium or the like. Additional excipients for capsules include macrogols or lipids and/or any other excipients known in the art.

Any of the compositions or pharmaceutical compositions described herein may be formulated with pharmaceutically acceptable carriers or diluents as well as any other known adjuvants and excipients in accordance with conventional techniques such as those disclosed in Remington: The Science and Practice of Pharmacy, 21$^{st}$ Edition, 2000, Lippincott Williams & Wilkins, which is incorporated herein in its entirety.

The term "about," as used herein, and unless explicitly stated otherwise, refers to a recited value+/−10%, +/−5%, +/−2.5%, +/−1%, or +/−0.5%. For example, "about" may refer to a recited value+/−5%.

The term, "subject" as used herein refers to a human or non-human, i.e., a patient. In one embodiment, the subject is a mammal. In one embodiment, the subject is a human.

The phrase, "therapeutically effective amount" or "effective amount" as used herein indicates an amount necessary to administer to a subject, or to a cell, tissue, or organ of a subject, to achieve a therapeutic effect, such as an ameliorating or alternatively a curative effect.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein, phrases containing the term "and/or" such as "A, B and/or C" refer to any of the following: A only; B only, C only; A and B; A and C; B and C; A, B and C.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

EXAMPLES

The following working examples are illustrative and are not intended to be limiting and it will be readily understood by one of skill in the art that other embodiments may be utilized.

Example 1. APL NB4 Cell Line is Resistant to LSD1 Inhibition

Figure 1B:
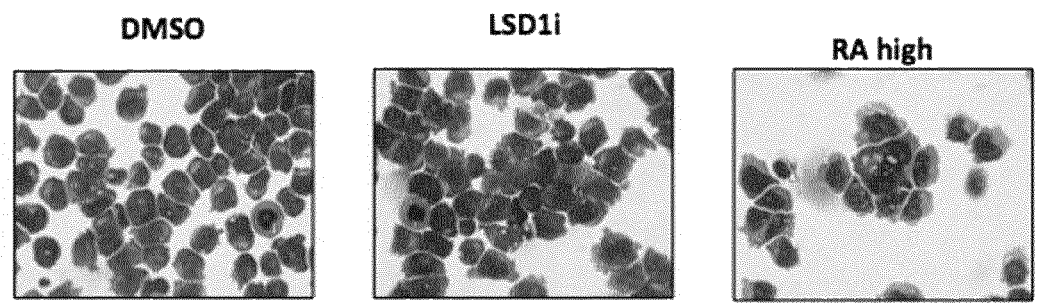
(FIG. 1B) Representative light micrographs show Wright-Giemsa staining of NB4 cell after treatment for 6 days. (DMSO serves as a control).
Figure 1C:
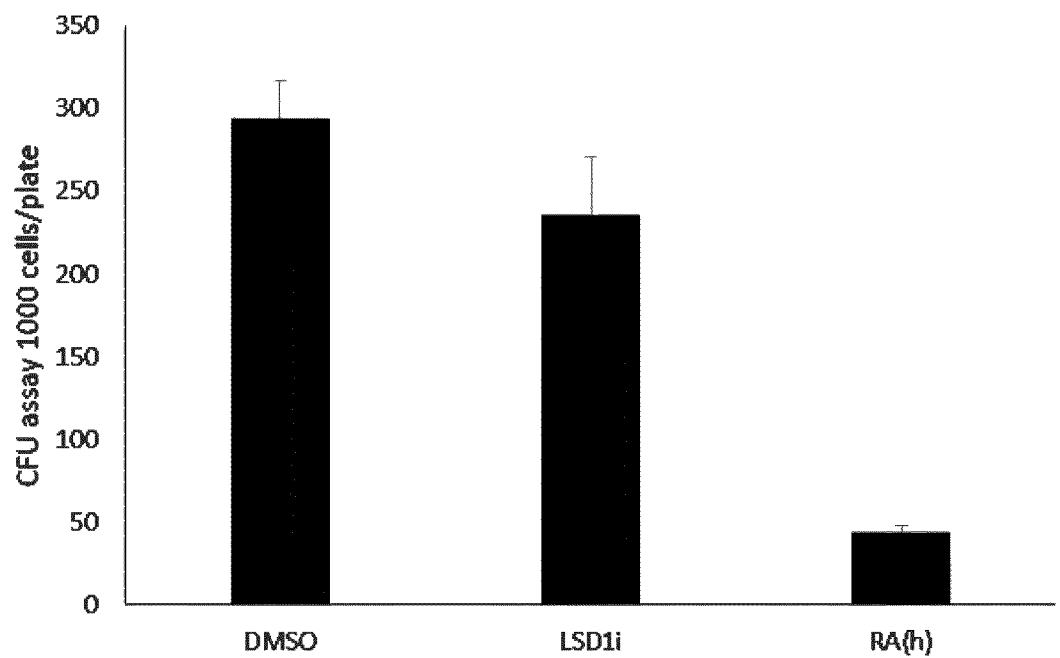
(FIG. 1C) Analysis of the proliferative potential of treated NB4 cells by serial replating assay. (DMSO serves as control). (RA high (h)=retinoic acid, 1 μM, LSD1i=LSD1 inhibitor=MC2580).

Acute promyelocytic leukemia (APL) NB4 cells were treated with 2 µM LSD1 inhibitor MC2580, 1 µM retinoic acid (RA), and DMSO (control) for 6 days. The proliferation of the treated cells were quantified before treatment and during each of the 6 days (FIG. 1A). The treated cells were analyzed under light micrographs using Wright-Giemsa staining (FIG. 1B). The proliferation potential of the treated cells were analyzed by serial replating and Colony-Forming Unit (CFU) Assay (FIG. 1C). FIG. 1A-C demonstrate that the NB4 cells are largely insensitive to LSD1 inhibitor MC2580.

Figure 2A:
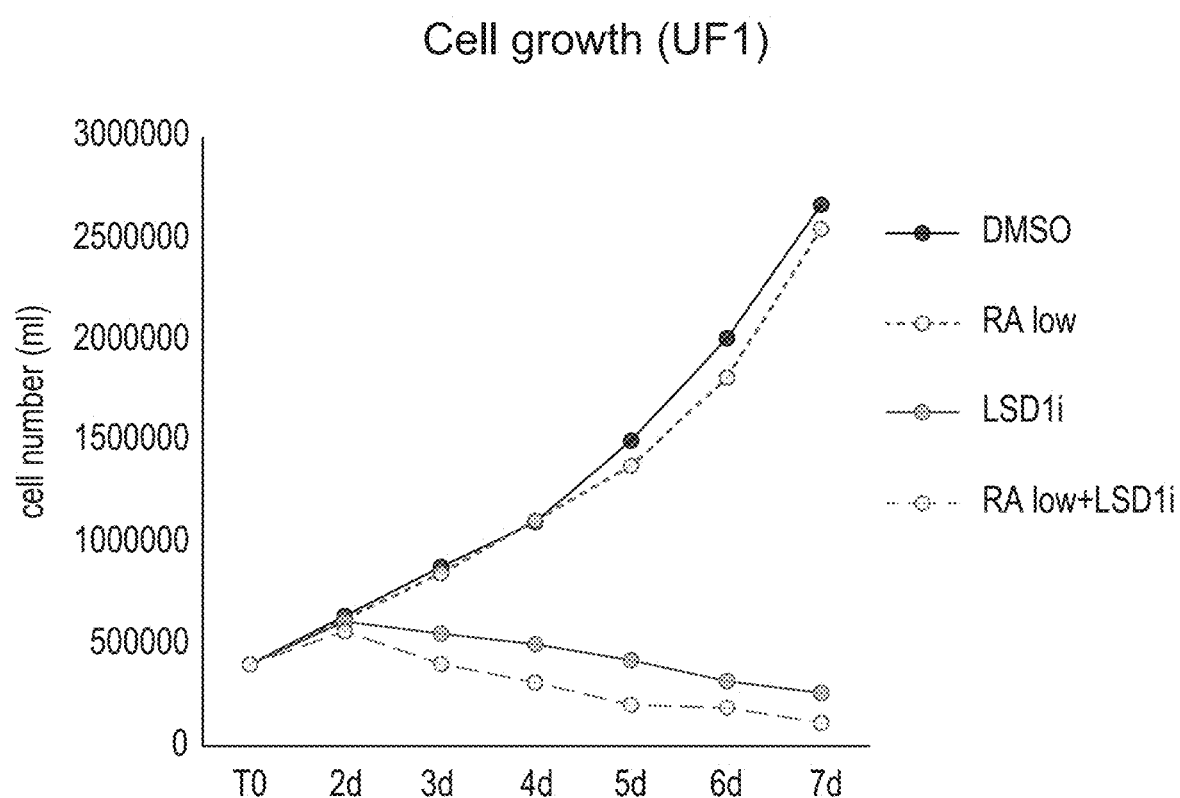
(FIG. 2A) Relative proliferation of UF1 cells treated with MC2580 (2 μM) and/or retinoic acid (10 nM) for 1 week.
Figure 2B:
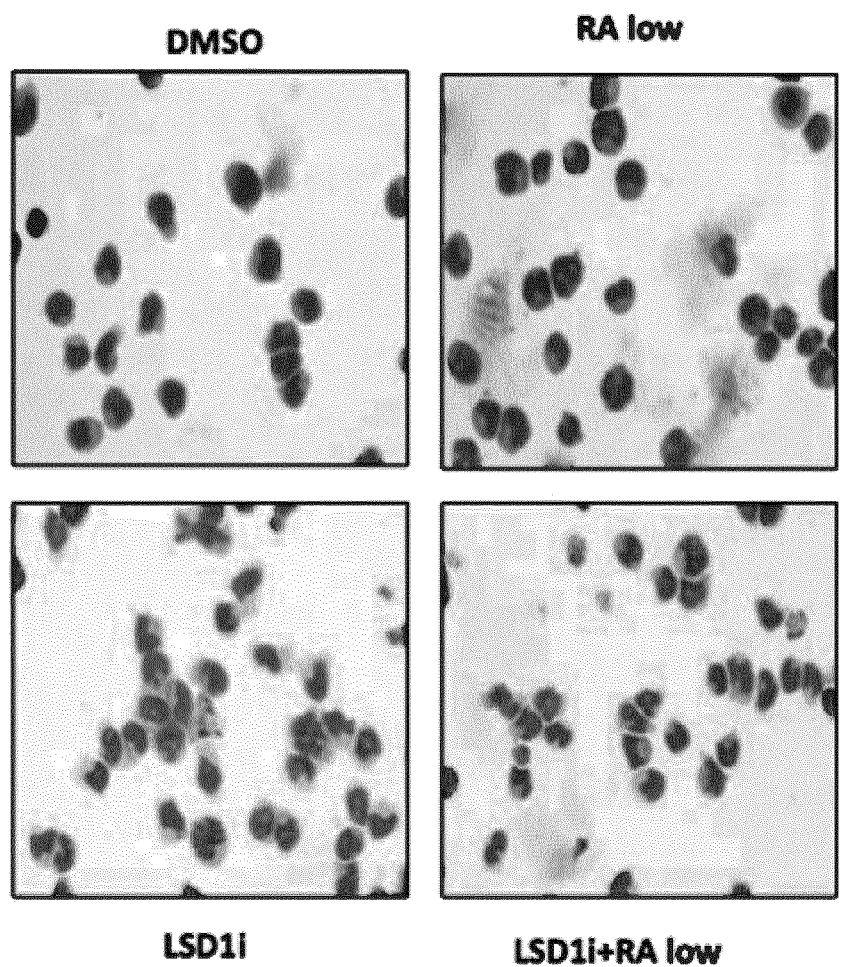
(FIG. 2B) Representative light micrograph show Wright-Giemsa staining of UF1 cell after treatment for 1 week.
Figure 2C:
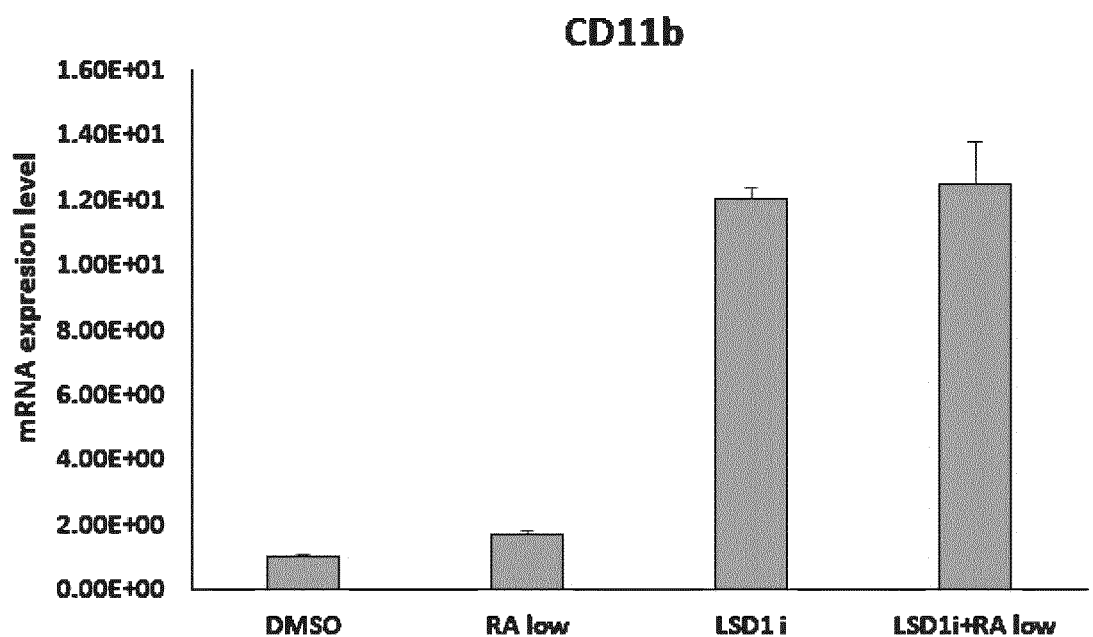
(FIG. 2C) LSD1 inhibition induces expression of the CD11b gene (a myeloid differentiation marker). Values are normalized against GAPDH.
Figure 2D:
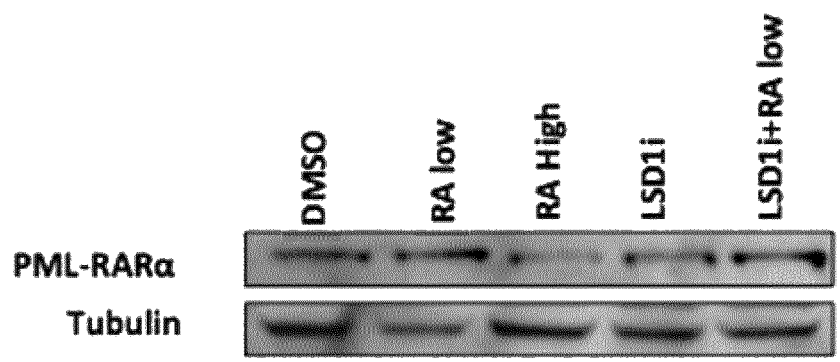
(FIG. 2D) Immunoblot of PML-RARα in treated UF1 cells with indicated inhibitors. LSD1 inhibitors induces differentiation without PML-RARα degradation. (tubulin serves as control).
Figure 2E:
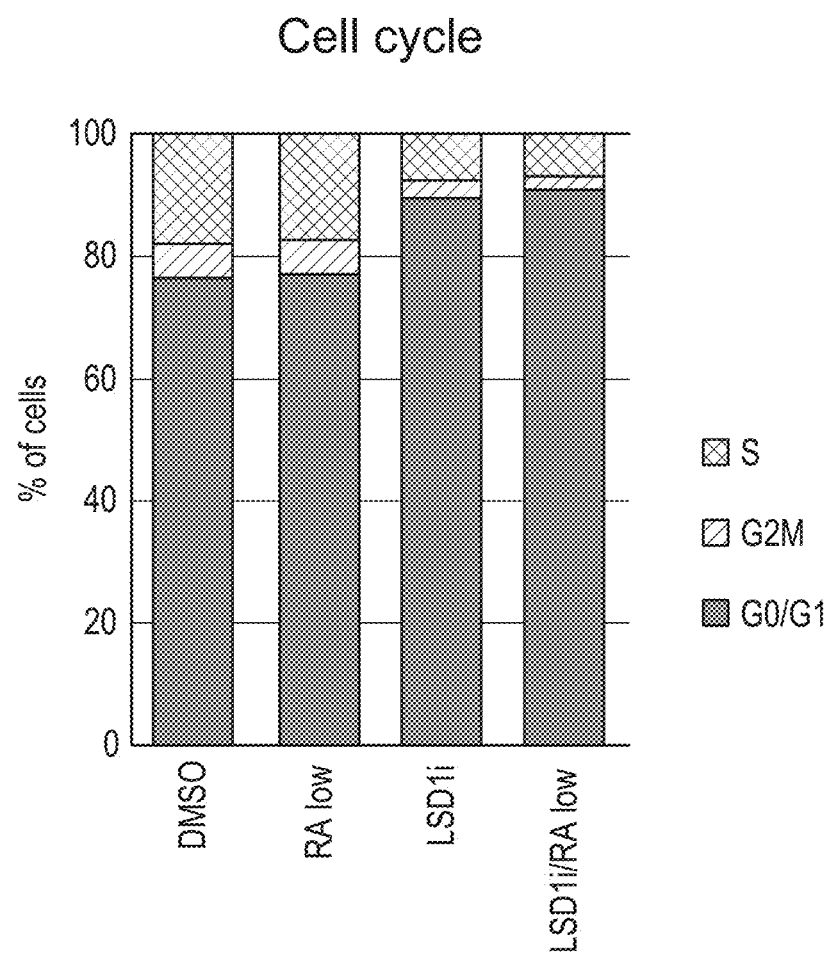
(FIG. 2E) summary of cell-cycle status of UF1 cells following 1 week treatment with indicated inhibitors. (retinoic acid low(l)=10 nM, LSD1i=LSD1 inhibitor=MC2580).

Example 2. LSD1 Inhibition in UF1 Cells Inhibits their Growth, Promotes Differentiation and Induces Cell Cycle Arrest Acute promyelocytic leukemia (APL) UF1 cells were treated with 2 µM LSD1 inhibitor MC2580, 10 nM retinoic acid (RA), 2 µM LSD1 inhibitor MC2580 plus10 nM RA, and DMSO (control) for 7 days. The proliferation of the treated cells were quantified before treatment and post-treatment from each of day 2 to day 7 (FIG. 2A). The cells following the 1 week treatment were analyzed under light micrographs using Wright-Giemsa staining (FIG. 2B). The LSD1-inhibition induced expression of CD11b gene expression were analyzed. The mRNA of CD11b of the treated cells under each condition were normalized using GAPDH (FIG. 2C). PML-RARα protein level in the treated cells was analyzed by immune-blotting using an antibody against PML-RARα. Immuno-blotting of tubulin was used as loading control. (FIG. 2D). FIG. 2D shows that LSD1 inhibitors induces UF1 cells differentiation without PML-RARα degradation. Cell cycle analysis were performed following the 1 week treatment. More UF1 cells were arrested at the G0/G1 phase under LSD1 inhibitor treated conditions. (FIG. 2E). FIG. 2A-E demonstrate that the UF1 cells are sensitive to LSD1 inhibitor MC2580.

Example 3. LSD1 Depletion in UF1 Cells Mimics the Effect of LSD1 Inhibitor

Figure 3A:
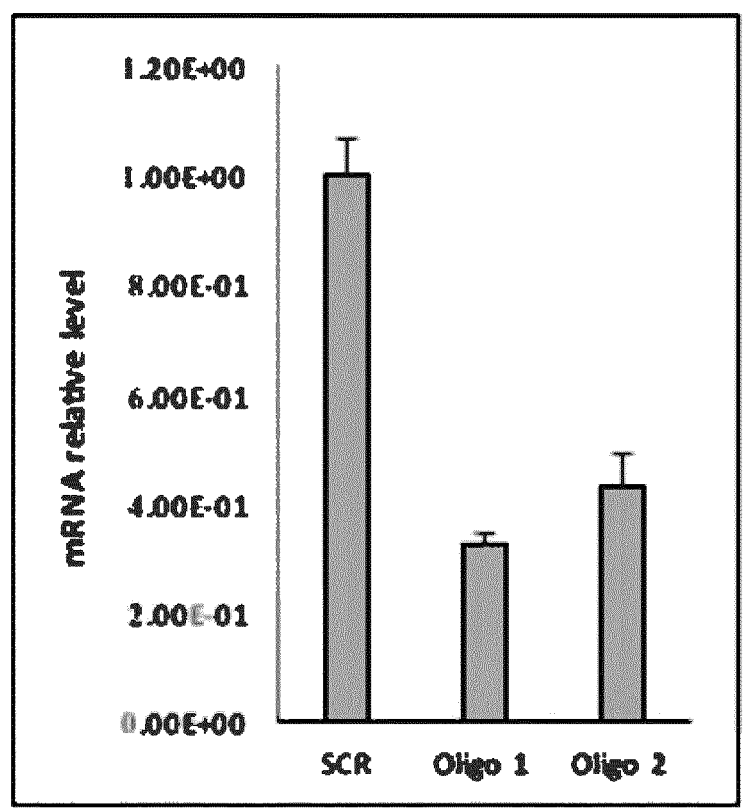
FIG. 3. LSD1 depletion in UF1 cells, mimics the effect of LSD1 inhibitor. (A,B) UF1 cell were infected with SCR (control) or LSD1 shRNAs, and knockdown was monitored by qPCR and western blot. (C) Relative proliferation of UF1 cells infected with SCR (control) or LSD1 shRNAs for indicated duration. (D) Representative light micrographs show Wright-Giemsa staining of UF1 cell 1 week post-infection. (E) LSD1 depletion induces expression of the CD11b gene (a myeloid differentiation marker). Values are normalized against GAPDH. (F) summary of cell-cycle status of UF1 cells 1 week post-infection. (SCR=Scramble shRNA)
Figure 3B:
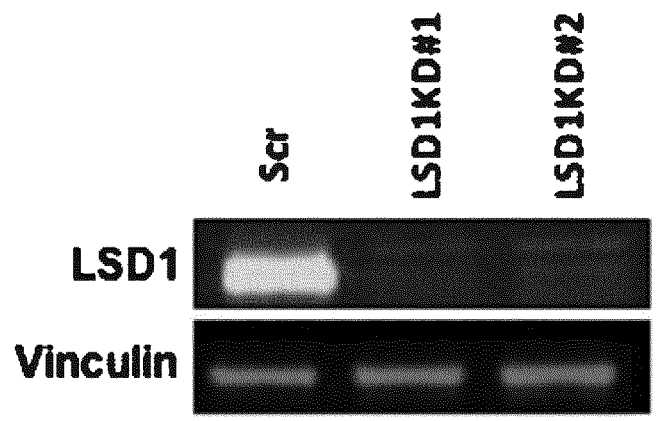
Figure 3C:
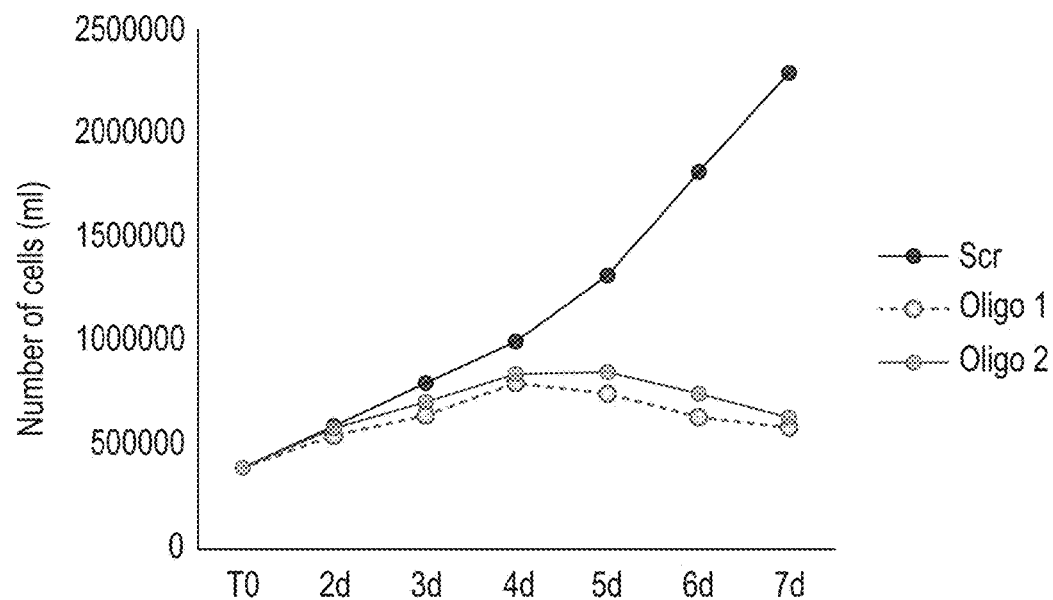
Figure 3D:
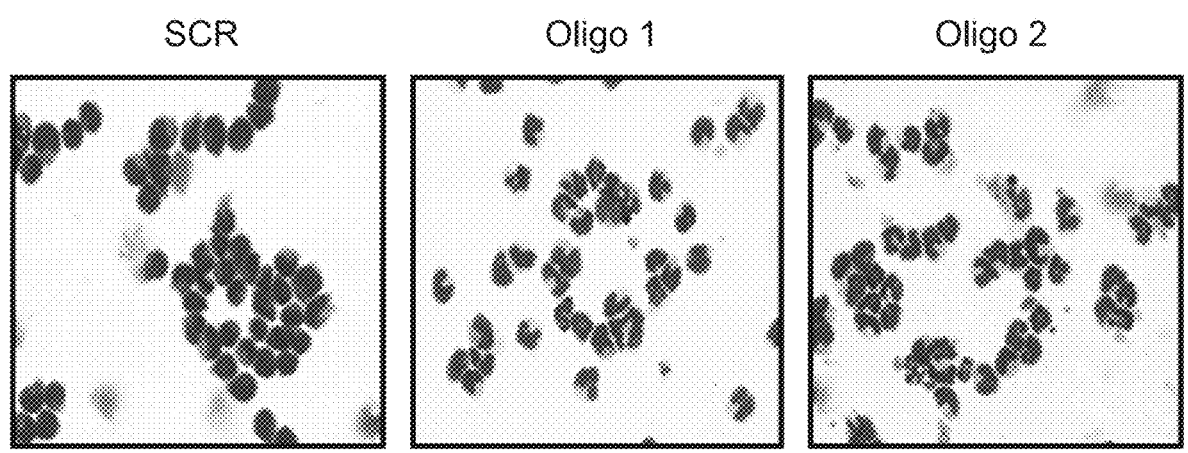
Figure 3E:
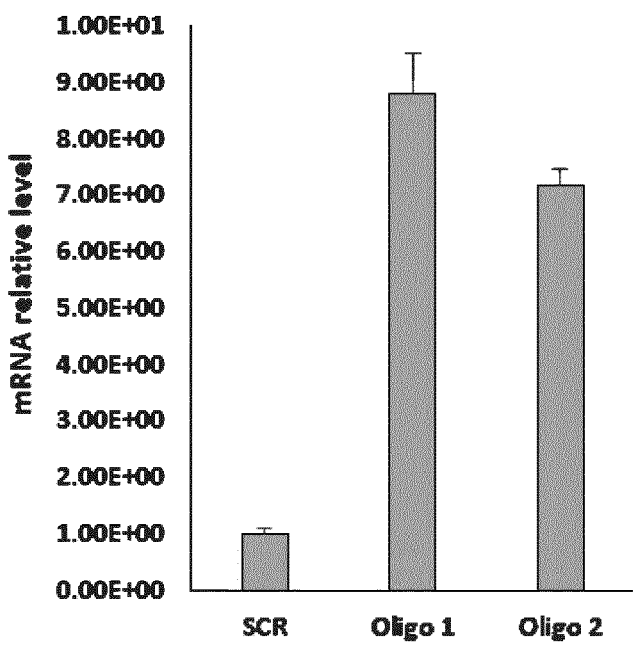
Figure 3F:
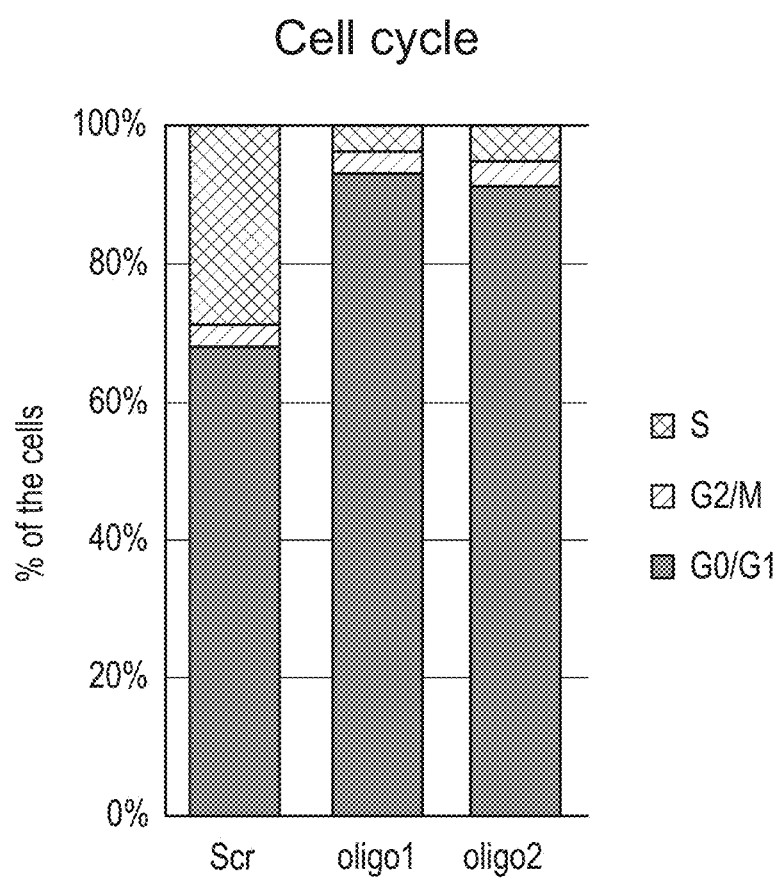

LSD1 expression was knocked-down using two different shRNA oligos targeting LSD1 gene. The reduced LSD1 mRNA in the UF1 cells treated with the two oligos compared to control (SCR shRNA) was qualified using qPCR and is shown in FIG. 3A. The reduced LSD1 protein level in the UF1 cells treated with the two oligos compared to control (SCR (scramble shRNA)) was qualified using Western-blot and is shown in FIG. 3B. The proliferation of the treated cells were quantified before treatment and 48 hours, 72 hours, 96 hours, 120 hours, 144 hours, and 168 hours post-shRNA infection (FIG. 3C). The treated cells were analyzed under light micrographs using Wright-Giemsa staining (FIG. 3D). The LSD1-depletion induced expression of CD11b gene expression were analyzed. The mRNA of CD11b of the treated cells under each condition were normalized using GAPDH (FIG. 3E). Cell cycle analysis were performed at 1 week post-infection. More UF1 cells were arrested at the G0/G1 phase under LSD1 inhibitor treated conditions. (FIG. 3F). FIG. 3A-F demonstrate that LSD1 depletion in UF1 cells mimics the effect of LSD1 inhibitor.

Figure 4A:
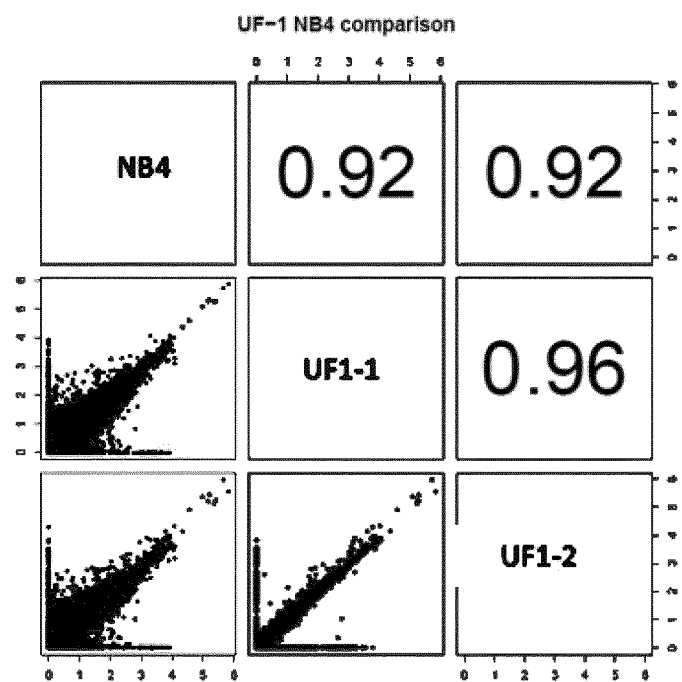
(FIG. 4A) high correlation in gene expression profiling in UF1 and NB4 cells.
Figure 4B:
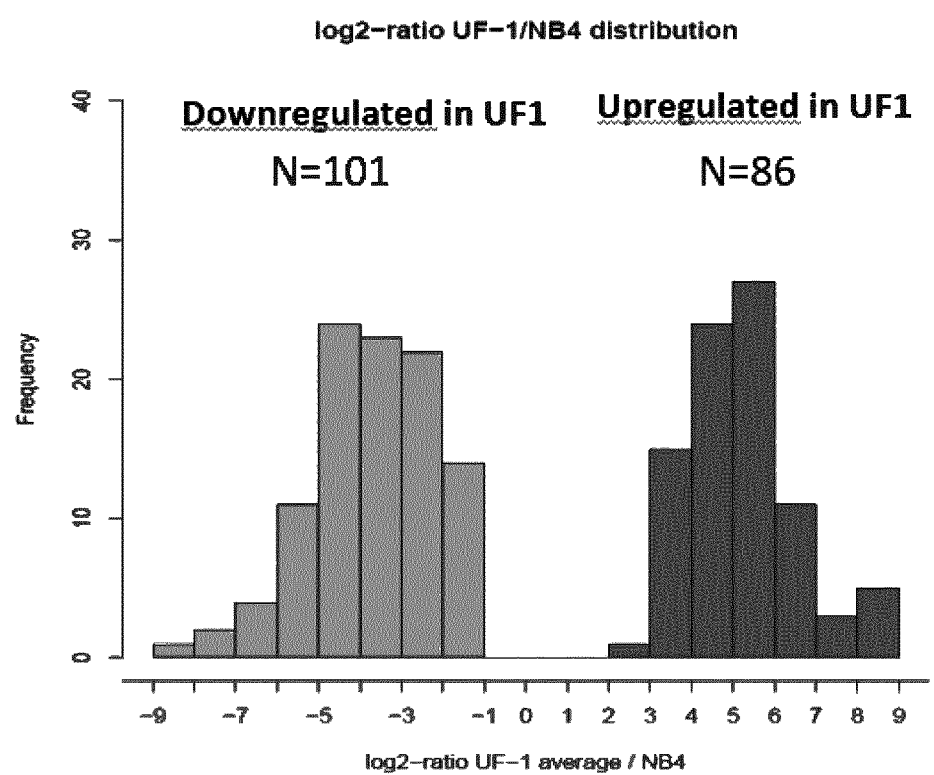
(FIG. 4B) There are 86 genes and 101 genes up and down-regulated respectively in UF1 cells compared to NB4 cells (FIG. 4C, FIG. 4D) High basal level of p21 expression in UF1 cells in comparison with NB4 cells. Values are normalized against GAPDH.
Figure 4C:
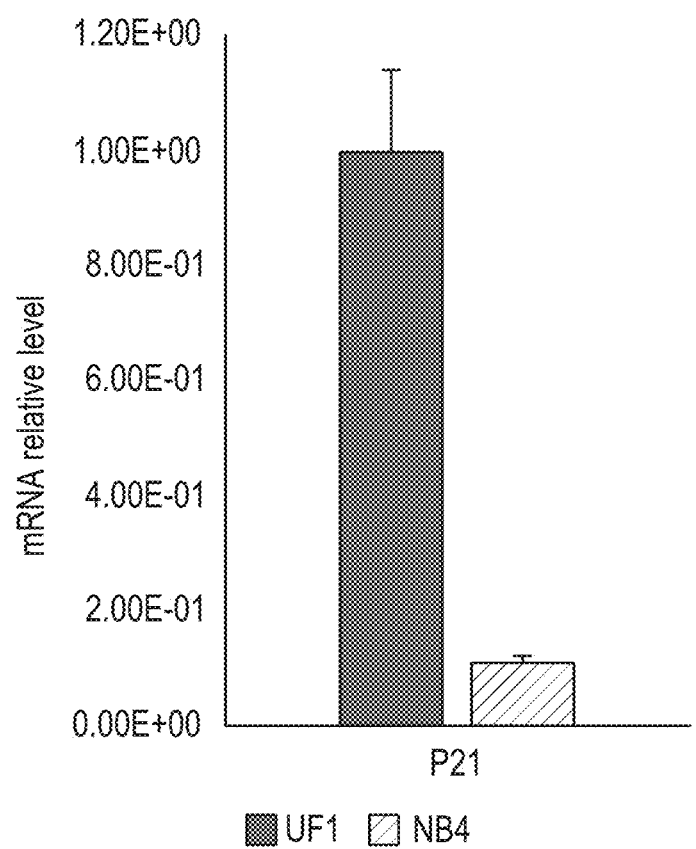
FIG. 4. UF1 cells have high basal level of p21 expression in comparison with NB4 cells.
Figure 4D:
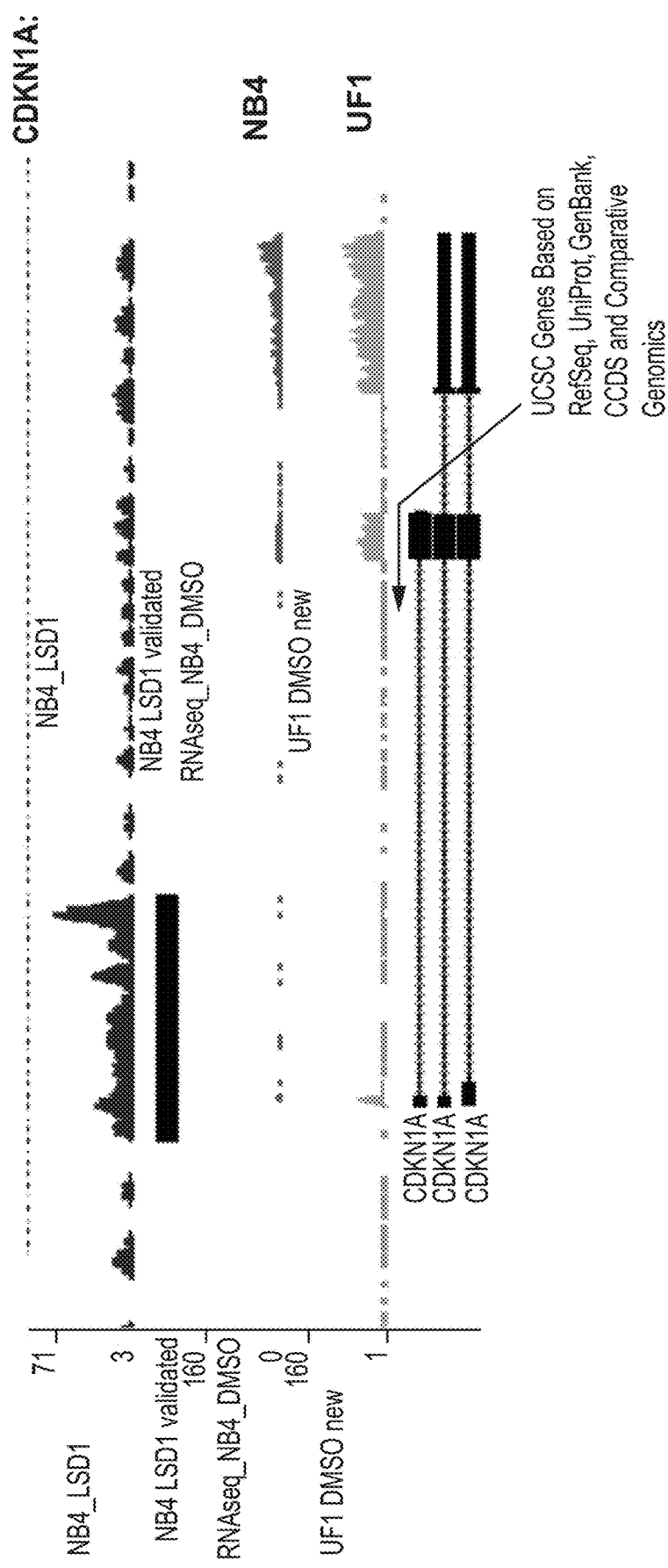

Example 4. UF1 Cells have High Basal Level of p21 Expression in Comparison with NB4 Cells Gene expression profile of UF1 cells was compared to that of NB4 cells. There was a high correlation in gene expression profiling between UF1 and NB4 cells (FIG. 4A). However, there were 86 genes and 101 genes up and down regulated respectively in UF1 cells compared to NB4 cells (FIG. 4B). In particular, the mRNA level of P21 expression in UF1 cells was significantly higher than in NB4 cells were normalized using GAPDH (FIG. 4C). p21 gene (CDKN1A) was expressed at a higher level in UF1 cells than in NB4 cells (FIG. 4D).

Figure 5A:
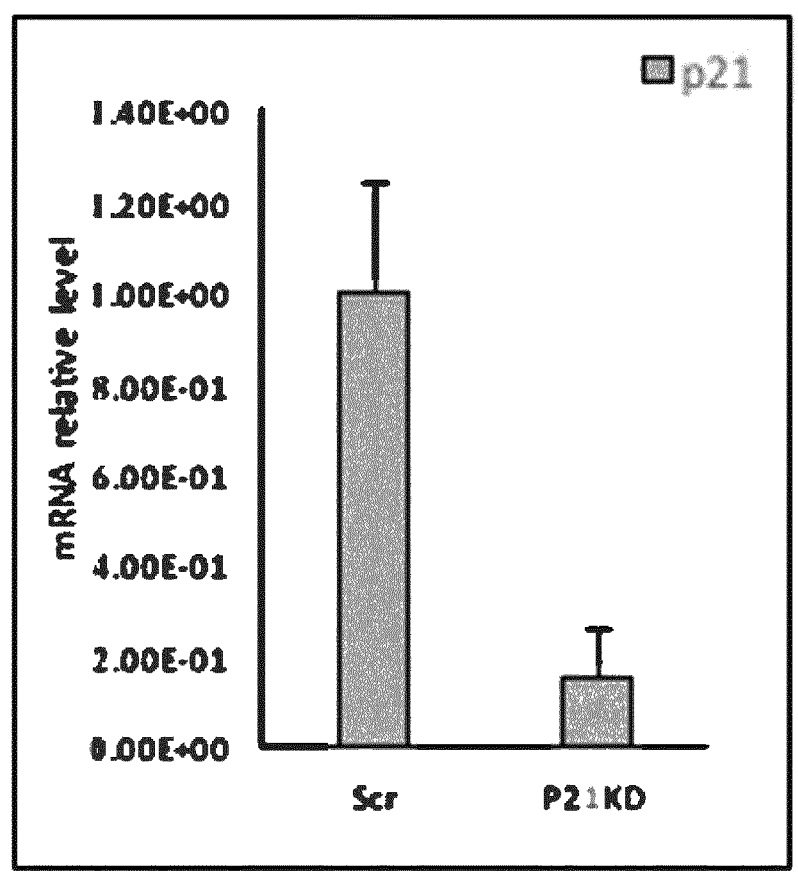
FIG. 5. Knockdown of p21 rescued UF1 cells from cell growth inhibition, induction of differentiation and cell cycle arrest mediated by LSD1 inhibitor (FIG. 5A, FIG. 5B) UF1 cells were infected with SCR (control) or P21 shRNA, and knockdown was monitored by qPCR and western blot.
(FIG. 5C) Relative proliferation of UF1 cells infected with SCR (control) or p21 shRNA treated with MC2580.
(FIG. 5D) Representative light micrograph show Wright-Giemsa staining of UF1 cells after 1 week treatment with indicated inhibitors.
(FIG. 5E) Summary of cell-cycle status of UF1 cells following 1 week treatment with indicated inhibitors. (SCR=Scramble shRNA, NI=Not Infected, LSD1i=LSD1 inhibitor=MC2580).
Figure 5B:
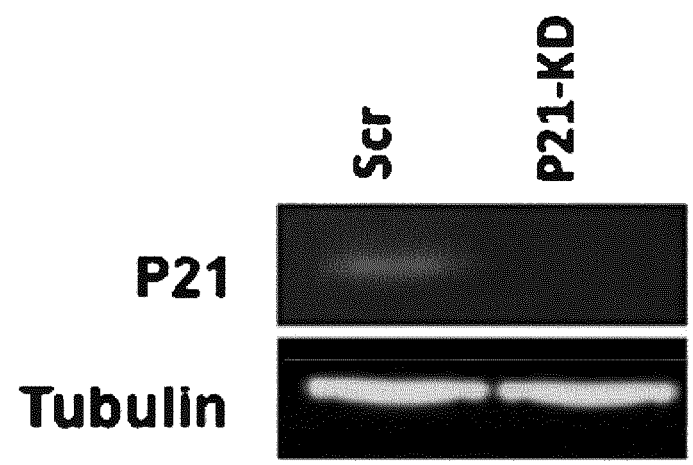

Example 5. Knockdown of p21 Rescued UF1 Cells from Cell Growth Inhibition, Induction of Differentiation and Cell Cycle Arrest Mediated by LSD1 Inhibitor The p21 expression of UF1 cells were knocked-down using shRNA oligos targeting p21 gene. The reduced p21 mRNA in the UF1 cells treated with the oligos compared to control (SCR shRNA) was qualified using qPCR and is shown in FIG. 5A. The reduced p21 protein level in the UF1 cells treated with the oligos compared to control (SCR shRNA) was qualified using Western-blot and is shown in FIG. 5B.

Figure 5D:
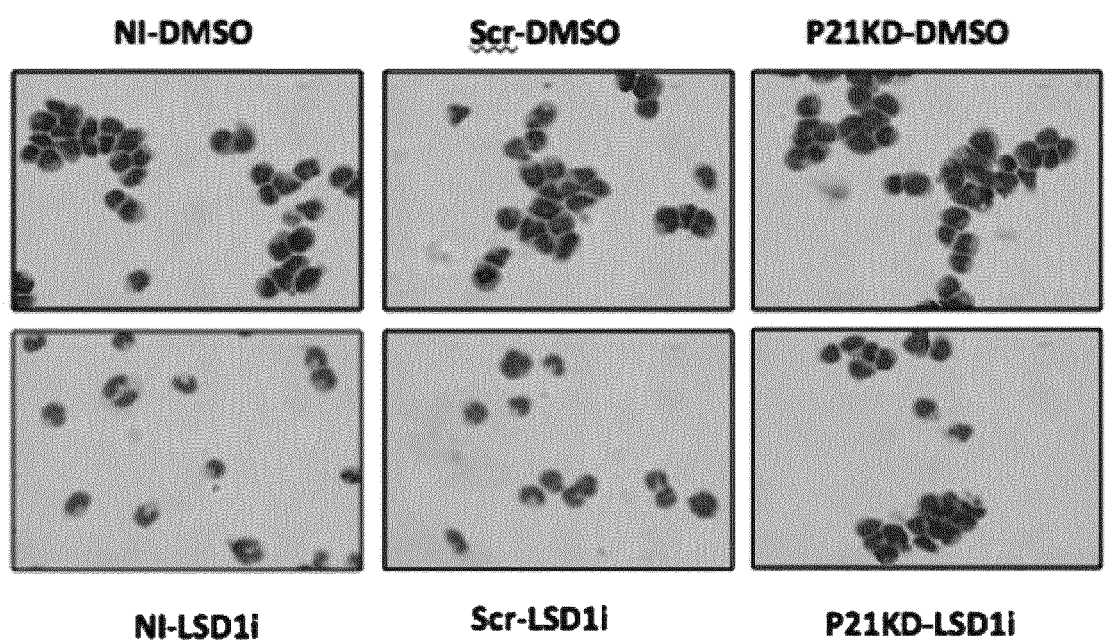
Figure 5E:
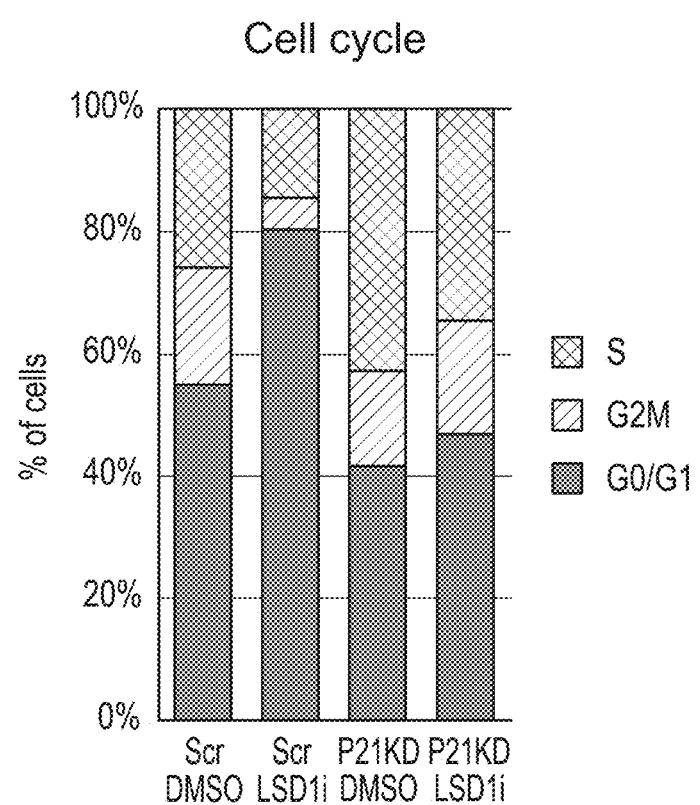

UF1 cells were treated with p21-shRNA, scramble shRNA (SCR), LSD1 inhibitor MC2580, p21-shRNA plus MC2580, scramble shRNA (SCR) plus MC2580. Non-infected (NI) UF1 cells were included as control. The proliferation of the treated cells were quantified before treatment and post-treatment from each of day 2 to day 7 (FIG. 5C). The cells following the 1 week treatment were analyzed under light micrographs using Wright-Giemsa staining (FIG. 5D). Cell cycle analysis were performed following the 1 week treatment. More UF1 cells were arrested at the G0/G1 phase under LSD1 inhibitor treated conditions than cells under the other conditions. (FIG. 5E).

Figure 6A:
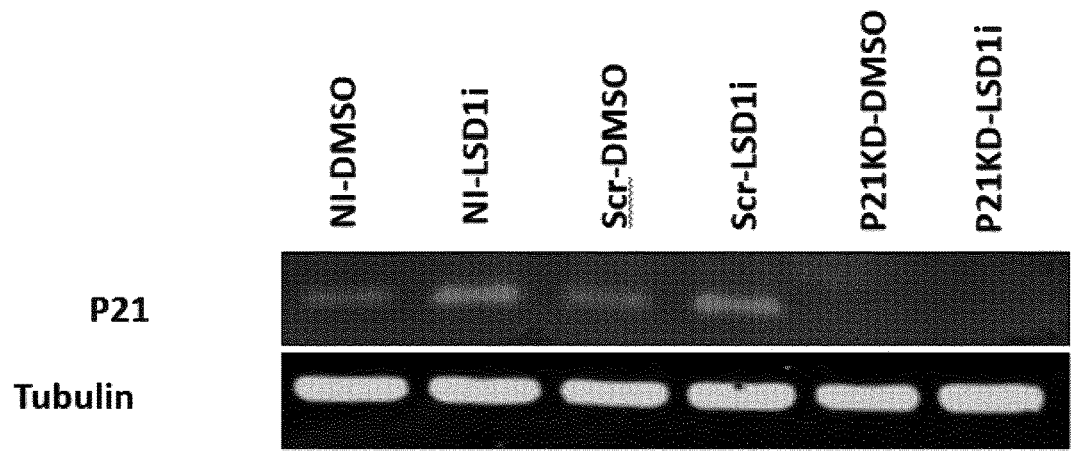
(FIG. 6A) Immunoblot of P21 in MC2580-treated UF1 cells.
Figure 6B:
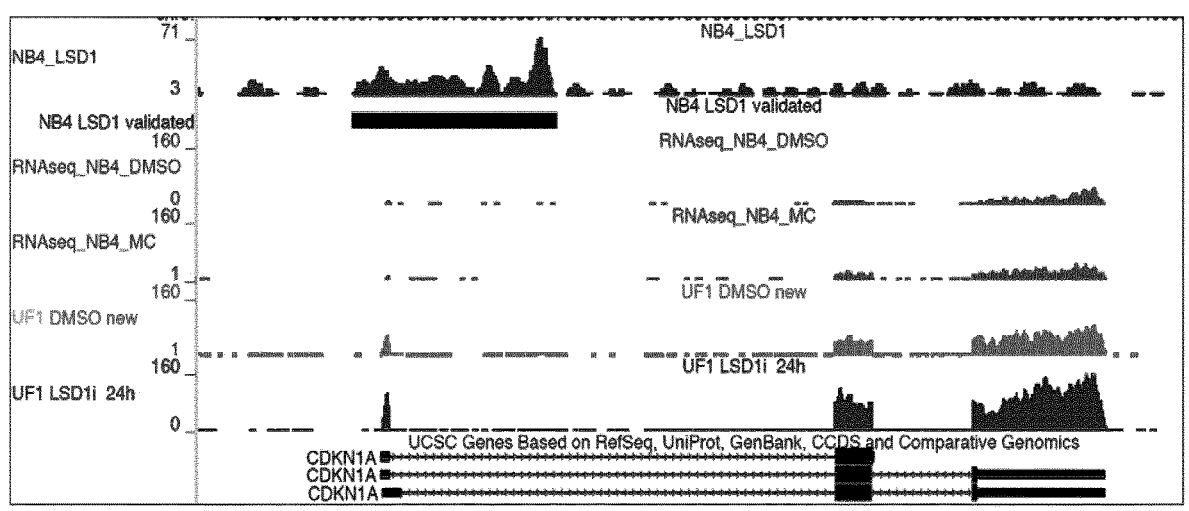
(FIG. 6B) MC2580 induces p21 expression in UF1 cells. (SCR=Scramble shRNA, NI=Not Infected, LSD1i=LSD1 inhibitor=MC2580).

Example 6. LSD1 Inhibition Leads to Further Upregulation of P21 RNA and Protein Level but not in P21KD Cells UF1 cells were treated with p21-shRNA, scramble shRNA (SCR), LSD1 inhibitor MC2580, p21-shRNA plus MC2580, scramble shRNA (SCR) plus MC2580. Non-infected (NI) UF1 cells were included as control. The p21 protein level in the treated cells was qualified using Western-blot and is shown in FIG. 6A. Immuno-blotting of tubulin was used as loading control. The p21 protein level was increased in the UF1 cells treated with MC2580 (FIG. 6A). p21 gene (CDKN1A) was expressed at a higher level in UF1 treated with MC2580 (FIG. 6B).

Figure 7A:
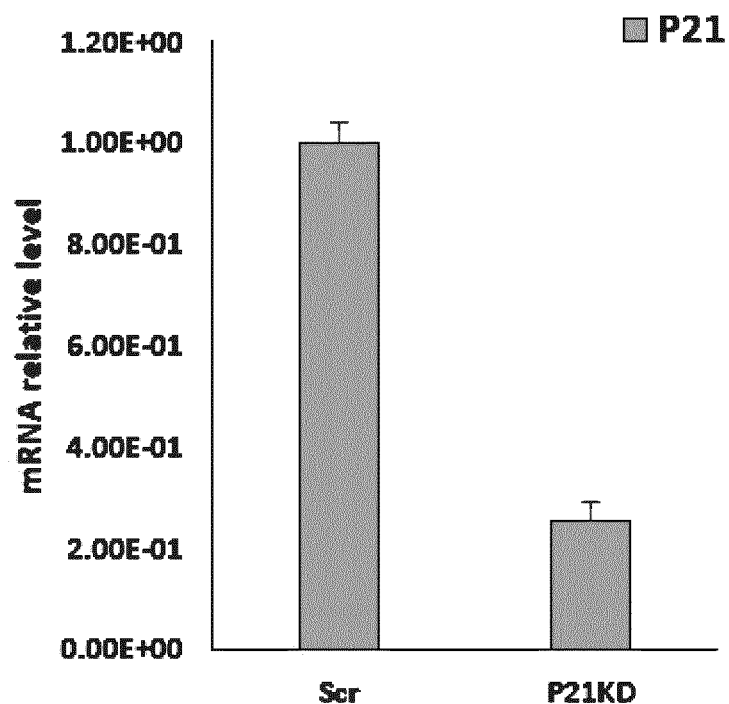
FIG. 7. Knockdown of p21 rescued Kasumi cells from cell growth inhibition, induction of differentiation and cell cycle arrest mediated by LSD1 inhibitor (FIG. 7A, FIG. 7B) Kasumi cell were infected with SCR (control) or P21 shRNA, and knockdown was monitored by qPCR and western blot.
(FIG. 7C) Relative proliferation of Kasumi cells infected with SCR (control) or p21 shRNA treated with MC2580.
(FIG. 7D) Representative light micrograph show Wright-Giemsa staining of Kasumi cells after 1 week treatment with indicated inhibitors.
(FIG. 7E) summary of cell-cycle status of Kasumi cells following 1 week treatment with indicated inhibitors.
(FIG. 7F) Immunoblot of P21 in MC2580-treated Kasumi cells. (SCR=Scramble shRNA, NI=Not Infected, LSD1i=LSD1 inhibitor-MC2580).
Figure 7B:
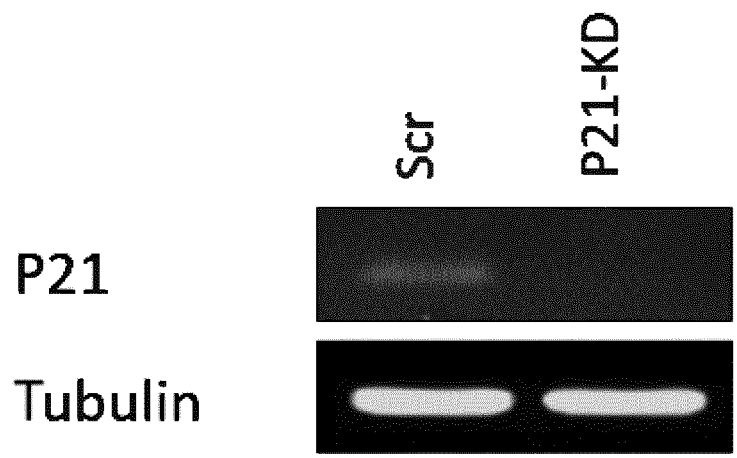

Example 7. Knockdown of p21 Rescued Kasumi Cells from Cell Growth Inhibition, Induction of Differentiation and Cell Cycle Arrest Mediated by LSD1 Inhibitor The p21 expression of Kasumi cells were knocked-down using shRNA oligos targeting p21 gene. The reduced p21 mRNA in the Kasumi cells treated with the oligos compared to control (SCR shRNA) was qualified using qPCR and is shown in FIG. 7A. The reduced p21 protein level in the Kasumi cells treated with the oligos compared to control (SCR shRNA) was qualified using Western-blot and is shown in FIG. 7B.

Figure 7C:
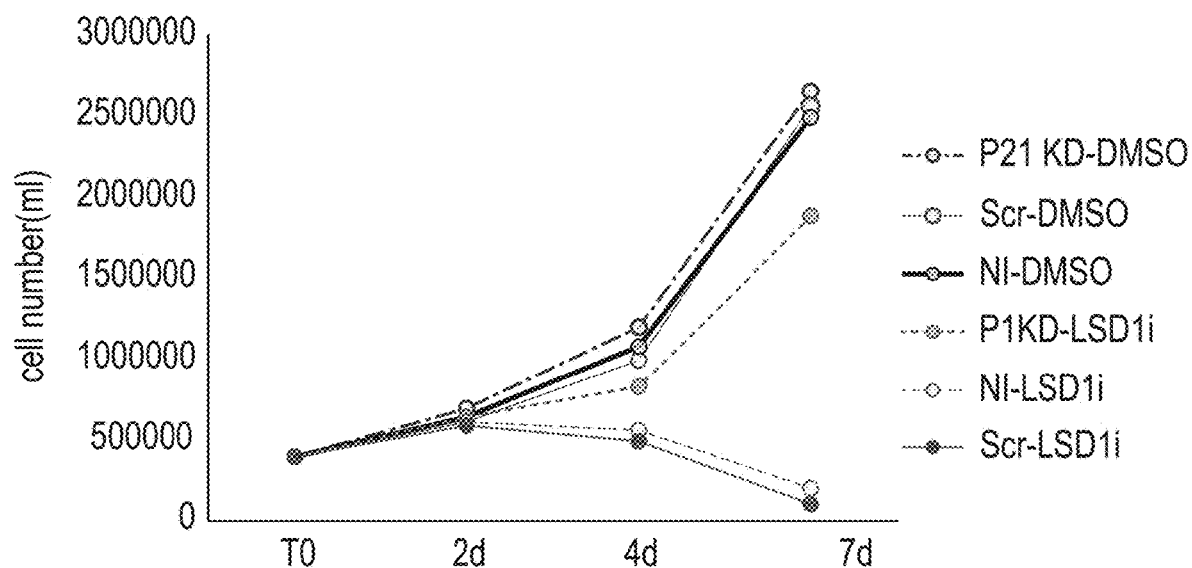
Figure 7D:
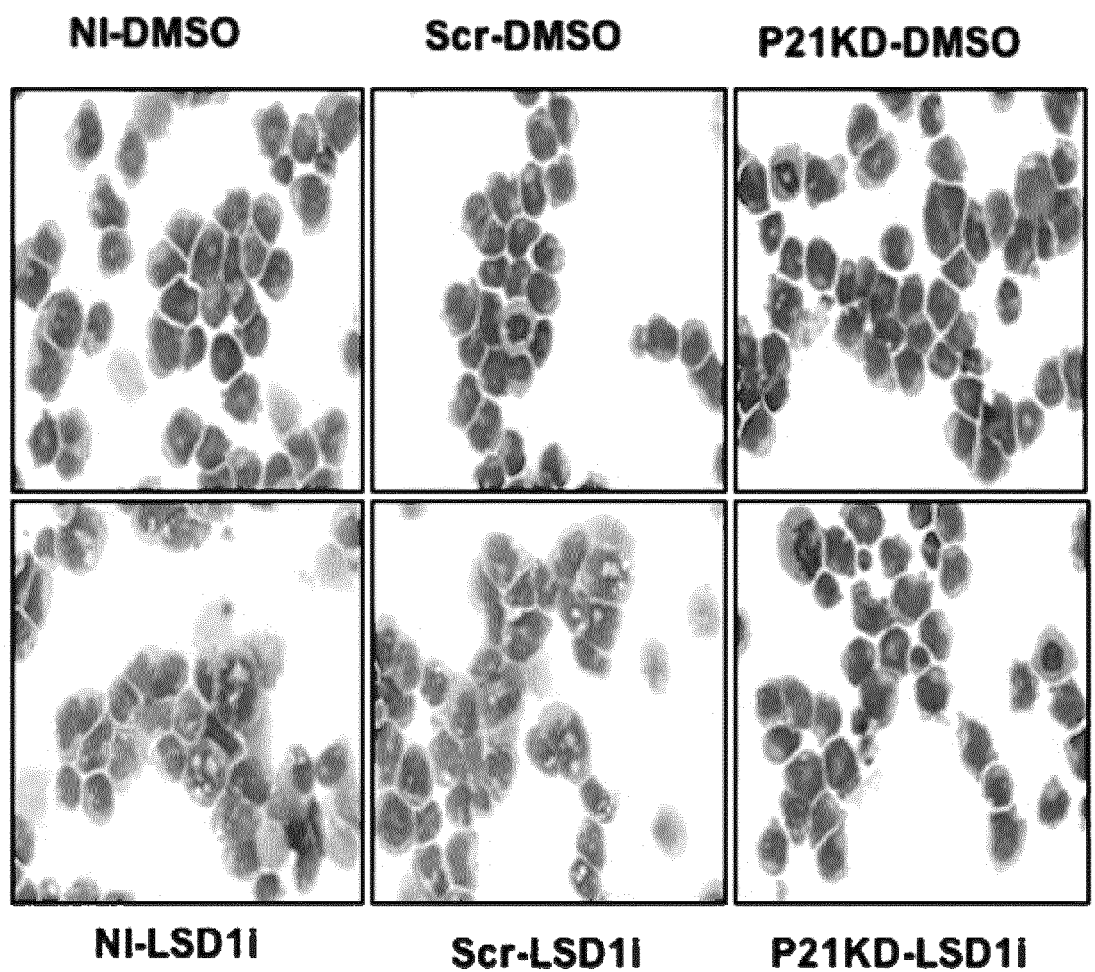
Figure 7E:
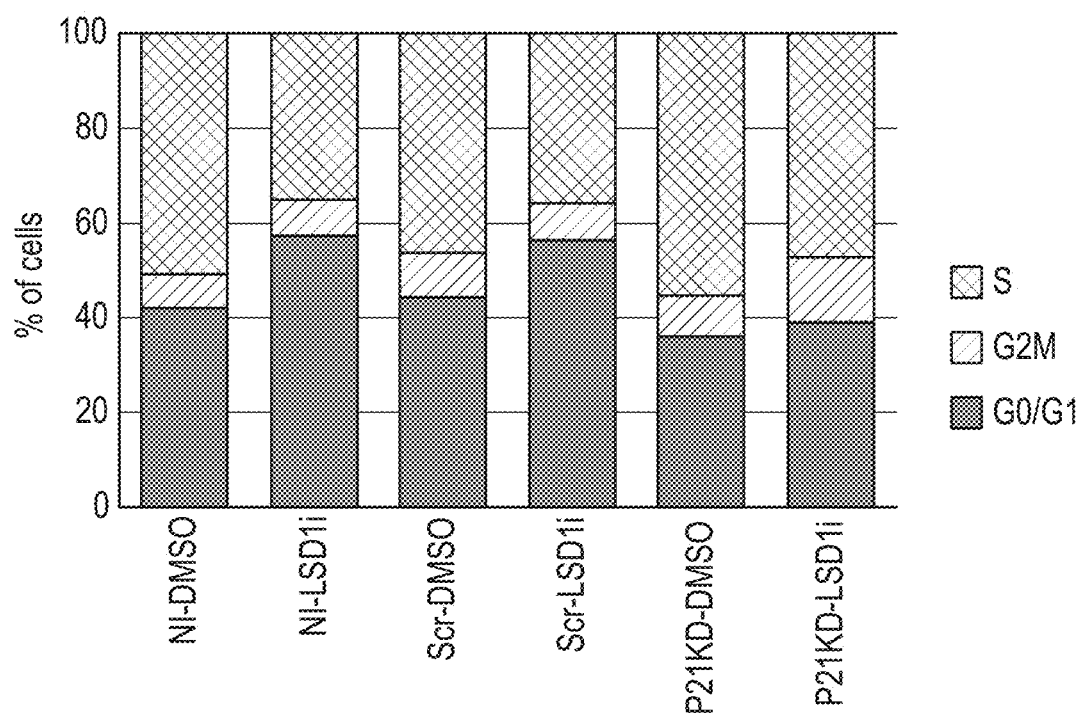
Figure 7F:
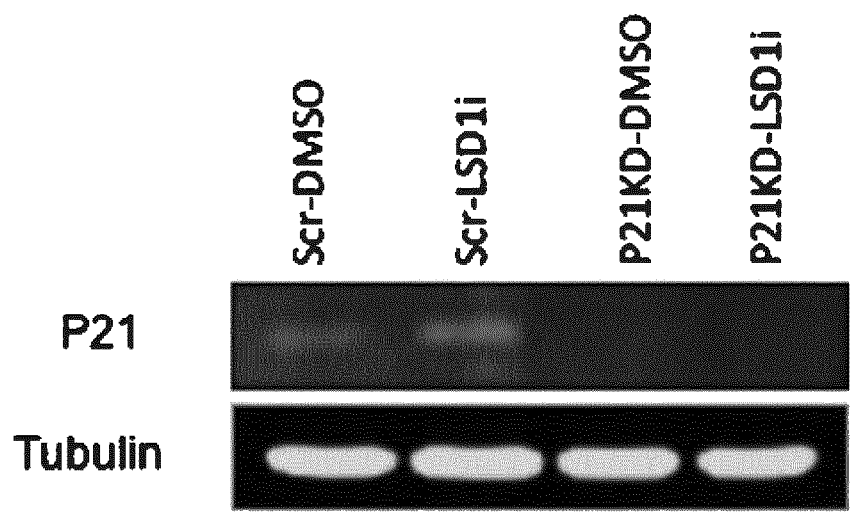

Kasumi cells were treated with p21-shRNA, scramble shRNA (SCR), LSD1 inhibitor MC2580, p21-shRNA plus MC2580, scramble shRNA (SCR) plus MC2580. Non-infected (NI) Kasumi cells were included as control. The proliferation of the treated cells were quantified before treatment and post-treatment from day 2, day 4, and day 7 (FIG. 7C). The cells following the 1 week treatment were analyzed under light micrographs using Wright-Giemsa staining (FIG. 7D). Cell cycle analysis were performed following the 1 week treatment. More Kasumi cells were arrested at the G0/G1 phase under LSD1 inhibitor treated conditions than cells under the other conditions. The cell cycle arrested was rescued in p21-shRNA treated cells (p21KD-DMSO) (FIG. 7E). Western-blot analysis showed that the p21 protein level was increased in the Kasumi cells treated with MC2580 (FIG. 6A).

Figure 8A:
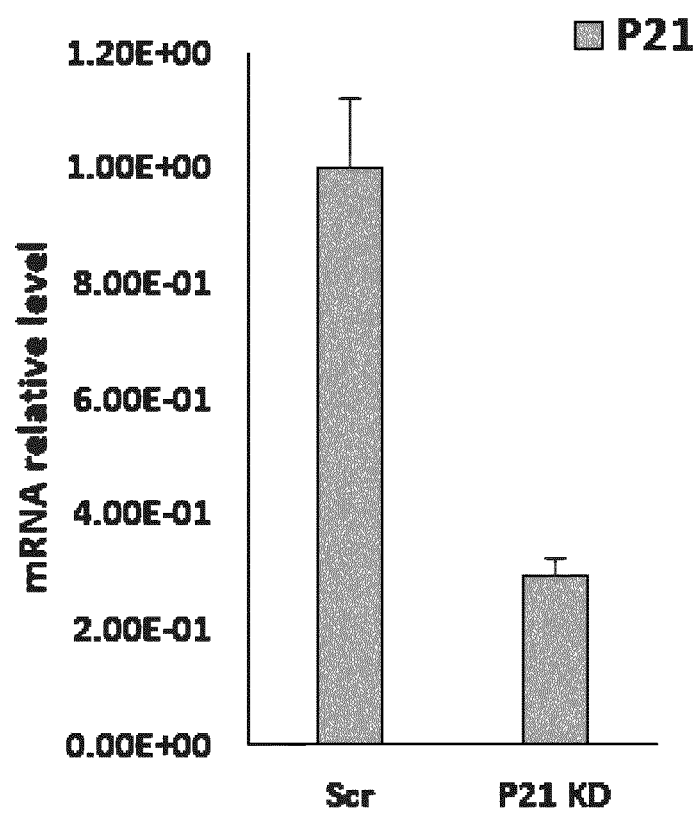
FIG. 8. Knockdown of p21 rescued small cell lung carcinoma NCI-H69 cells from cell growth inhibition, induction of differentiation and cell cycle arrest mediated by LSD1 inhibitor (FIG. 8A, FIG. 8B) NCI-H69 cell were infected with SCR (control) or P21 shRNA, and knockdown was monitored by qPCR.
(FIG. 8B) Relative proliferation of NCI-H69 cells infected with SCR (control) or p21 shRNA treated with MC2580.
(FIG. 8C) Summary of cell-cycle status of NCI-H69 cells following 10 days treatment with indicated inhibitors.
(FIG. 8D) Immunoblot of P21 in MC2580-treated NCI-H69 cells. (SCR=Scramble shRNA, NI=Not Infected, LSD1i=LSD1 inhibitor=MC2580).

Example 8. Knockdown of p21 Rescued Small Cell Lung Carcinoma NCI-H69 Cells from Cell Growth Inhibition, Induction of Differentiation and Cell Cycle Arrest Mediated by LSD1 Inhibitor The p21 expression of NCI-H69 cells were knocked-down using shRNA oligos targeting p21 gene. The reduced p21 mRNA in the NCI-H69 cells treated with the oligos compared to control (SCR shRNA) was qualified using qPCR and is shown in FIG. 8A.

Figure 8B:
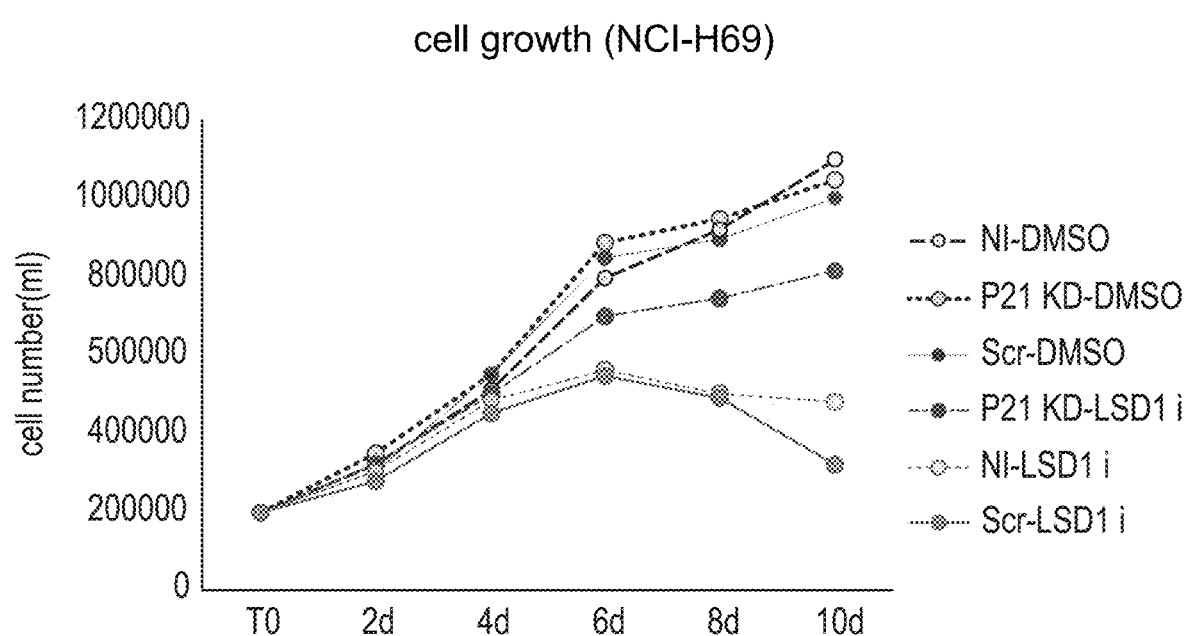
Figure 8C:
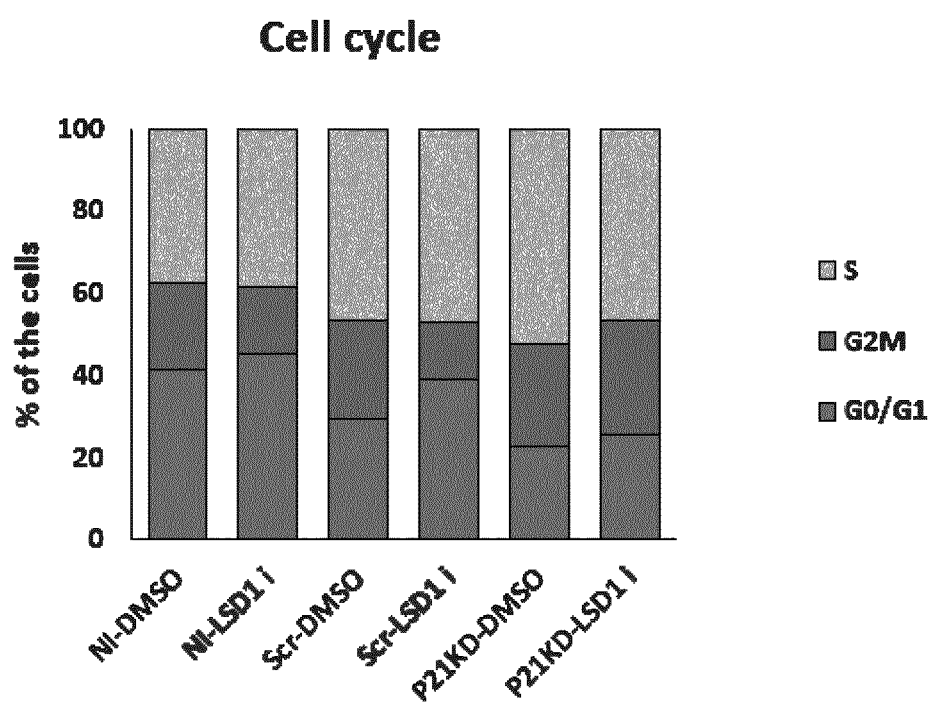
Figure 8D:
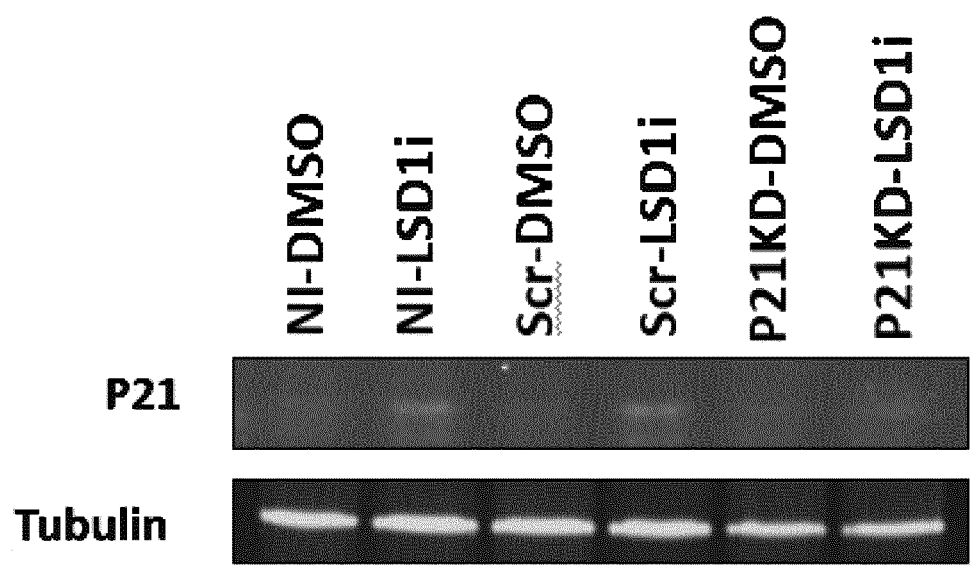

NCI-H69 cells were treated with p21-shRNA, scramble shRNA (SCR), LSD1 inhibitor MC2580, p21-shRNA plus MC2580, scramble shRNA (SCR) plus MC2580. Non-infected (NI) NCI-H69 cells were included as control. The proliferation of the treated cells were quantified before treatment and post-treatment from day 2, day 4, day 6, day 8, and day 10 (FIG. 8B). Cell cycle analysis were performed following the 1 week treatment. More NCI-H69 cells were arrested at the G0/G1 phase under LSD1 inhibitor treated conditions than cells under the other conditions. The cell cycle arrested was rescued in p21-shRNA treated cells (p21KD-DMSO) (FIG. 8C). Western-blot analysis showed that the p21 protein level was increased in the NCI-H69 cells treated with the MC2580 (FIG. 8D).

Example 9. HDAC Inhibitors Induced p21 Expression

Figure 9A:
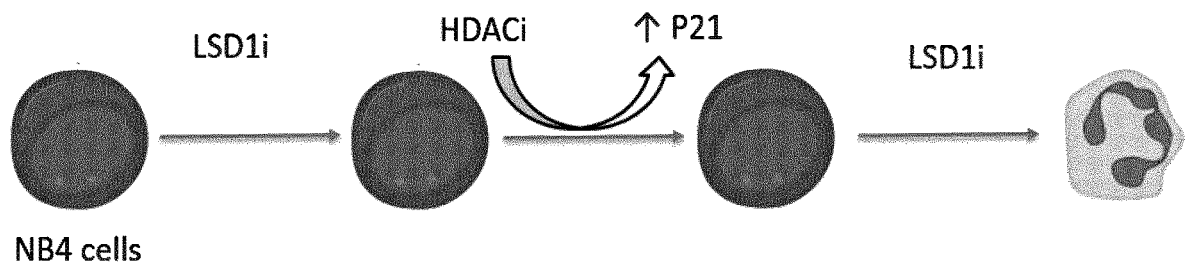
FIG. 9. HDAC is (SAHA,TSA) induce p21 expression (FIG. 9A) Schematic representation of co-treatment of HDAC is with MC2580 in NB4 cells.
(FIG. 9B) NB4 cells were infected with SCR (control) or P21 shRNA, and knockdown was monitored by qPCR. Values are normalized against GAPDH.
(FIG. 9C) Monitoring of p21 expression upon the indicated treatments. (SCR=Scramble shRNA, NI=Not Infected, HDACi=HDAC inhibitor=SAHA or TSA).
Figure 9B:
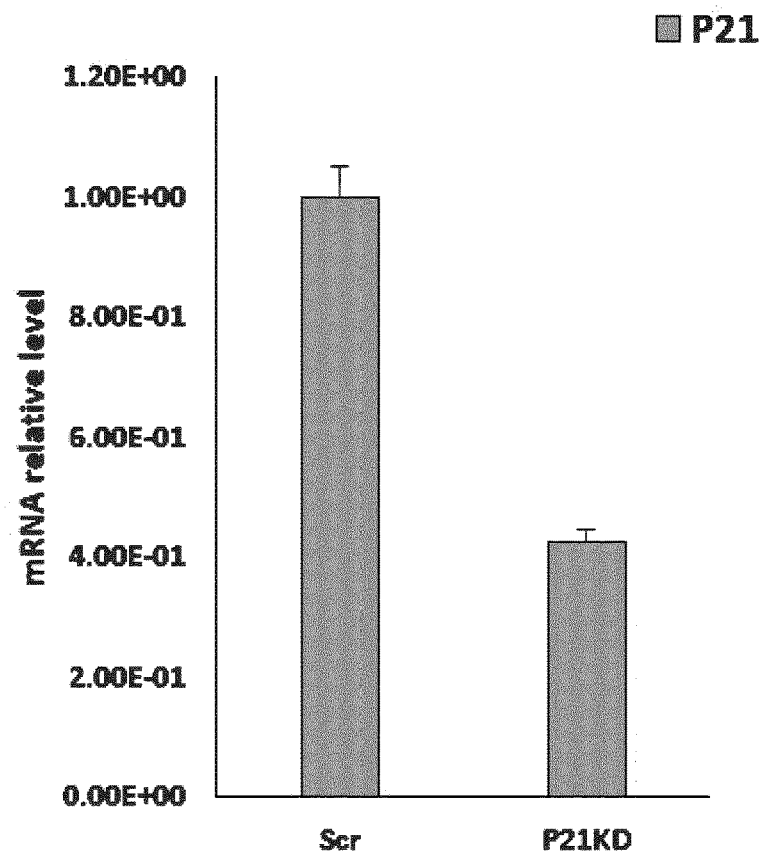

HDAC inhibitors are known to increase p21 expression. The p21 expression of NB4 cells were knocked-down using shRNA oligos targeting p21 gene. The reduced p21 mRNA in the NB4 cells treated with the oligos compared to control (SCR shRNA) was qualified using qPCR and is shown in FIG. 9B.

Figure 9C:
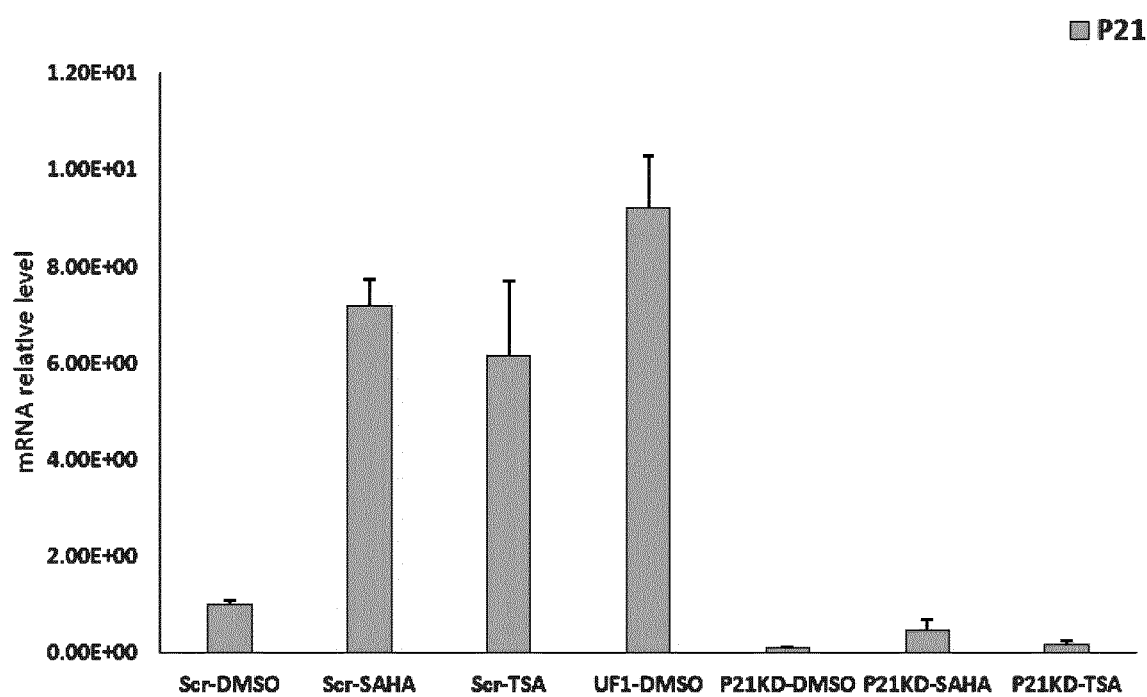

NB4 cells were treated with HDAC inhibitors, trichostatin A (TSA) and suberoylanilide hydroxamic acid (SAHA), in combination with p21-shRNA or scramble shRNA (SCR). NB4 cells with p21 knock-down without HDAC inhibitor treatment (p21KD-DMSO), NB4 cells without p21 knock-down and without HDAC inhibitor treatment (Scr-DMSO), untreated UF1 cells (UF1-DMSO) were included as control. FIG. 9C demonstrates that the HDAC inhibitors induced p21 expression in NB4 cells.

Figure 10B:
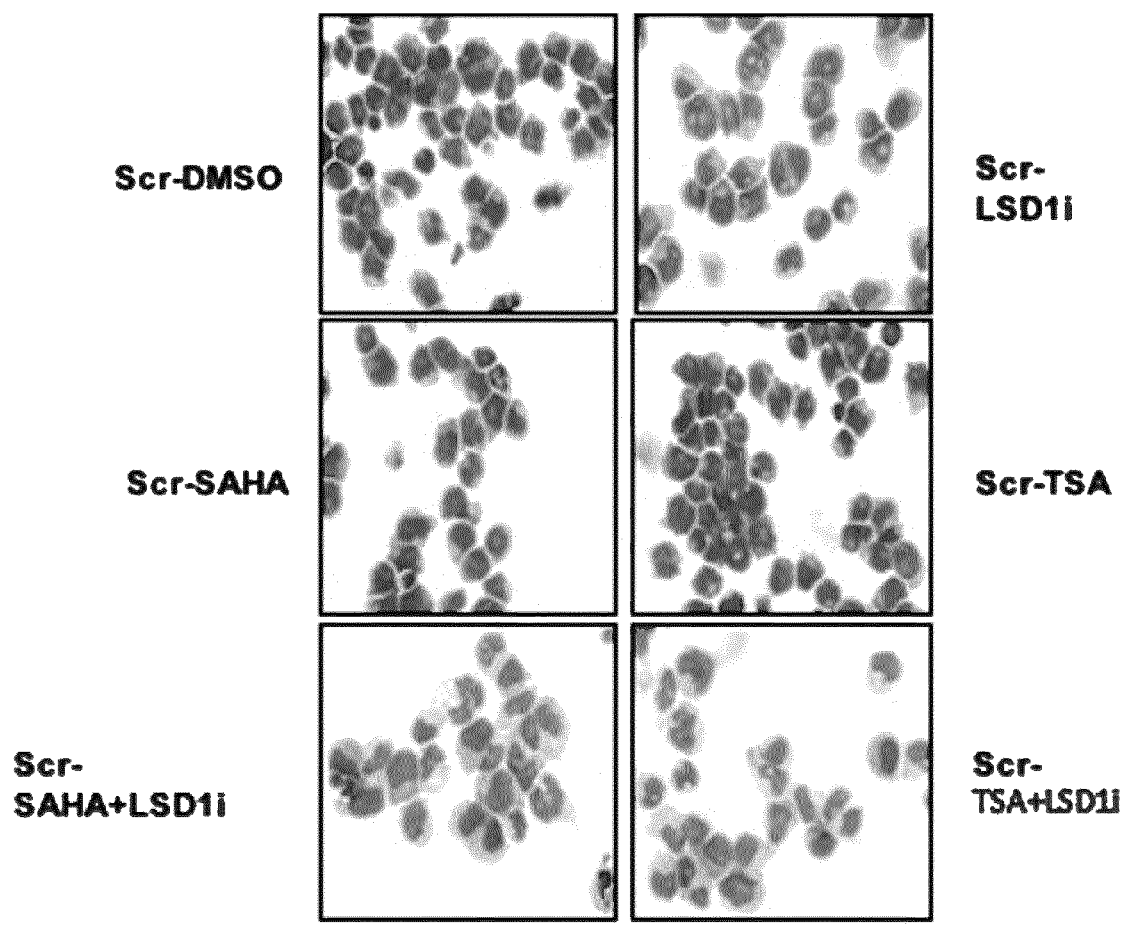
(FIG. 10B and FIG. 10C) Representative light micrograph show Wright-Giemsa staining of NB4 cells infected with SCR (control) or p21 shRNA and treated with HDAC inhibitor and/or MC2580.
Figure 10C:
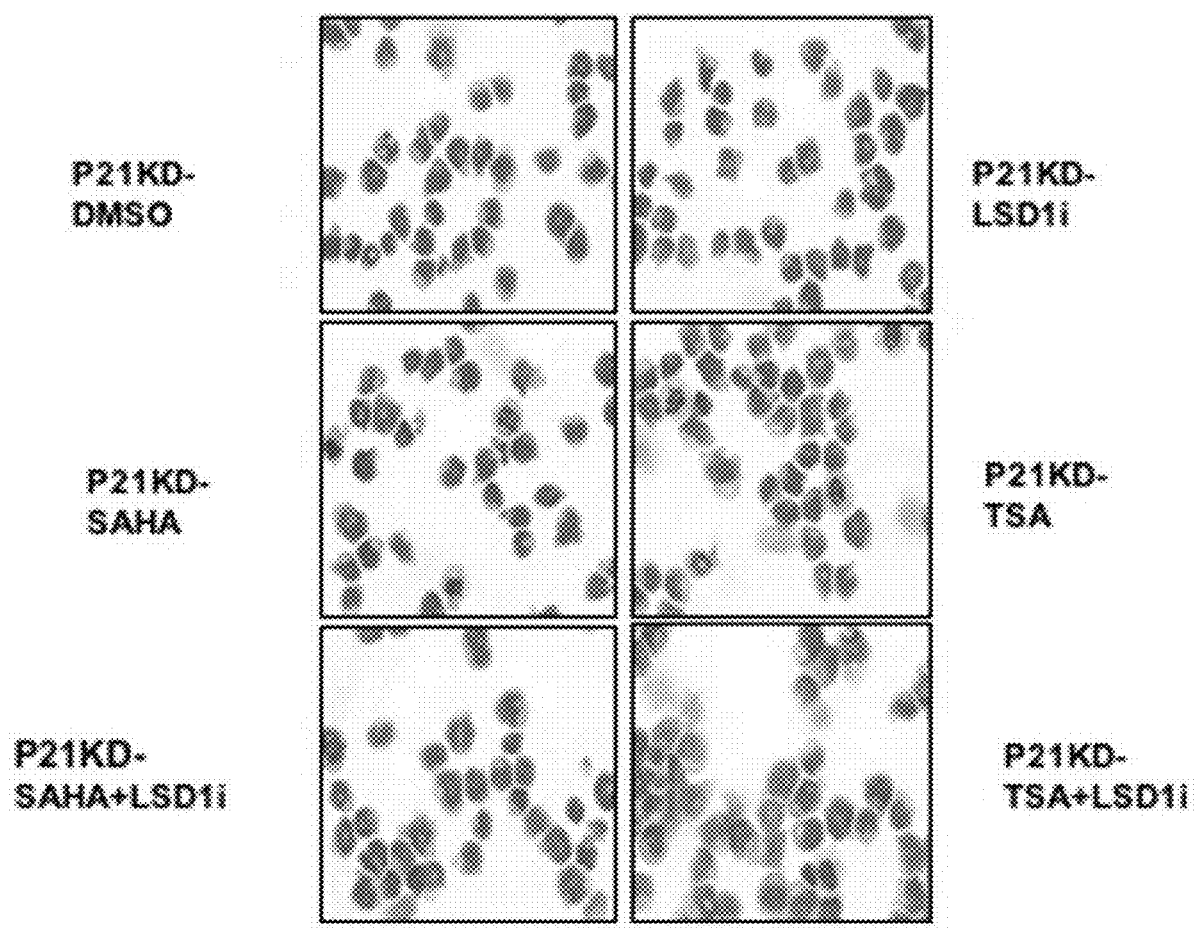
Figure 10D:
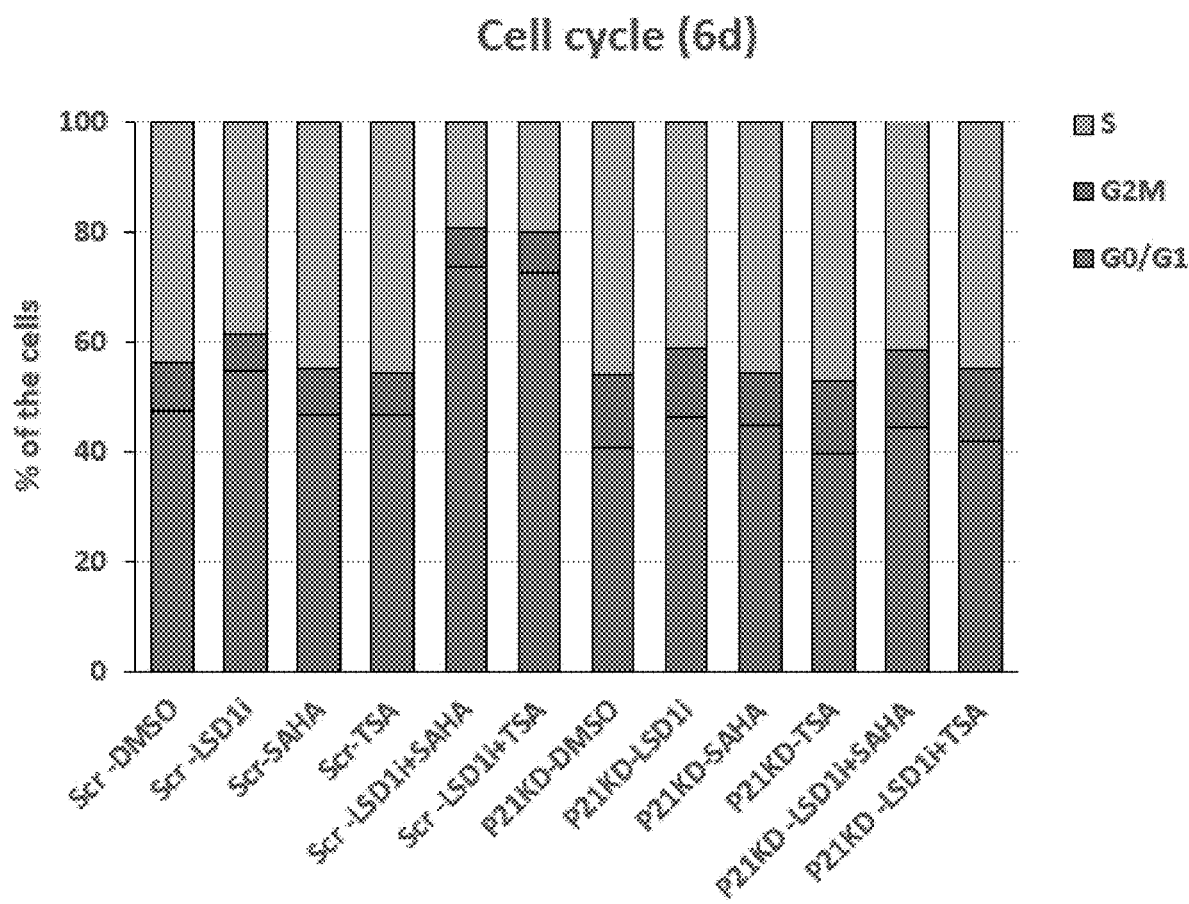
(FIG. 10D) Summary of cell-cycle status of NB4 cells infected with SCR (control) or p21 shRNA and treated with HDAC inhibitor and/or MC2580. (SCR=Scramble shRNA, NI=Not Infected, LSD1i=LSD1 inhibitor=MC2580).

Example 10. P21 Induction by HDAC Inhibitors Sensitized NB4 Cells to LSD1 Inhibitors NB4 cells were treated with HDAC inhibitors, trichostatin A (TSA) and suberoylanilide hydroxamic acid (SAHA), in combination with p21-shRNA or scramble shRNA (SCR), with or without LSD1 inhibitor MC2580. NB4 cells with p21 knock-down without HDAC inhibitor treatment (p21KD-DMSO), NB4 cells without p21 knock-down and without HDAC inhibitor treatment (Scr-DMSO) were included as control. The proliferation of the treated cells were quantified before treatment and post-treatment from day 2, day 4, and day 6 (FIG. 10A). The treated cells were analyzed under light micrographs using Wright-Giemsa staining (FIG. 10B and FIG. 10C). Cell cycle analysis were performed following the 1 week treatment. More NB4 cells were arrested at the G0/G1 phase under LSD1 inhibitor treated conditions than untreated control cells (Scr-DMSO). Further G0/G1 phase arrest was observed in the cells treated with both LSD1 inhibitor and HDAC inhibitors. The cell cycle arrested was rescued in p21-shRNA treated cells (FIG. 10D).

Example 11. CDK4/6 Inhibitor Palbociclib Sensitized NB4 Cells to LSD1 Inhibitor

The p21 expression of NB4 cells were knocked-down using shRNA oligos targeting p21 gene.

Figure 11A:
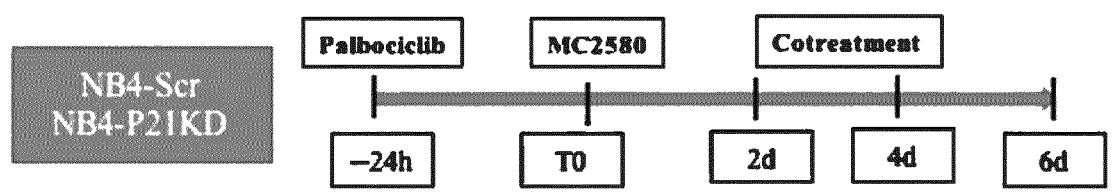
(FIG. 11A) Schematic representation of co-treatment of palbociclib with MC2580 in NB4 cells infected by P21 shRNA and SCR (Control).
Figure 11B:
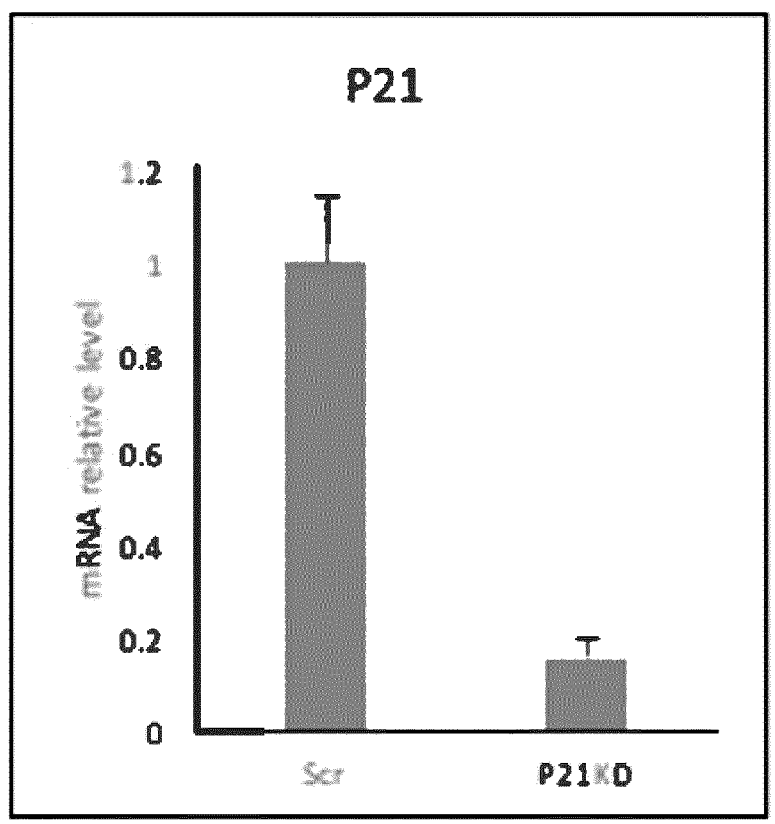
(FIG. 11B) NB4 cells were infected with SCR(control) or P21 shRNA, and knockdown was monitored by qPCR.

Scrambled shRNA (NB4-SCR) was used as control (FIG. 11B). These cells were treated with CDK4/6 inhibitor palbociclib for 24 hours before MC2580 was added. The schematic representation of the co-treatment is shown in FIG. 11A.

Figure 11C:
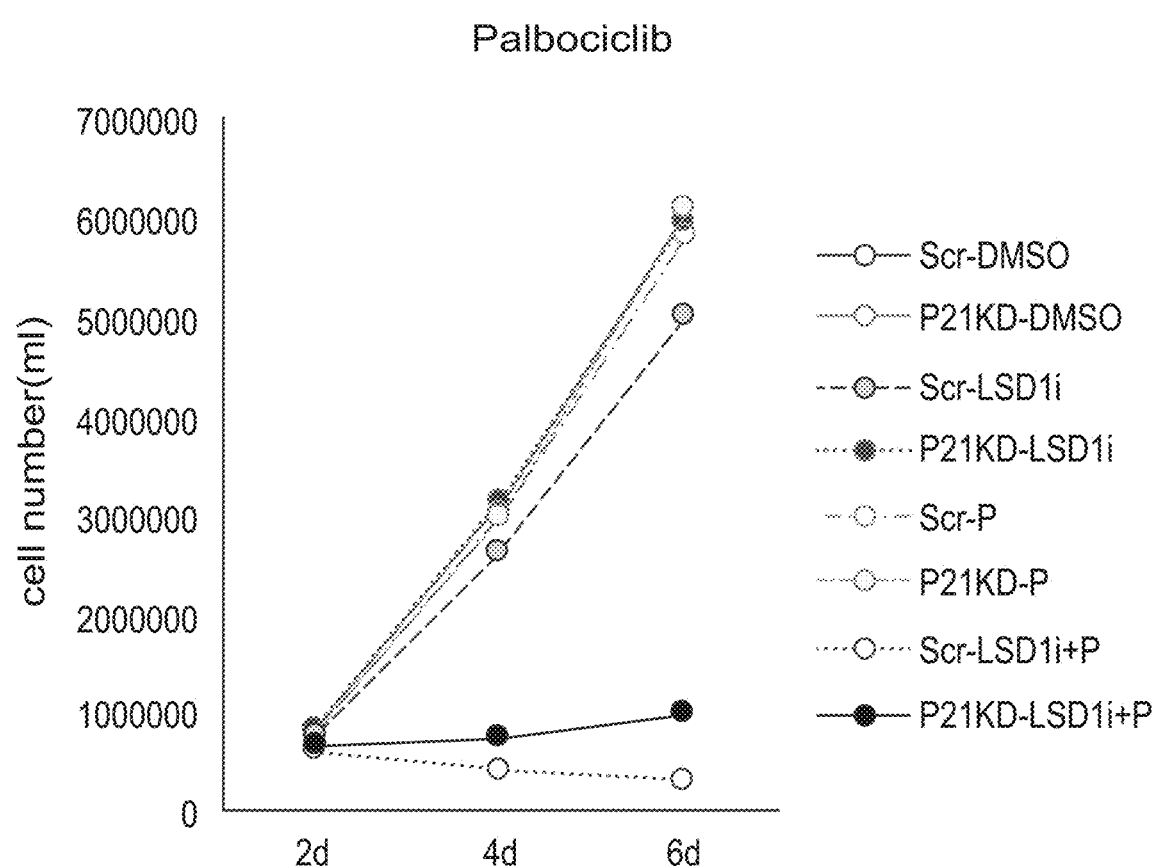
(FIG. 11C) Relative proliferation of NB4 cells infected with SCR (control) or p21 shRNA and treated with palbociclib and/or MC2580.
Figure 12:
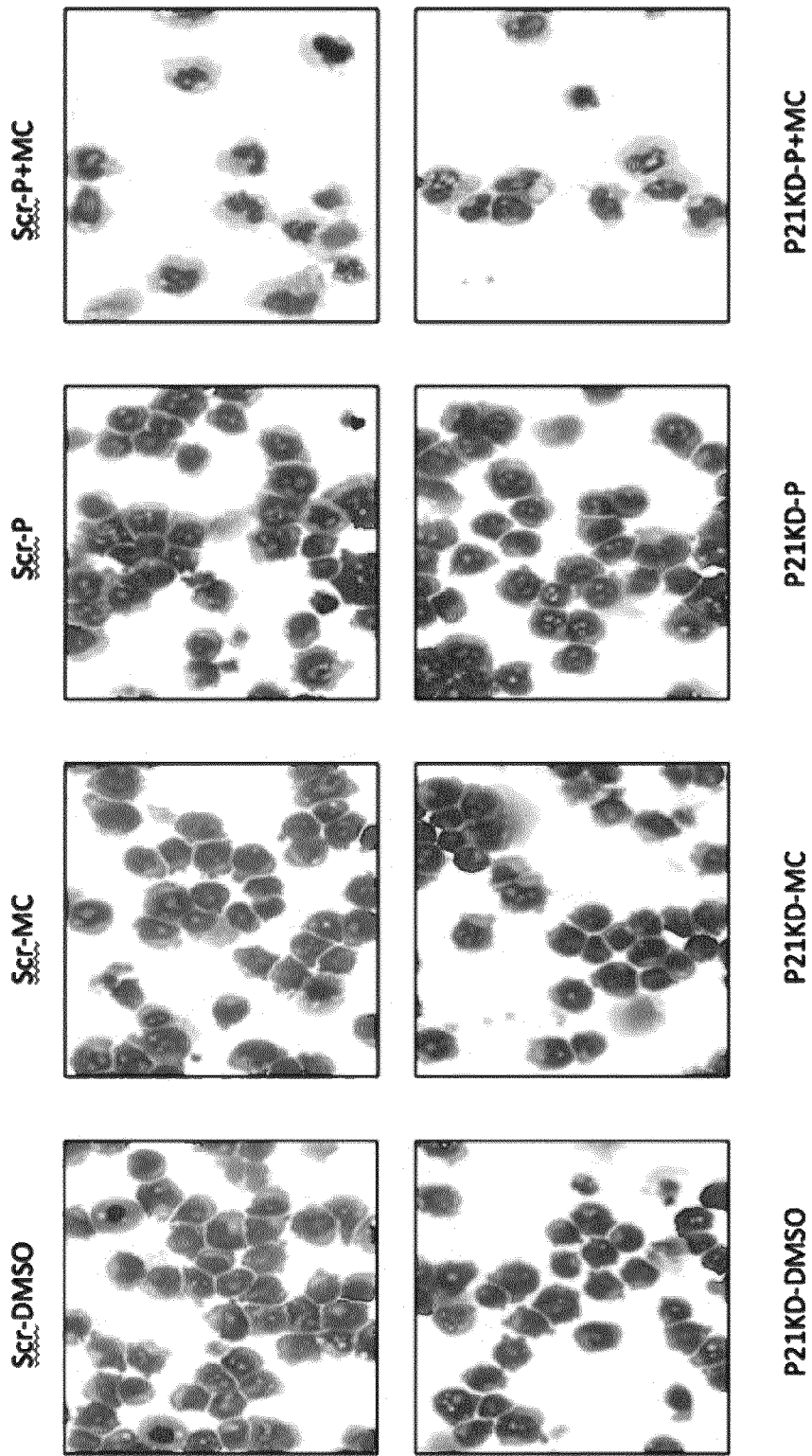
FIG. 12. Palbociclib (CDK4/6 inhibitor) sensitizes NB4 cells to LSD1 inhibitor. Representative light micrograph show Wright-Giemsa staining of NB4 cells infected with SCR (control) or p21 shRNA and treated with palbociclib and/or MC2580. (SCR=Scramble shRNA, NI=Not Infected, LSD1i=LSD1 inhibitor=MC2580, P=palbociclib).

NB4 cells were treated with p21-shRNA, scramble shRNA (SCR), LSD1 inhibitor MC2580, p21-shRNA plus MC2580, scramble shRNA (SCR) plus MC2580. These cells were treat with or without palbociclib (P). The proliferation of the treated cells were quantified before treatment and post-treatment from day 2, day 4, and day 6 (FIG. 11C). Cell cycle analysis were performed following the 6-day treatment. NB4 cells treated with both MC2580 and palbociclib have significantly more cells arrested at the G0/G1 phase regardless whether p21 expression was knocked-down (FIG. 11E). Apoptosis of the treated cells was analyzed using propidium iodide (PI)/Annexin staining. NB4 cells treated with both MC2580 and palbociclib have significantly more cells undergo apoptosis regardless whether p21 expression was knocked-down (FIG. 11D). The treated cells were analyzed under light micrographs using Wright-Giemsa staining (FIG. 12).

Figure 13:
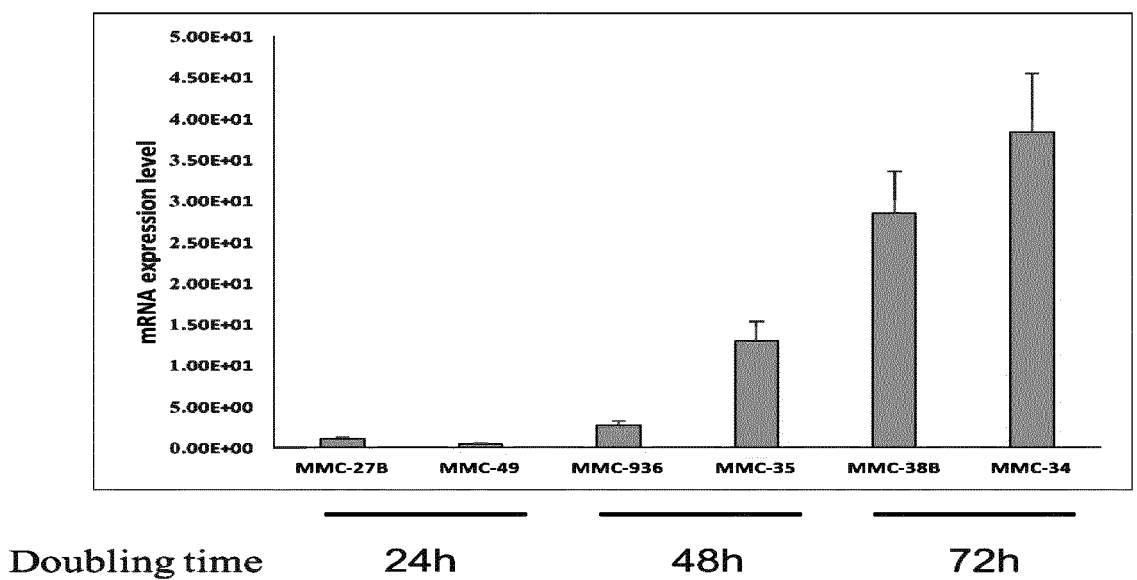
FIG. 13 depicts the p21 mRNA levels of six primary human melanoma cell lines (MMC-27B, MMC-49, MMC-936, MMC-35, MMC-38B, MMC-34) and the doubling time of these cell lines. The expression levels of p21 were normalized against GAPDH expression levels.

Example 12. Slow-Cycling Melanoma Cells have Higher Levels of p21 and are More Sensitive to LSD1 Inhibitor The p21 mRNA levels of six primary human melanoma cell lines (MMC-27B, MMC-49, MMC-936, MMC-35, MMC-38B, MMC-34) were analyzed. The expression levels were normalized against GAPDH expression levels. The doubling time of these cell lines were also measured. As shown in FIG. 13, the slow-cycling melanoma cell lines have higher expression level of p21 than those cell lines having a shorter doubling time.

Figure 14:
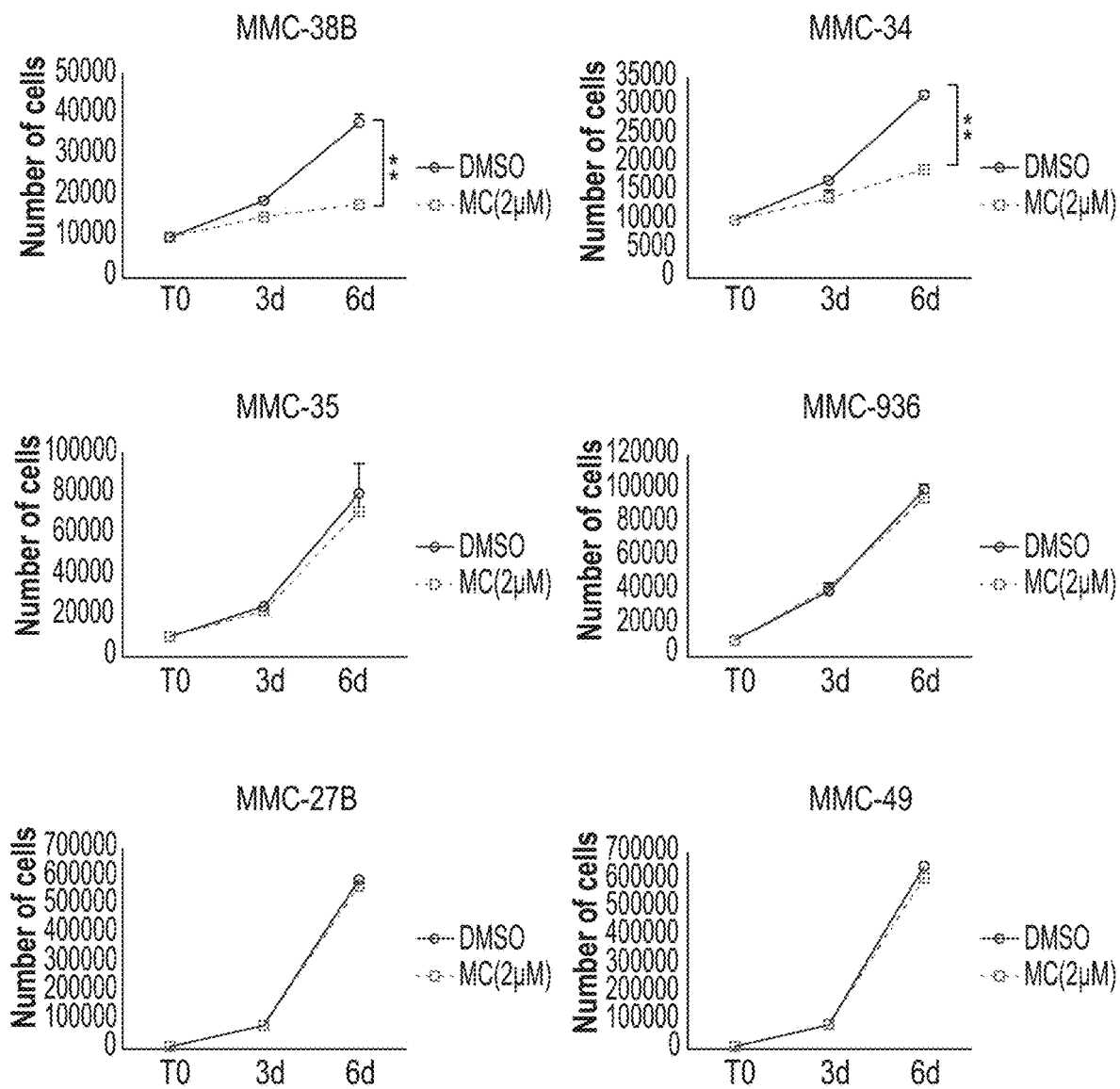
FIG. 14 depicts the proliferation of six primary human melanoma cell lines (MMC-27B, MMC-49, MMC-936, MMC-35, MMC-38B, MMC-34) over 6 days with or without treatment of LSD1 inhibitor MC2580 (2 µM) was analyzed. "MC" stands for MC2580 treated cells. "DMSO" stands for control cells treated with DMSO.

The proliferation of six primary human melanoma cell lines (MMC-27B, MMC-49, MMC-936, MMC-35, MMC-38B, MMC-34) over 6 days with or without treatment of an LSD1 inhibitor (MC2580) was analyzed. "MC" stands for MC2580 treated cells. Control cells ("DMSO") were treated with DMSO. As shown in FIG. 14, the proliferation of the slow-cycling melanoma cell lines (MMC-38B, MMC-34) were more affected by the LSD1 inhibitor treatment than those cell lines having a shorter doubling time.

Example 13. Effects Mediated by LSD1 Inhibition in Human Primary Melanoma Cells is p21-Dependent Cell cycle analysis was performed for two primary human melanoma cell lines (MMC-38B, MMC-34) with p21 knock-down using shRNA ("p21-KD") or treated with control shRNA ("SCR"). The reduction in p21 expression level in these cells is shown in FIG. 15A. As shown in FIG. 15B, the p21 knock-down cells had a higher percentage in the S phase than the control cells.

MMC-38B and MMC-34 cells were treated with p21-shRNA ("P21KD-DMSO"), scramble shRNA ("SCR-DMSO"), scramble shRNA plus LSD1 inhibitor (MC2580) ("SCR-LSD1i"), or p21-shRNA plus MC2580 ("P21KD-LSD1i"). The proliferation of these cells over 6 days was analyzed and shown in FIG. 16A. The cell cycle analysis of these cells is shown in FIG. 16B. The reduction of p21 expression in p21 knock-down cells was confirmed using immunoblotting analysis as shown in FIG. 16C. Tubulin was used as a loading control. The data suggests that inhibition of LSD1 induced cell growth inhibition, cell cycle arrest, increase of p21 expression in the human primary melanoma cells, and these effects of LSD1 inhibition were rescued by p21 knock-down.

Figure 17:
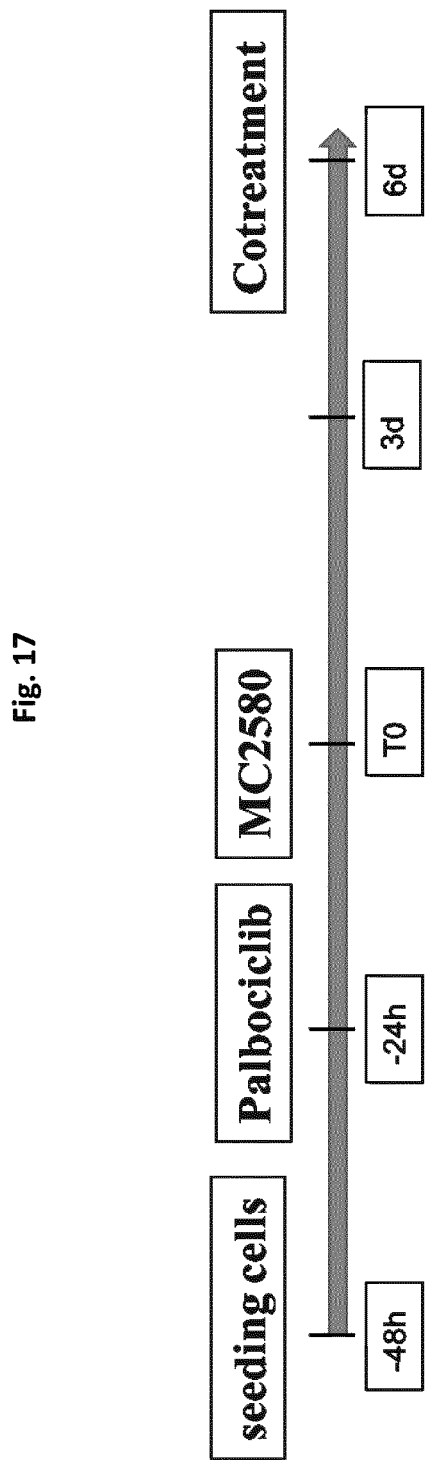
FIG. 17 is a schematic representation of co-treatment of palbociclib with LSD1 inhibitor in melanoma cells.
Figure 18:
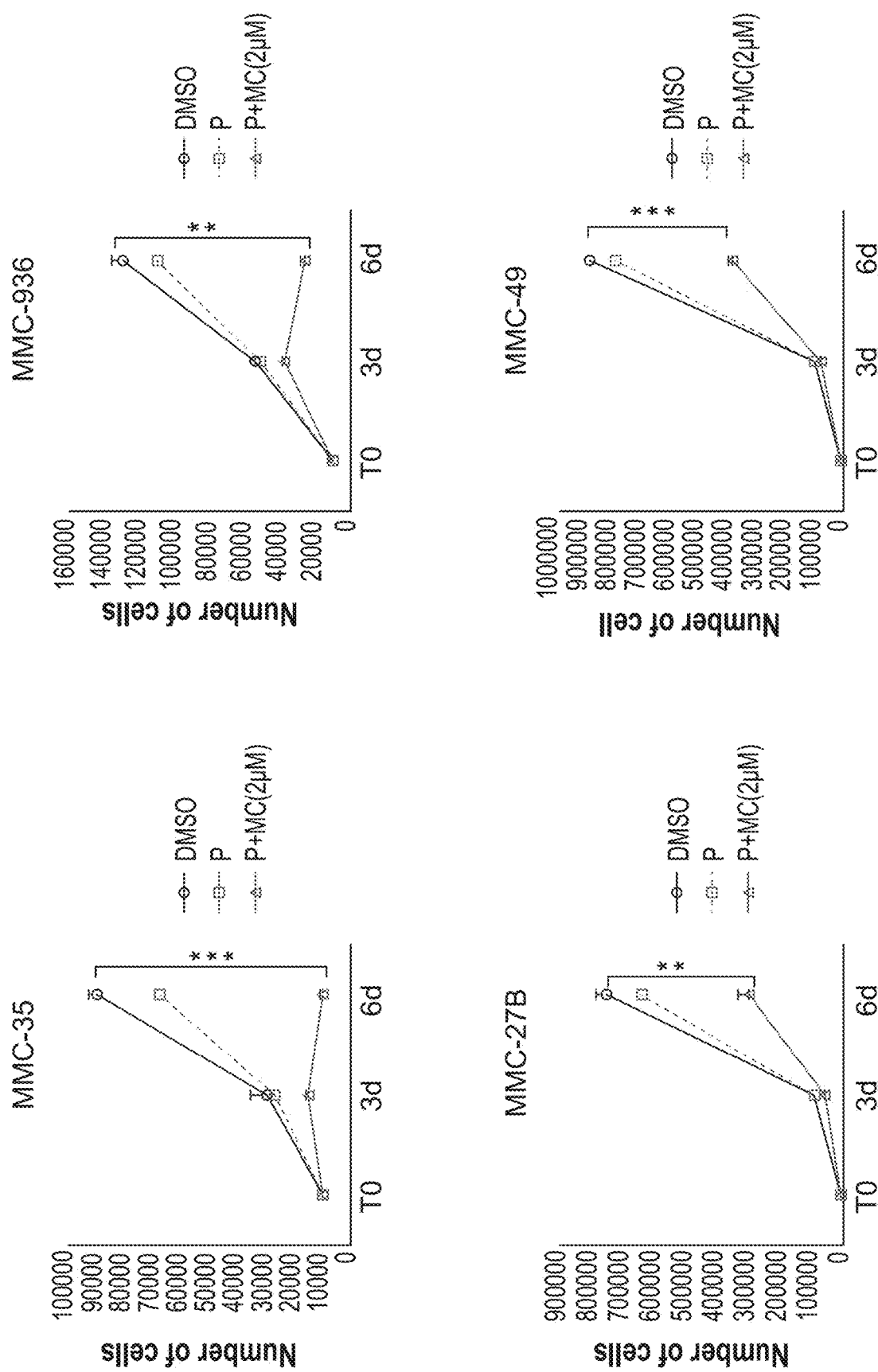
FIG. 18 depicts relative proliferation of treated-melanoma cells with palbociclib for 24 h following co-treatment with MC2580 or DMSO. Data are presented as mean of triplicates±SD. P value<0.05 (*), P<0.01 () and P<0.001 (*).

Example 14. Forced Cell Cycle Inhibition Sensitizes Resistant Primary Melanoma Cells to LSD1 Inhibitor As the schematic in FIG. 17 shows, melanoma cells were treated with palbociclib starting 24 hours after being seeded. MC2580 (2 µM) was then added to the cells 24 hours after palbociclib being added. The co-treatment of palbociclib and MC2580 ("P+MC") lasted 6 days. The proliferation of the treated melanoma cells (MMC-27B, MMC-49, MMC-936, MMC-35) was analyzed during the 6 days of co-treatment and shown in FIG. 18. Melanoma cells treated with palbociclib alone ("P") and DMSO ("DMSO") were included as control.

Figure 19:
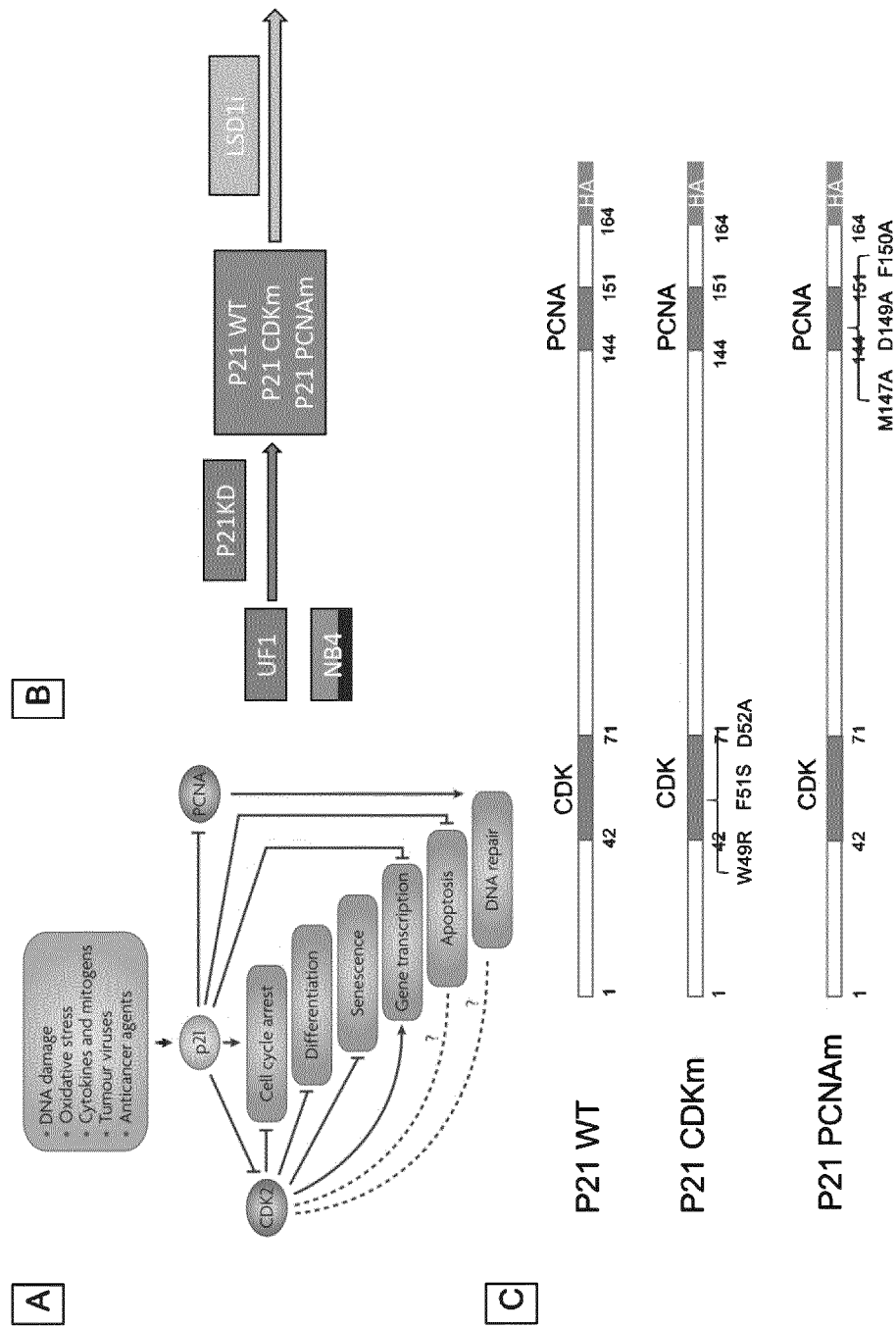
FIG. 19A is a reproduction of a figure illustrating the central role of p21 in sensing and responding to a plethora of stimuli from Abbas et al., Nat Rev Cancer. 9(6):400-14 (2009). p21 responds to a variety of stimuli to promote growth-inhibitory activities that depend primarily on its ability to inhibit the kinase activity of cyclin-dependent kinase 2 (CDK2). p21-induced cell cycle arrest also depends on its ability to inhibit CDK1. p21 can inhibit cellular proliferation independent of CDK2 inhibition by inhibiting proliferating cell nuclear antigen (PCNA), which is required for S phase progression.
FIG. 19B is a schematic representation of an experiment in which the P21 expression in UF1 cells and NB4 cells were suppressed using p21 knock-down ("P21KD") and then various expression constructs (p21-WT, p21-CDK mutant, or p21-PCNA mutant) were introduced into these cells.
FIG. 19C is a schematic representation of the expression constructs of p21-WT, p21-CDK mutant and p21-PCNA mutant.

Example 15. P21 by Binding to CDK Leads to Cell Cycle Arrest and Sensitizes Cells to LSD1 Inhibitor As the schematic in FIG. 19B shows, the P21 expression in UF1 cells and NB4 cells were suppressed using p21 knock-down ("P21KD"). Then various expression constructs (p21-WT, p21-CDK mutant, or p21-PCNA mutant) were introduced into these cells. FIG. 19C illustrates the expression constructs (p21-wild type, p21-CDK mutant, or p21-PCNA mutant). It has been reported that the p21-CDK mutant construct has mutations in the binding site for CDKs (W49R/F51S/D52A), whereas the p21-PCNA mutant construct has mutations in the PCNA-binding site (M147A/D149A/F150A). (Kim et al. "The Stress-activated Protein Kinases p38a and JNK1 Stabilize p21(Cip1) by Phosphorylation," J. BIOL. CHEM. 277(33): 29792-29802 (2002).)

Figure 20A:
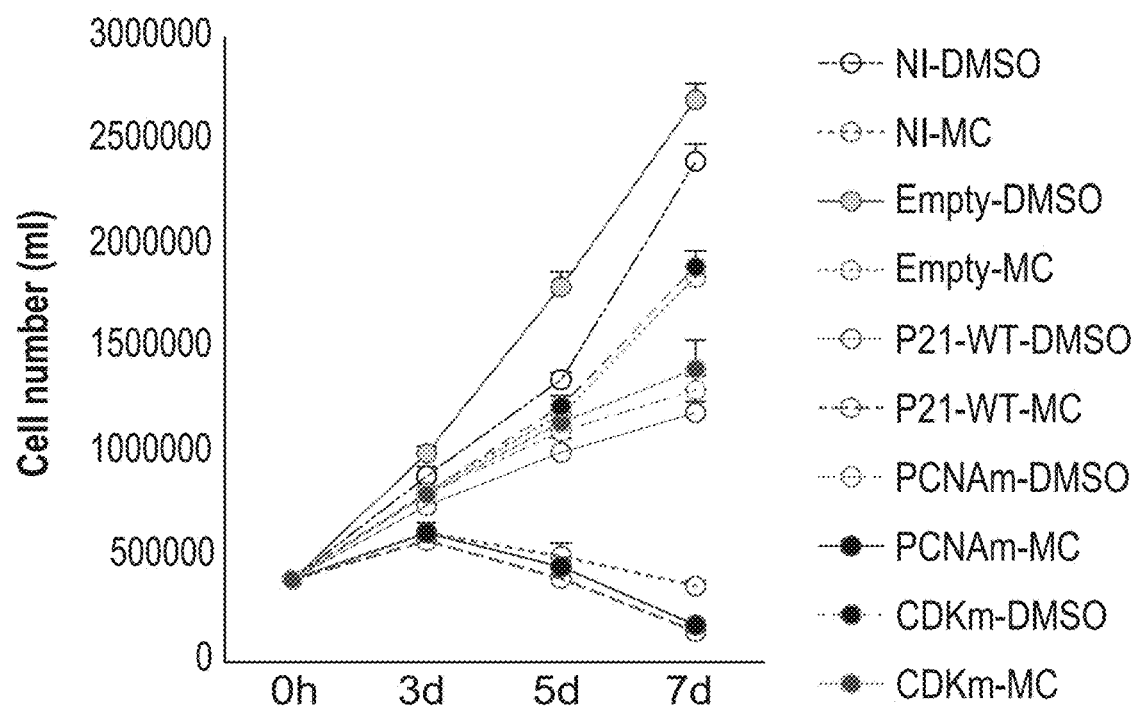
FIG. 20A depicts relative proliferation of UF1 cells stably transduced with shRNA targeting p21 following transfection with empty or p21-WT, p21-PCNAm, p21-CDKm expression vector following treatment with MC2580 or DMSO. Data are presented as mean of triplicates±SD.
Figure 20B:
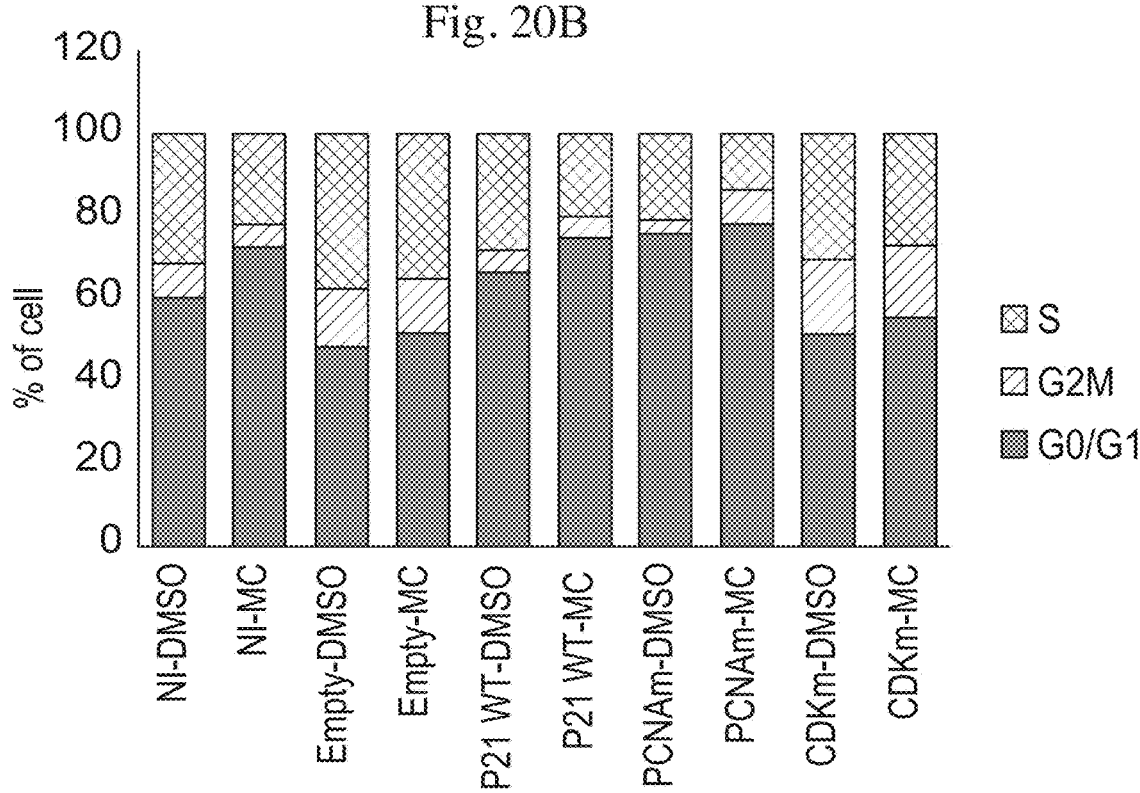
FIG. 20B depicts cell-cycle status of UF1 cells stably transduced with shRNA targeting p21 following transfection with empty or p21-WT, p21-PCNAm, p21-CDKm expression vector following treatment with MC2580 or DMSO.
Figure 21A:
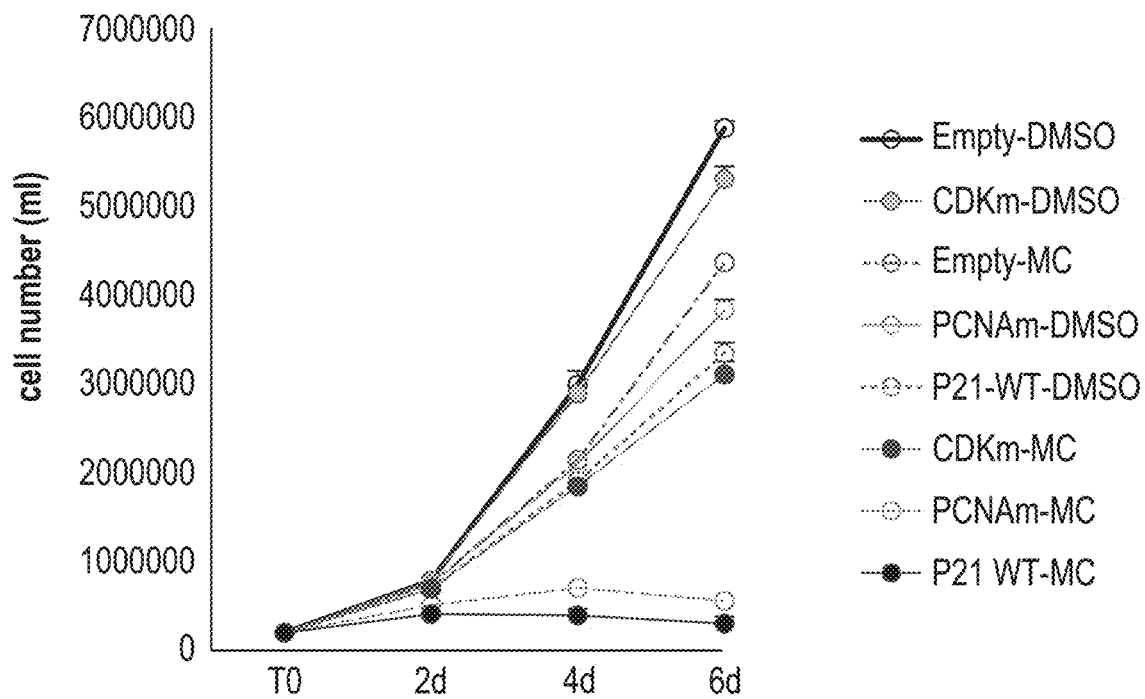
FIG. 21A depicts relative proliferation of NB4 cells stably transduced with shRNA targeting p21 following transfection with empty or p21-WT, p21-PCNAm, p21-CDKm expression vector following treatment with MC2580 or DMSO. Data are presented as mean of triplicates±SD.
Figure 21B:
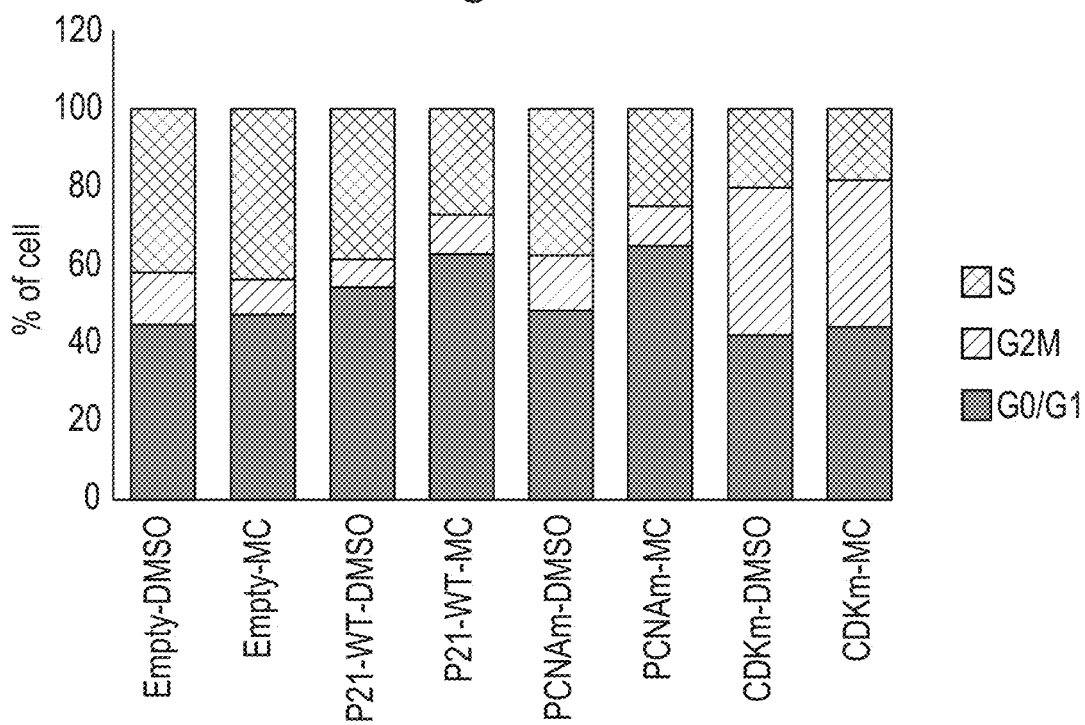
FIG. 21B depicts cell-cycle status of NB4 cells stably transduced with shRNA targeting p21 following transfection with empty or p21-WT, p21-PCNAm, p21-CDKm expression vector following treatment with MC2580 or DMSO.
Figure 21C:
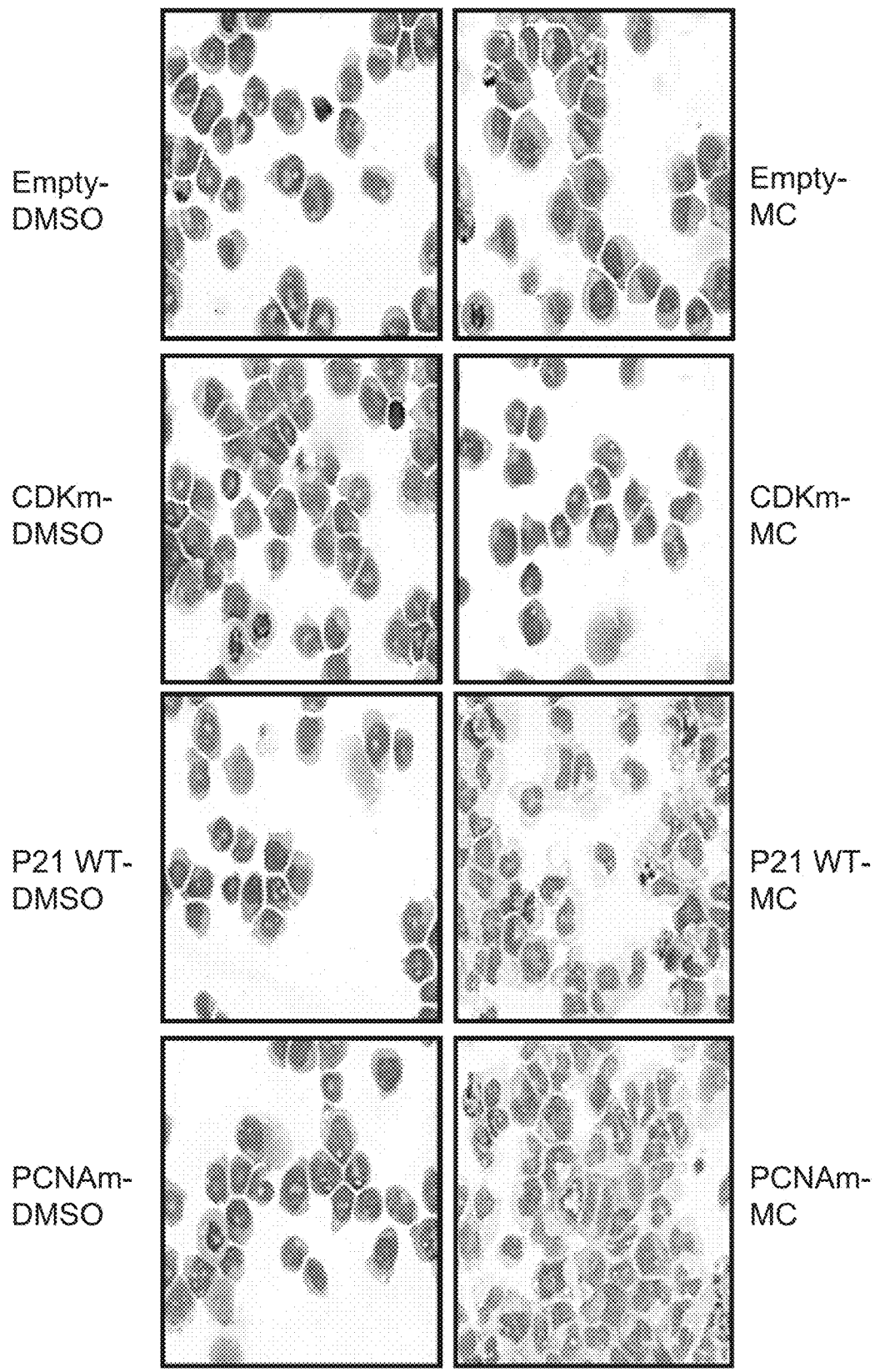
FIG. 21C depicts representative light micrograph show Wright-Giemsa staining of NB4 cell stably transduced with shRNA targeting p21 following transfection with empty or p21-WT, p21-PCNAm, p21-CDKm expression vector following treatment with MC2580 or DMSO. P value<0.05 (*), P<0.01 () and P<0.001 (*).

The proliferation of UF1 cells stably transduced with shRNA targeting p21 following transfection with empty, p21-WT, p21-PCNAm, or p21-CDKm expression vector following treatment with MC2580 or DMSO was analyzed and shown in FIG. 20A. NB4 cells without transfection were also included as control. The cell cycle analysis of these cells is shown in FIG. 20B. The morphology of the cells was assessed by the Wright-Giemsa staining and shown in FIG. 20C. The proliferation of NB4 cells stably transduced with shRNA targeting p21 following transfection with empty, p21-WT, p21-PCNAm, or p21-CDKm expression vector following treatment with MC2580 or DMSO was analyzed and shown in FIG. 21A. NB4 cells without transfection were also included as control. The cell cycle analysis of these cells are shown in FIG. 21B. The morphology of the cells was assessed by the Wright-Giemsa staining and shown in FIG. 21C. The data from the UF1 cells and NB4 cells suggests that the binding between p21 and CDK leads to cell cycle arrest and sensitizes cells to LSD1 inhibitor.

Example 16. LSD1 Regulates p21 Expression

Figure 22:
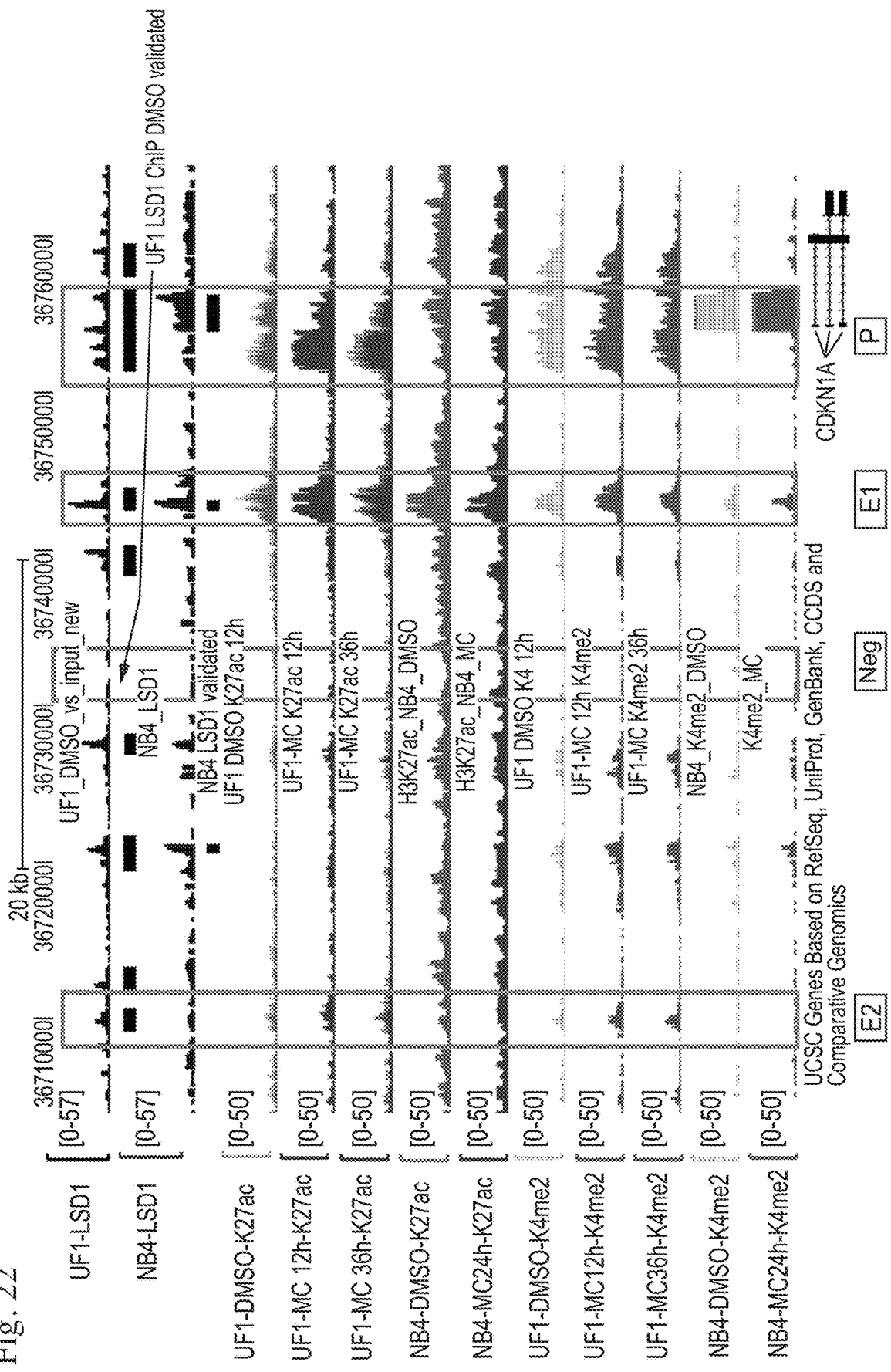
FIG. 22 depicts ChIP-seq profiles of LSD1, H3K4me2 and H3K27ac in the CDKN1A (p21) locus in UF1 and NB4 cells treated with DMSO or MC2580. SE is indicated by horizontal bars. (p: Promoter, E1: Enhancer 1, E2: Enhancer 2, Neg: Negative region for lsd1 binding site)

ChIP-seq (chromatin immunoprecipitation assays combined with sequencing) was performed to investigate the LSD1's effects on transcriptional regulation of p21 in UF1 and NB4 cells. H3K4me2 and H3K27ac in the CDKN1A (p21) locus were used as readout of p21 transcriptional expression. The UF1 cells were treated with MC2580 for 12 or 36 hours, or with DMSO. The NB4 cells were treated with MC2580 for 24 hours or with DMSO. The ChIP-seq profiles from the study are shown in FIG. 22.

Figure 23:
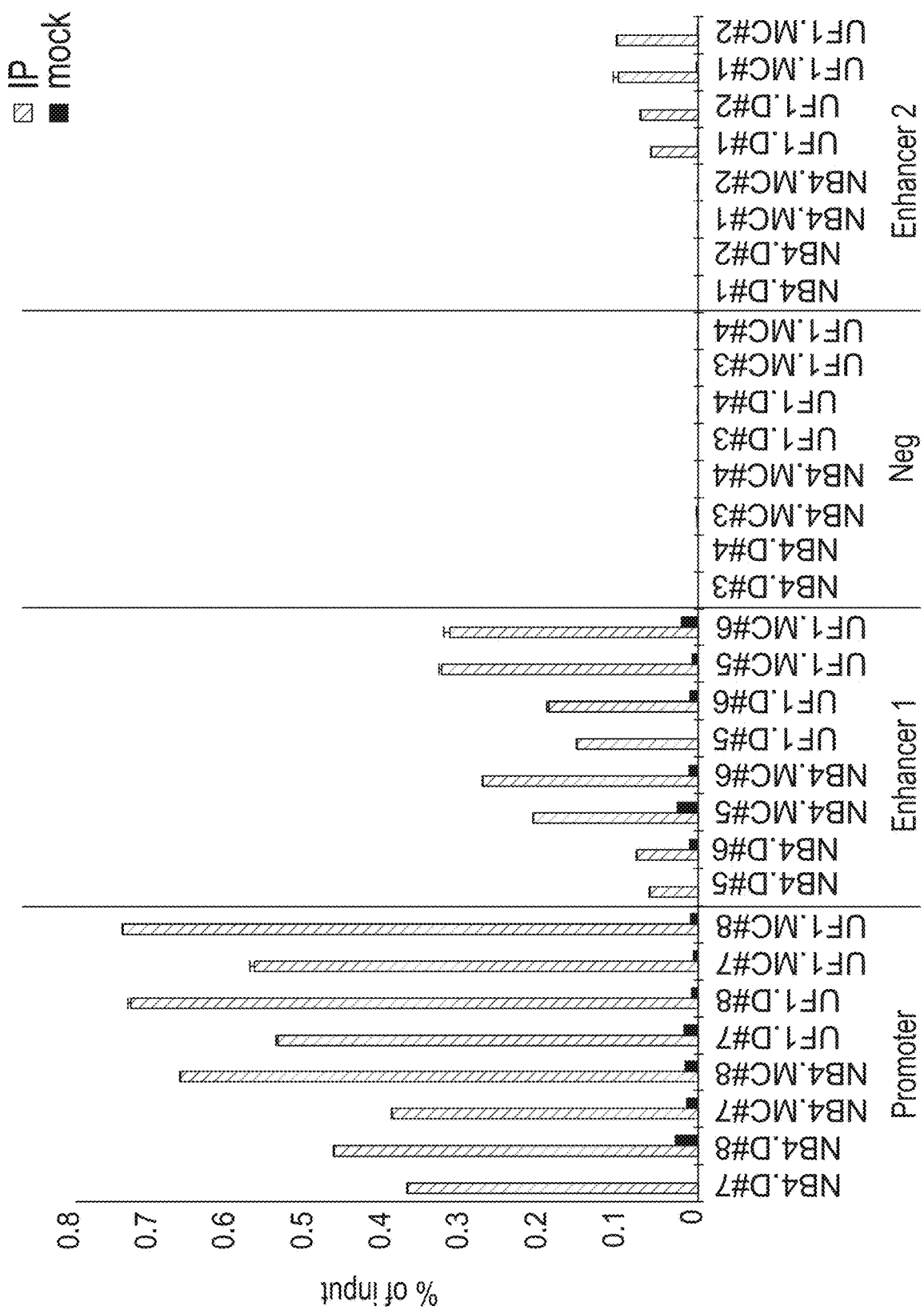
FIG. 23 depicts ChIP-qPCR occupancy analysis of LSD1 on p21 genomic loci in UF1 and NB4 cells treated with DMSO or MC2580 for 24 hours. For each region, two different primers were used. (p: Promoter, E1: Enhancer 1, E2: Enhancer 2, Neg: Negative region for LSD1 binding site)
Figure 24:
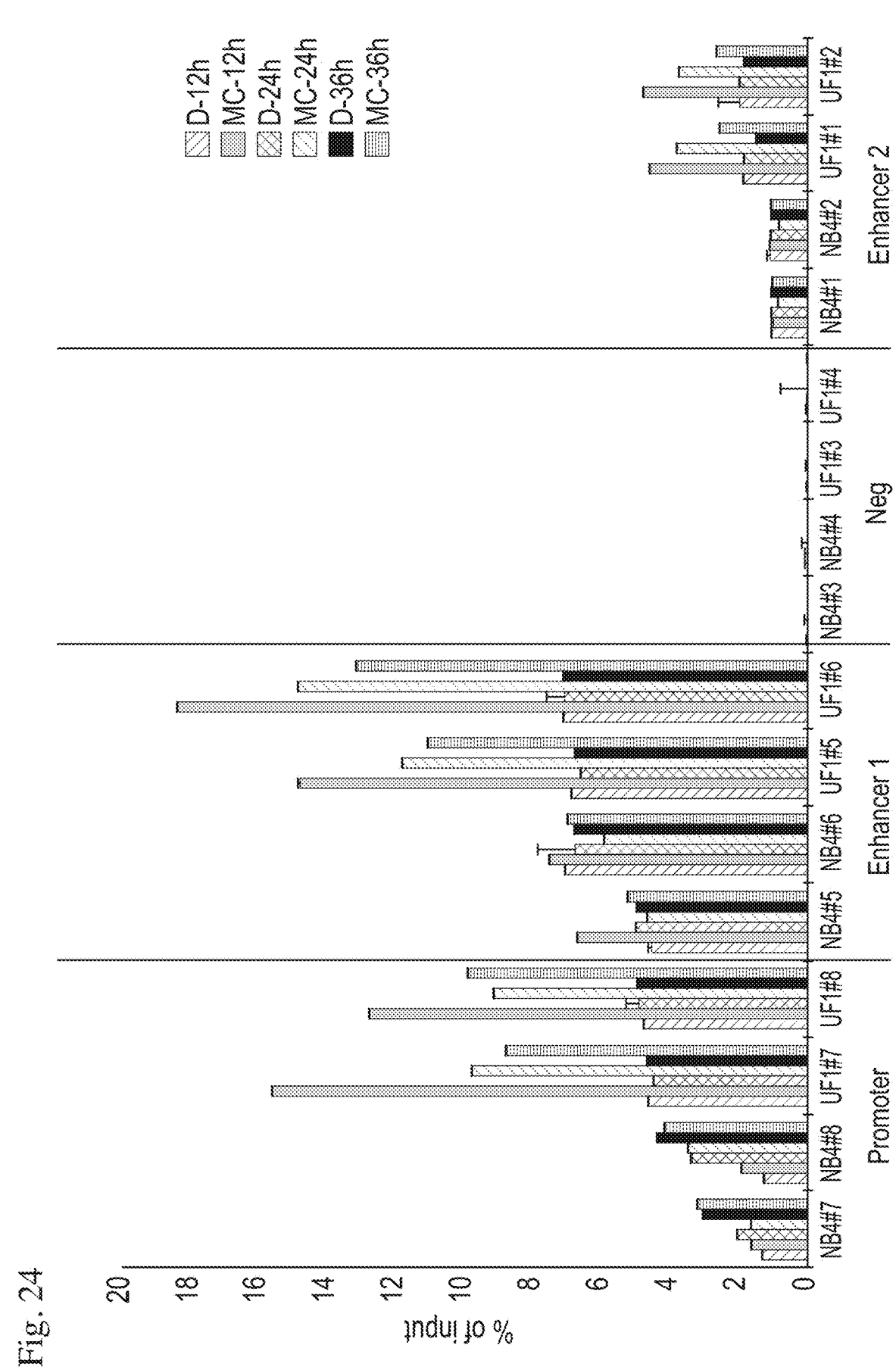
FIG. 24 depicts ChIP-qPCR occupancy analysis of H3K27ac on p21 genomic loci in UF1 and NB4 cells treated with DMSO or MC for 12 h, 24 h and 36 h. For each region, two different primers were used. (p: Promoter, E1: Enhancer 1, E2: Enhancer 2, Neg: Negative region for LSD1 binding site)
Figure 25:
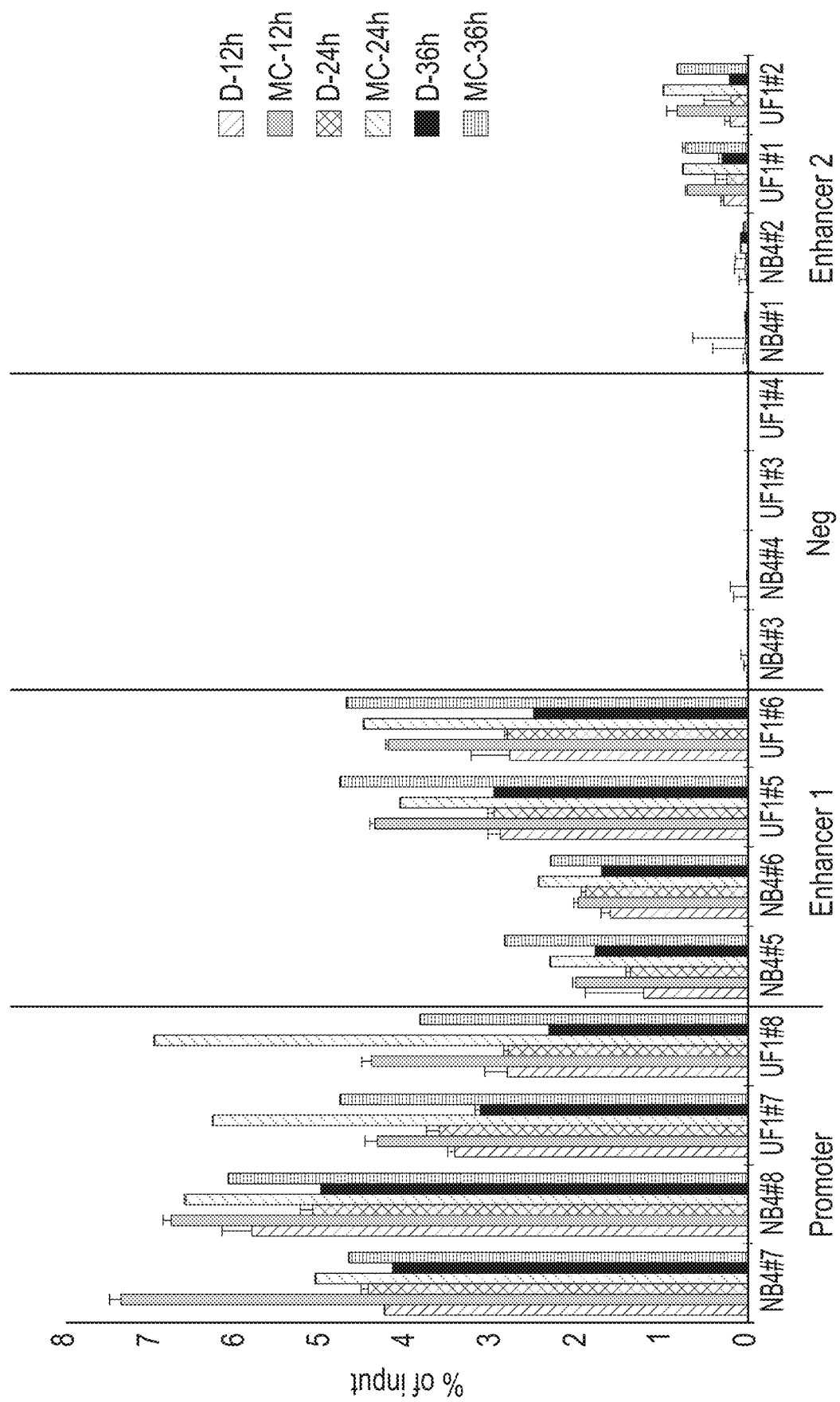
FIG. 25 depicts ChIP-qPCR occupancy analysis of H3K4me2 on P21 genomic loci in UF1 and NB4 cells treated with DMSO or MC for 12 h, 24 h and 36 h. For each region, two different primers were used. (p: Promoter, E1: Enhancer 1, E2: Enhancer 2, Neg: Negative region for LSD1 binding site)

ChIP-qPCR (chromatin immunoprecipitation assays combined with quantitative PCR) occupancy analysis of LSD1 on p21 genomic loci were also performed using UF1 and NB4 cells treated with DMSO or MC2580 for 24 hours, as shown in FIG. 23. ChIP-qPCR occupancy analysis of H3K27ac on p21 genomic loci in UF1 and NB4 cells treated with DMSO or MC2580 for 12, 24, or 36 hours was performed and is depicted in FIG. 24. ChIP-qPCR occupancy analysis of H3K4me2 on P21 genomic loci in UF1 and NB4 cells treated with DMSO or MC for 12, 24, or 36 hours was performed and is depicted in FIG. 25. The data demonstrates that LSD1 regulates p21 expression.

Figure 26:
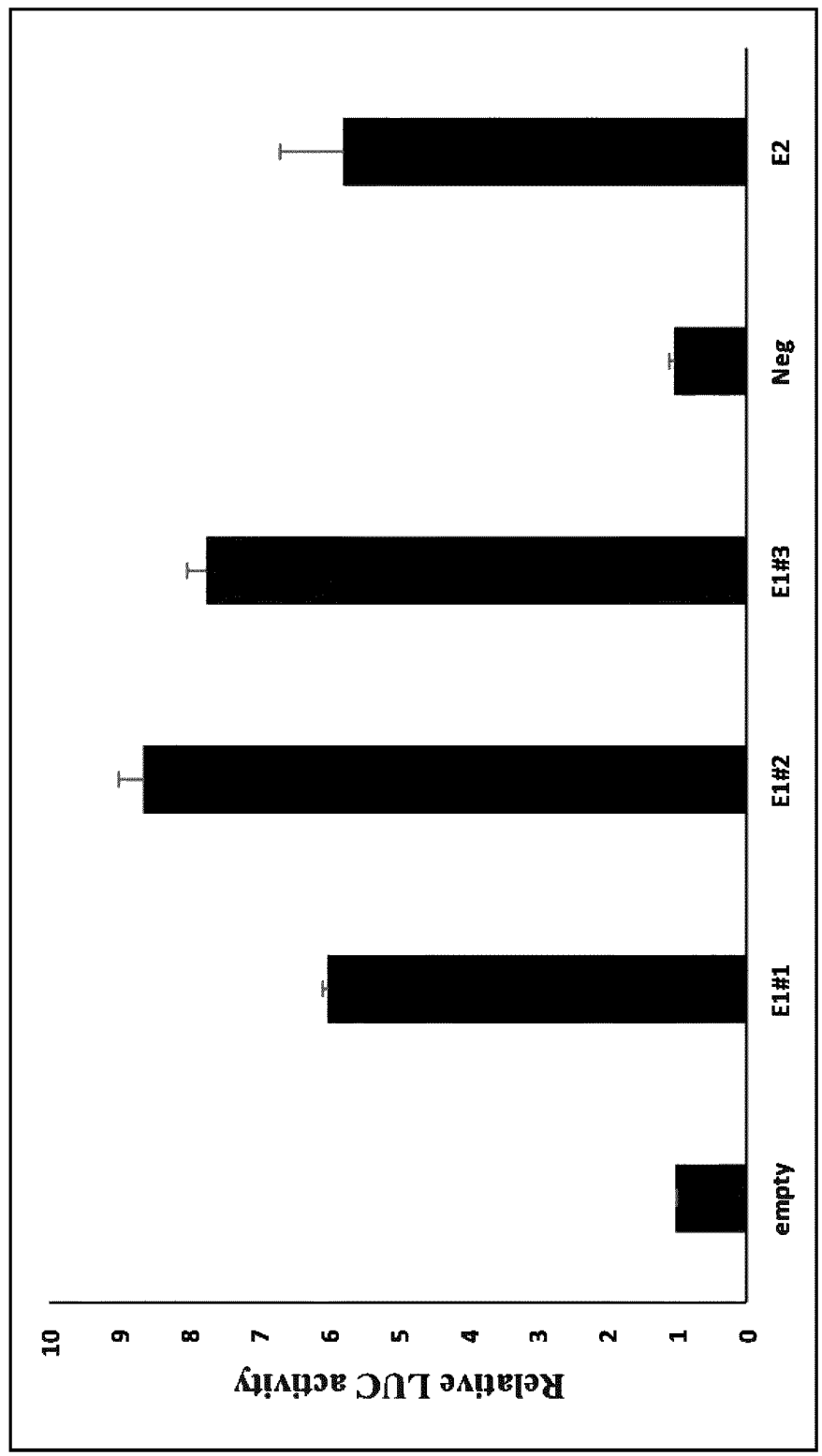
FIG. 26 depicts results from luciferase reporter assays, measuring the enhancer activity of E1 and E2 in 293T cells. Fragments E1 and E2 show enhancer activities, whereas negative (Neg) fragment shows no enhancer activity. The pGL3 plasmid without the enhancer region (empty) is used as a negative control. Error bars, s.e.m.
Figure 27:
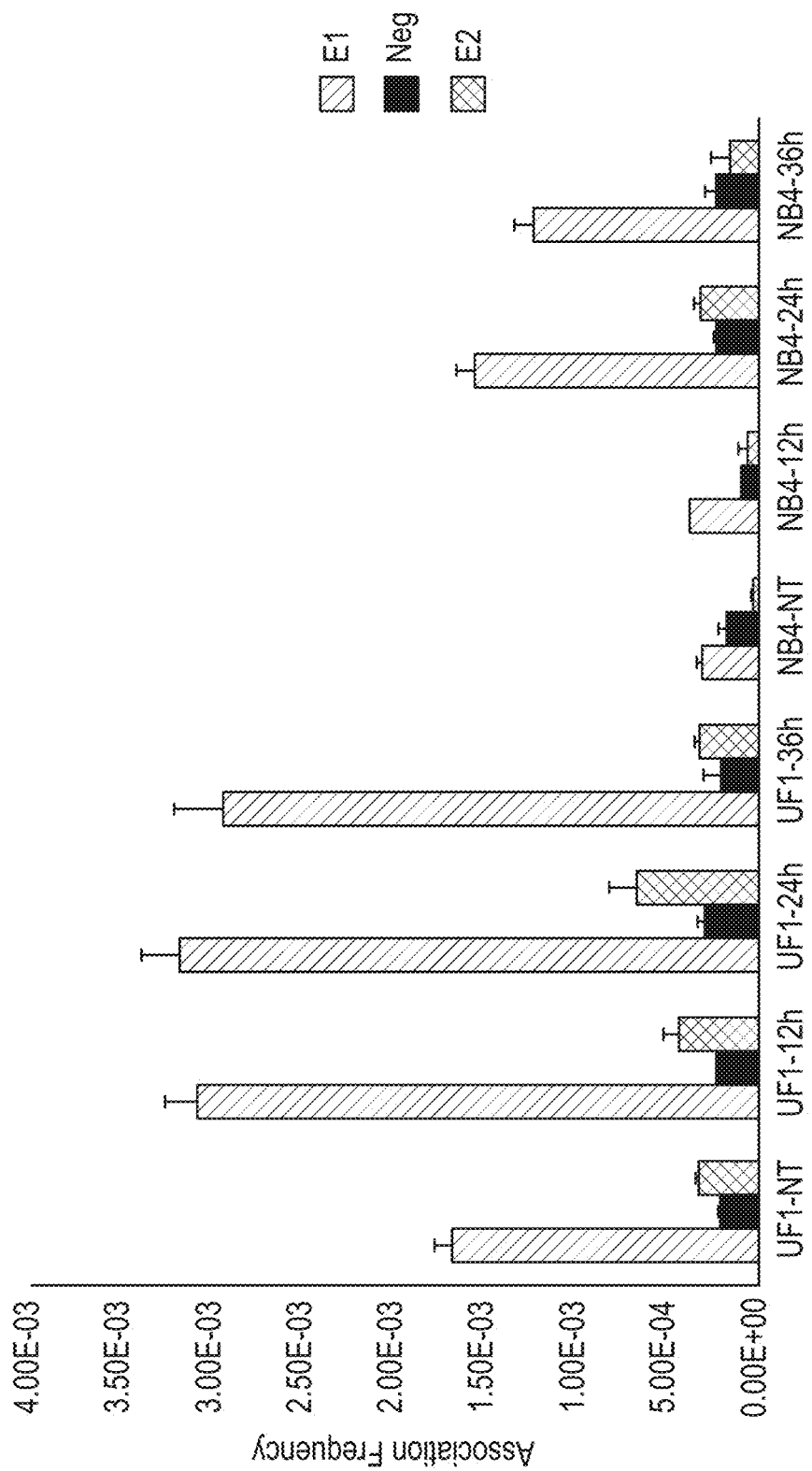
FIG. 27 depicts results from chromosome conformation capture assays (3C-qPCR) performed with chromatin from UF1 and NB4 cells that were treated for indicated times with the LSD1 inhibitor MC2580. (NT: not treated).

Luciferase reporter assays were performed to measure the activity of enhancer 1 ("E1") and enhancer 1 ("E2") of the p21 gene promoter in 293T cells and the results are depicted in FIG. 26. The pGL3 plasmid without the enhancer region (empty) was used as a negative control. Chromosome Conformation Capture assays (3C-qPCR) were performed with chromatin from UF1 and NB4 cells that were treated with the LSD1 inhibitor MC2580 for 12, 24, or 36 hours and the results are depicted in FIG. 27. Untreated cells ("Neg") were included as control. The data suggests that LSD1 inhibition induces dynamic looping of E1 and E2 regions to the transcription start site (TSS) of the p21 gene.

The invention claimed is:

1. A method for treating leukemia, lung cancer, or melanoma in a subject, comprising
administering to the subject in need thereof an effective amount of palbociclib and an effective amount of

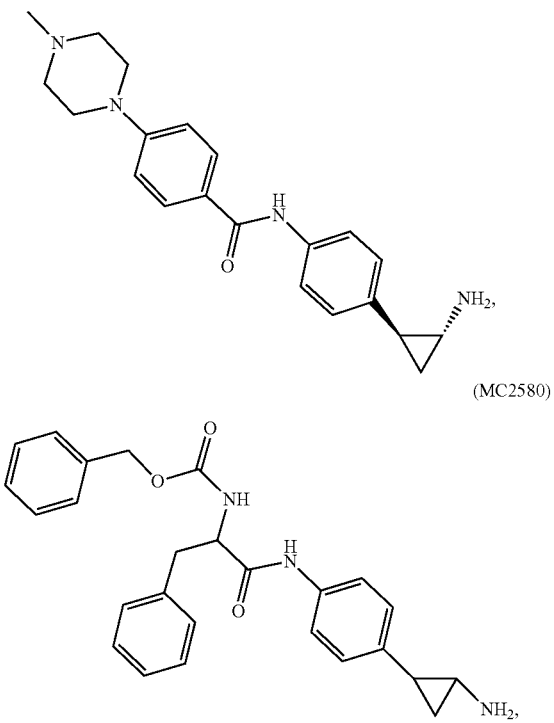

or a pharmaceutically acceptable salt thereof.

2. The method of claim 1, wherein palbociclib is administered to the subject before, concurrently, or after DDP38003, MC2580, or a pharmaceutically acceptable salt thereof.

3. The method of claim 1, wherein palbociclib is administered to the subject about 24 hours, about 48 hours, about 72 hours, or about 1 week before DDP38003, MC2580, or a pharmaceutically acceptable salt thereof.

4. The method of claim 1, wherein DDP38003, or a pharmaceutically acceptable salt thereof, is administered to the subject.

5. The method of claim 1, wherein MC2580, or a pharmaceutically acceptable salt thereof, is administered to the subject.

6. The method of claim 1, wherein the leukemia is acute promyelocytic leukemia or acute myeloid leukemia.

7. The method of claim 1, wherein the lung cancer is small cell lung carcinoma.

8. The method of claim 1, wherein the leukemia, lung cancer, or melanoma is a solid tumor or blood tumor.

9. The method of claim 1, wherein the leukemia, lung cancer, or melanoma is lysine-specific histone demethylase 1 (LSD1)-inhibitor-resistant.

10. The method of claim 9, wherein the LSD1-inhibitor-resistant leukemia, lung cancer, or melanoma comprises cancer cells having a reduced level of p21 expression or a loss of p21 function as compared to leukemia, lung cancer, or melanoma cancer cells that are sensitive to LSD1 inhibitors.

* * * * *